(12) United States Patent
Akahata et al.

(10) Patent No.: US 10,464,986 B2
(45) Date of Patent: *Nov. 5, 2019

(54) VIRUS LIKE PARTICLE COMPRISING PD-1 ANTIGEN OR PD-1 LIGAND ANTIGEN

(71) Applicant: VLP Therapeutics, LLC, Wilmington, DE (US)

(72) Inventors: Wataru Akahata, Kensington, MD (US); Ryuji Ueno, Easton, MD (US)

(73) Assignee: VLP Therapeutics, LLC, Wilmington, DE (US)

(*) Notice: Subject to any disclaimer, the term of this patent is extended or adjusted under 35 U.S.C. 154(b) by 0 days.

This patent is subject to a terminal disclaimer.

(21) Appl. No.: 15/498,971

(22) Filed: Apr. 27, 2017

(65) Prior Publication Data

US 2017/0233450 A1 Aug. 17, 2017

Related U.S. Application Data

(63) Continuation of application No. 14/328,268, filed on Jul. 10, 2014, now Pat. No. 9,637,532.

(60) Provisional application No. 61/845,712, filed on Jul. 12, 2013.

(51) Int. Cl.
| | |
|---|---|
| C07K 14/705 | (2006.01) |
| A61K 39/12 | (2006.01) |
| C07K 14/005 | (2006.01) |
| C12N 7/00 | (2006.01) |
| A61K 39/00 | (2006.01) |

(52) U.S. Cl.
CPC .... *C07K 14/70503* (2013.01); *A61K 39/0011* (2013.01); *A61K 39/12* (2013.01); *C07K 14/005* (2013.01); *C07K 14/705* (2013.01); *C07K 14/70596* (2013.01); *C12N 7/00* (2013.01); *A61K 39/00* (2013.01); *A61K 2039/5256* (2013.01); *A61K 2039/5258* (2013.01); *C07K 2319/40* (2013.01); *C07K 2319/735* (2013.01); *C12N 2770/36122* (2013.01); *C12N 2770/36123* (2013.01); *C12N 2770/36134* (2013.01); *Y02A 50/51* (2018.01)

(58) Field of Classification Search
CPC .... A61K 2039/5258; A61K 2039/5256; C07D 401/04; C07D 471/04; C07D 487/04; C07D 235/06; C07D 235/08; C07D 235/12; C07D 235/14; C07D 235/16; C07D 235/24; C07D 235/28; C07D 235/30; C07D 239/84; C07D 295/125; C07D 401/12; C07D 403/12; C07D 405/12; C07D 405/14; C07D 409/12; C07D 413/12; C07D 471/08; C07D 475/06; C07K 14/70503; C07K 14/70596; C07K 2319/00; C07K 2319/735; C12N 2770/36123; C12N 2760/1611; C12N 2770/26023; C12N 2770/26034; C12N 2770/26042; C12N 2770/36122
See application file for complete search history.

(56) References Cited

U.S. PATENT DOCUMENTS

| | | |
|---|---|---|
| 5,439,809 A | 8/1995 | Haynes et al. |
| 5,580,773 A | 12/1996 | Kang et al. |
| 5,629,204 A | 5/1997 | Honjo et al. |
| 5,698,520 A | 12/1997 | Honjo et al. |
| 5,939,598 A | 8/1999 | Kucherlapati et al. |
| 7,045,335 B2 | 5/2006 | Smith et al. |
| 7,078,218 B2 | 7/2006 | Smith et al. |
| 7,101,550 B2 | 9/2006 | Wood et al. |
| 7,595,048 B2 | 9/2009 | Honjo et al. |
| 7,790,181 B2 | 9/2010 | Platteborze et al. |
| 9,249,191 B2 | 2/2016 | Ueno et al. |
| 9,353,353 B2 | 5/2016 | Nabel |
| 9,363,353 B1 | 6/2016 | Chik |
| 9,487,563 B2 | 11/2016 | Nabel |
| 9,512,190 B2 | 12/2016 | Ueno |
| 9,637,532 B2 | 5/2017 | Akahata |
| 9,969,986 B2 | 5/2018 | Akahata et al. |
| 10,098,943 B2 | 10/2018 | Akahata et al. |
| 2003/0108521 A1 | 6/2003 | Calatrava |
| 2005/0214321 A1 | 9/2005 | Rasochova et al. |
| 2007/0104689 A1 | 5/2007 | Gillies et al. |
| 2007/0122378 A1 | 5/2007 | Freeman et al. |
| 2008/0025067 A1 | 1/2008 | Scheuerlein et al. |
| 2009/0079185 A1 | 3/2009 | Carbines-Evans et al. |
| 2009/0298955 A1 | 12/2009 | Handa et al. |
| 2009/0305950 A1 | 12/2009 | Minato et al. |
| 2009/0312190 A1 | 12/2009 | Chinea Santiago et al. |
| 2011/0027306 A1 | 2/2011 | Rayner et al. |
| 2011/0035004 A1 | 2/2011 | Maxwell |
| 2011/0081341 A1 | 4/2011 | Honjo et al. |
| 2011/0207223 A1 | 8/2011 | Tang et al. |
| 2011/0262389 A1 | 10/2011 | Mosca |
| 2011/0318373 A1 | 12/2011 | Sasikumar et al. |
| 2012/0003266 A1 | 1/2012 | Nable et al. |
| 2013/0122262 A1 | 5/2013 | Nagakura et al. |
| 2013/0251744 A1 | 9/2013 | Ueno et al. |
| 2014/0120125 A1 | 5/2014 | Ella et al. |
| 2014/0127247 A1 | 5/2014 | Dubensky |
| 2014/0170186 A1 | 6/2014 | Nabel et al. |

(Continued)

FOREIGN PATENT DOCUMENTS

| | | |
|---|---|---|
| CN | 102321639 | 1/2012 |
| CN | 106085974 A | 11/2016 |

(Continued)

OTHER PUBLICATIONS

Charoensri et al., "An optimized expression vector for improving the yield of dengue virus-like particles from transfected insect cells" Journal of Virological Methods, vol. 205, 2014, pp. 116-123.

(Continued)

*Primary Examiner* — Bao Q Li
(74) *Attorney, Agent, or Firm* — Sughrue Mion, PLLC

(57) ABSTRACT

The present invention provides a virus like particle comprising a virus structural protein and an antigen derived from PD-1 or a ligand of PD-1, and a composition or kit comprising thereof, its use in immune response etc.

17 Claims, 1 Drawing Sheet
Specification includes a Sequence Listing.

(56) References Cited

U.S. PATENT DOCUMENTS

| | | | |
|---|---|---|---|
| 2014/0363458 | A1 | 12/2014 | Ueno et al. |
| 2015/0017194 | A1 | 1/2015 | Akahata et al. |
| 2016/0040134 | A1 | 2/2016 | Akahata et al. |
| 2016/0074501 | A1 | 3/2016 | Akahata et al. |
| 2016/0090403 | A1 | 3/2016 | Ueno et al. |
| 2016/0200775 | A1 | 7/2016 | Akahata et al. |
| 2016/0303221 | A1 | 10/2016 | Nabel |
| 2017/0035871 | A1 | 2/2017 | Ueno et al. |
| 2017/0065703 | A1 | 3/2017 | Akahata et al. |
| 2017/0252425 | A1 | 9/2017 | Akahata et al. |

FOREIGN PATENT DOCUMENTS

| | | |
|---|---|---|
| JP | 04506301 | 11/1992 |
| JP | 2007512842 | 5/2007 |
| JP | 2007-537761 A | 12/2007 |
| JP | 2008543774 | 12/2008 |
| RU | 2411040 C2 | 2/2011 |
| WO | 9310152 | 5/1993 |
| WO | 9712048 | 4/1997 |
| WO | 99/41383 A1 | 8/1999 |
| WO | 02/096939 A2 | 12/2002 |
| WO | 03/102166 A2 | 12/2003 |
| WO | 2004043399 | 5/2004 |
| WO | 2004/085660 A2 | 10/2004 |
| WO | 2006040334 | 4/2006 |
| WO | 2006088229 | 8/2006 |
| WO | 2007003384 | 1/2007 |
| WO | 2007/059715 A2 | 5/2007 |
| WO | 2007100098 | 9/2007 |
| WO | 2008025067 | 3/2008 |
| WO | 2009079185 | 6/2009 |
| WO | 2010062396 | 6/2010 |
| WO | 2011035004 | 3/2011 |
| WO | 2012006180 | 1/2012 |
| WO | 2012023995 | 2/2012 |
| WO | 2012106356 | 8/2012 |
| WO | 2012123755 | 9/2012 |
| WO | 2012/172574 A1 | 12/2012 |
| WO | 2013/009884 A1 | 1/2013 |
| WO | 2013/063248 A1 | 5/2013 |
| WO | 2013122262 | 8/2013 |
| WO | 2013/151764 A1 | 10/2013 |
| WO | 2015/005500 A1 | 1/2015 |
| WO | 2015/139784 A1 | 9/2015 |
| WO | 2016/021209 A1 | 2/2016 |
| WO | 2016109792 A2 | 7/2016 |
| WO | 2016/199936 A1 | 12/2016 |
| WO | 2016/210127 A1 | 12/2016 |
| WO | 2017/009873 A1 | 1/2017 |
| WO | 2017/015463 A2 | 1/2017 |

OTHER PUBLICATIONS

Cox et al., "Predicting Zika virus structural biology: Challenges and opportunities for intervention" Antiviral Chemistry and Chemotherapy, vol. 24, No. 3-4, 2015, pp. 118-126.
De Wispelaere et al., "Mutagenesis of the DI/DIII Linker in Dengue Virus Envelope Protein Impairs Viral Particle Assembly," Journal of Virology, vol. 86, No. 13, Jul. 2012, pp. 7072-7083. Abstract, Fig.1, Fig.8-9, p. 7073.
Elshuber et al., "Cleavage of protein prM is necessary for Infection of BHK-21 cells by tick-borne encephalitis virus," Journal of General Virology, vol. 84, 2003, pp. 183-191.
Elshuber et al., "Resuscitating Mutations in a Furin Cleavage-Deficient Mutant of the Flavivirus Tick-Borne Encephalitis Virus," Journal of Virology, vol. 79, No. 18, Sep. 2005, pp. 11813-11823.
Roldão et al., "Virus-like particles in vaccine development," Expert Rev. Vaccines, vol. 9, No. 10, 2010, pp. 1149-1176.
GenBank: AAB02517.1, "Structural polyprotein precursor, Venezuelan equine encephalitis virus," dated Nov. 17, 2004, retrieved from https://www.ncbi.nlm.nih.gov/protein/AAB02517.1.
GenBank, "Zika virus strain MR 766, complete genome," AY632535. 2, Nov. 23, 2010, (6 pages total), [Retrieved on May 16, 2017] Retrieved from the Internet, URL: <https://www.ncbi.nlm.nih.gov/nuccore/AY632535>.
Gorchakov et al.,"Comparative analysis of the alphavirus-based vectors expressing Rift Valley fever virus glycoproteins", Virology, vol. 366, 2007, pp. 212-225.
Haddow et al., "Genetic Characterization of Zika Virus Strains: Geographic Expansion of the Asian Lineage," PLOS Neglected Tropical Disease, Feb. 2012, vol. 6, Issue 2, e1477, pp. 1-7. (7 pages total).
Hsieh et al., "A strong endoplasmic reticulum retention signal in the stem-anchor region of the envelope glycoprotein of dengue virus type 2 affects the production of virus-like particles," Virology, vol. 374, No. 2, 2008, pp. 338-350, ISSN: 0042-6822.
Hsieh et al., "The Length of and Nonhydrophobic Residues in the Transmembrane Domain of Dengue Virus Envelope Protein Are Critical for Its Retention and Assembly in the Endoplasmic Reticulum," Journal of Virology, vol. 84, No. 9, Apr. 2010 , pp. 4782-4797.
WHO Dengue vaccine research, "Immunization, Vaccines and Biologicals", http://www.who.int/immunization/research/development/dengue_vaccines/en/ (total 3 pages).
Huang et al., "The dengue virus type 2 envelope protein fusion peptide is essential for membrane fusion," Virology, vol. 396, No. 2, 2010, pp. 305-315, ISSN:0042-6822, Table 1, Fig.5, pp. 310-313.
Khetarpal et al., "Dengue-specific subviral nanoparticles: design, creation and characterization," Journal of Nanobiotechnology, vol. 11, No. 15, 2013, pp. 1-8, ISSN: 1477-3155.
Kostyuchenko et al., "Structure of the thermally stable Zika virus", Nature, May 19, 2016, vol. 533, pp. 425-428. (12 pages total).
Larocca et al., "Vaccine Protection Against Zika Virus from Brazil," Nature, vol. 536, No. 7617, Aug. 25, 2016, pp. 474-478.
Lin et al., "Analysis of Epitopes on Dengue Virus Envelope Protein Recognized by Monoclonal Antibodies and Polyclonal Human Sera by a High Throughput Assay", PLOS Neglected Tropical Diseases, Jan. 2012, vol. 6, Issue 1, e1447, pp. 1-12.
Ozden et al., "Inhibition of Chikungunya Virus Infection in Cultured Human Muscle Cells by Furin Inhibitors," Journal of Biological Chemistry, vol. 283, No. 32, Aug. 8, 2008, pp. 21899-21908.
Purdy et al., "Secretion of noninfectious dengue virus-like particles and identification of amino acids in the stem region involved in intracellular retention of envelope protein," Virology, vol. 333, 2005, pp. 239-250.
Pushko et al., "Replicon-Helper Systems from Attenuated Venezuelan Equine Encephalitis Virus: Expression of Heterologous Genes in Vitro and Immunization against Heterologous Pathogens in Vivo," Virology, vol. 239, 1997, pp. 389-401.
Richner et al., "Modified mRNA Vaccines Protect against Zika Virus Infection" Cell, vol. 168., Mar. 9, 2017, pp. 1114-1125. (23 pages total).
Seligman, "Constancy and diversity in the flavivirus fusion peptide," Virology Journal, vol. 5, No. 27, Feb. 14, 2008. (10 pages total).
Taylor et al., "Production of immunogenic West Nile virus-like particles using a herpes simplex virus 1 recombinant vector," Virology, vol. 496, 2016, pp. 186-193.
Tsai et al., "Complexity of Neutralizing Antibodies against Multiple Dengue Virus Serotypes after Heterotypic Immunization and Secondary Infection Revealed by In-Depth Analysis of Cross-Reactive Antibodies," Journal of Virology, vol. 89, No. 14, 2015, pp. 7348-7362.
Heinz et al., "Flaviviruses and flavivirus vaccines," Vaccine, vol. 30, 2012, pp. 4301-4306.
Yamaji et al., "Efficient production of Japanese encephalitis virus-like particles by recombinant lepidopteran insect cells," Appl Microbiol Biotechnol, vol. 97, 2013, pp. 1071-1079.
Zhang et al., "Vaccination with dengue virus-like particles induces humoral and cellular immune responses in mice," Virology Journal, vol. 8, No. 333, pp. 1-9.
Zika virus Fact sheet, Updated Sep. 6, 2016, URL:http://www.who.int/mediacentre/factsheets/zika/en/ (5 pages total).
Urakami et al., "Development of a Novel Virus-Like Particle Vaccine Platform That Mimics the Immature Form of Alphavirus," Clinical and Vaccine Immunology, 24(7): e00090-17 (pp. 1-14).

(56) References Cited

OTHER PUBLICATIONS

Communication, dated Dec. 20, 2017, issued by the European Patent Office in counterpart European Patent Application No. 15829311.8.
Communication, dated Jun. 20, 2017, issued by the Japanese Patent Office in Japanese Patent Application No. 2014-557308.
Hevey et al., "Marburg Virus Vaccines Based upon Alphavirus Replicons Protect Guinea Pigs and Nonhuman Primates", Virology, vol. 251, 1998, pp. 28-37. (11 pages total).
Communication, dated Jun. 6, 2017, issued by the United States Patent and Trademark Office in U.S. Appl. No. 15/299,859.
Bonaldo et al., "Surface Expression of an Immunodominant Malaria Protein B Cell Epitope by Yellow Fever Virus", J. Mol. Biol., vol. 315, No. 4, Jan. 25, 2002, pp. 873-885. (13 pages total).
Vuola et al. "Differential Immunogenicity of Various Heterologous Prime-Boost Vaccine Regimes Using DNA and Viral Vectors in Healthy Volunteers", The Journal of Immunology, vol. 174, No. 1, Jan. 1, 2005, pp. 449-455. (7 pages total).
Communication in European Application No. 14823398.4, dated Jan. 2, 2017.
Communication in European Application No. 14807026.1, dated Jul. 5, 2016.
Communication in European Application No. 13749307.8, dated Oct. 2, 2015.
Communication in European Application No. 13749307.8, dated Sep. 16, 2015.
Crompton et al, "Advances and challenges in malaria vaccine development", Science in medicine, The Journal of Clinical Investigation, 120(12):4168-4178 (2010).
Dobano et al., "Alphavirus replicon particles are highly immunogenic in the murine Malaria model by homologous or heterologous immunization", Open Vaccine Journal, 1:27-37 (2008).
Grgacic et al., "Virus-like particles: Passport to immune recognition", Methods, 40:60-65 (2006).
Notka et al., "Accelerated clearance of SHIV in rhesus monkeys by virus-like particle vaccines is dependent on induction of neutralizing antibodies", Vaccine, 18(3-4):291-301 (2000).
Federico, "Virus-like particles show promise as candidates for new vaccine strategies". Future Virol., 5(4):371-374 (2010).
Jennings et al., "Immunodrugs: Therapeutic VLP-Based Vaccines for Chronic Diseases", Annu. Rev. Pharmacol. Toxicol., 49:303-326 (2009).
GenBank: AAW78190.1, circumsporozoite protein, partial [Plasmodium falciparum], http://www.ncbi.nlm.nih.gov/protein/58429573?report=genbank&log$=protalign&blast_rank=18&RID=P92DM05R01 R, Dec. 29, 2006.
GenBank: ADG95942.1 structural polyprotein [Chikungunya virus], http://www.ncbi.nlm.nih.gov/protein/296124572?report=genbank&log$=protalign&blast_rank=2&RID=PBR7NT0U015, Dec. 28, 2010.
Ghasparian et al., Engineered synthetic virus-like particles and their use in vaccine delivery, Chembiochem, 12(1):100-109 (2011).
Gilbert et al., A protein particle vaccine containing multiple Malaria epitopes, Nat. Biotechnol., 15(12):1280-1284 (1997).
Atkins et al., "Therapeutic and prophylactic applications of alphavirus vectors", Expert Reviews in Molecular Medicine, 10(e33):1-17 (2008).
Gregson et al., "Phase I Trial of an Alhydrogel Adjuvanted Hepatitis B Core Virus-Like Particle Containing Epitopes of *Plasmodium falciparum* Circumsporozoite Protein", PLoS ONE, 3(2):e1556 (2008).
Roldão et al., "Virus-like particles in vaccine development", Expert Rev. Vaccines, 9(10):1149-1176 (2010).
Adams et al., "The expression of hybrid HIV:Ty virus-like particles in yeast", Nature, 329(6134):68-70 (1987).
Akahata et al., "A specific domain of the Chikungunya virus E2 protein regulates particle formation in human cells: implications for alphavirus vaccine design", J. Virol., 86(16):8879-8883 (2012).
Allsopp et al., "Comparison of numerous delivery systems for the induction of cytotoxic T lymphocytes by immunization", Eur. J. Immunol., 26(8):1951-1959 (1996).
Birkett et al., "A Modified Hepatitis B Virus Core Particle Containing Multiple Epitopes of the *Plasmodium falciparum* Circumsporozoite Protein Provides a Highly Immunogenic Malaria Vaccine in Preclinical Analyses in Rodent and Primate Hosts", Infection and Immunity, 70(12) 6860-6870 (2002).
Chackerian et al., "Determinants of Autoantibody Induction by Conjugated Papillomavirus Virus-Like Particles", The Journal of Immunology, 169:6120-6126 (2002).
Calvo-Calle et al., "A Linear Peptide Containing Minimal T- and B-Cell Epitopes of *Plasmodium falciparum* Circumsporozoite Protein Elicits Protection against Transgenic Sporozoite Challenge", Infection and Immunity, 74(12):6929-6939 (2006).
Carvalho et al., "Malaria Vaccine: Candidate Antigens, Mechanisms, Constraints and Prospects", Scand. J. Immunol., 56:327-343 (2002).
Roberts et al., "Vaccination with CD20 peptides induces a biologically active, specific immune response in mice", Blood, 99:3748-3755 (2002).
Agata et al., "Expression of the PD-1 antigen on the surface of stimulated mouse T and B lymphocytes", International Immunology, 8(5):765-772 (1996).
Spohn et al., "A Virus-Like Particle-Based Vaccine Selectively Targeting Soluble TNF-a Protects from Arthritis without Inducing Reactivation of Latent Tuberculosis", The Journal of Immunology, 178: 7450-7457 (2007).
Leibl et al., "Adjuvant/carrier activity of inactivated tick-borne encephalitis virus", Vaccine, 16(4): 340-345 (1998).
International Search Report with Written Opinion for PCT/JP2014/065166, dated Sep. 16, 2014.
International Search Report with Written Opinion for PCT/JP2014/069122, dated Oct. 21, 2014.
Mellman et al., "Cancer immunotherapy comes of age", Nature, 480:480-489 (2011).
Jones et al., "A plant-produced Pfs25 VLP Malaria Vaccine Candidate Induces Persistent Transmission Blocking Antibodies against *Plasmodium falciparum* in immunized mice", PLoS One, 8(11):e79538, (2013), doi:10.1371/journal.pone.0079538.
McCoy et al., "Cytotoxic T Lymphocyte-associated Antigen 4 (CTLA-4) Can Regulate Dendritic Cell-induced Activation and Cytotoxicity of CD8+ T Cells Independently of CD4+ T Cell Help", J. Exp. Med., 189(7):1157-1162 (1999).
Kuo et al., "Cell-based analysis of Chikungunya virus E1 protein in membrane fusion", J. Biomed. Sci., 19(44):1-12 (2012).
Lechner et al., "Virus-like particles as a modular system for novel vaccines", Intervirology, 45(4-6):212-217 (2002).
Malaria Vaccine Program, http://www.globalvaccines.org/content/malaria+vaccine+program/19614, 4pages (2012).
Palomba et al., "CD8+T-Cell-Dependent Immunity Following Xenogeneic DNA Immunization against CD20 in a Tumor Challenge Model of B-Cell Lymphoma", Clinical Cancer Research, 370(11):370-379 (2005).
Milich et al. "Conversion of poorly immunogenic malaria repeat sequences into a highly immunogenic vaccine candidate", Vaccine, 20(5-6):771-788 (2001).
Oliveira et al., "Safety and enhanced immunogenicity of a Hepatitis B core particle *Plasmodium falciparum* Malaria vaccine formulated in adjuvant montanide ISA 720 in a Phase I Trial", Infect. Immun., 73(6):3587-3597 (2005).
Oliveira-Ferreira et al.. "Immunogenicity of Ty-VLP bearing a CD8(+) T cell epitope of the CS protein of *P. yoelii*: enhanced memory response by boosting with recombinant vaccinia virus", Vaccine, 18(17):1863-1869 (2000).
Pfeiffer et al., A virosome-mimotope approach to synthetic vaccine design and optimization: synthesis, conformation, and immune recognition of a potential Malaria-vaccine candidate, Angew. Chem. Int. Ed., 42(21):2368-2371 (2003).
Rodrigues et al., Influenza and Vaccinia viruses expressing Malaria CD8+T and B Cell epitopes. Comparison of their immunogenicity and capacity to induce protective immunity, J. Immunol., 153(10):4636-4648 (1994).

(56) References Cited

OTHER PUBLICATIONS

Rodriguez et al., Vaccine Efficacy against malaria by the Combination of Porcine Parvovirus-Like Particles and Vaccinia Virus Vectors Expressing CS of Plasmodium, PLoS One, 7(4):e34445 (2012).
Search Report issued in International Application No. PCT/JP2013/054422, dated May 28, 2013.
Shiratsuchi et al. "Replacing adenoviral vector HVR1 with a malaria B cell epitope improves immunogenicity and circumvents preexisting immunity to adenovirus in mice", Journal of Clinical Investigation, 120(10):3688-3701 (2010).
Sun et al., "Structural analyses at pseudo atomic resolution of Chikungunya virus and antibodies show mechanisms of neutralization", eLIFE, 2:1-27 (2013).
Arora et al., "Virus-like particles displaying envelope domain III of dengue virus type 2 induce virus-specific antibody response in mice", Vaccine, 31(6):873-878 (2013).
Akahata et al, U.S. Appl. No. 14/820,785, filed Aug. 7, 2015.
Akahata et al., "A VLP vaccine for epidemic Chikungunya virus protects non-human primates against infection", Nat Med., vol. 16, No. 3, 12 pages (2010).
Office Action dated Nov. 19, 2014 in U.S. Appl. No. 13/768,801.
Office Action dated Apr. 1, 2015 in U.S. Appl. No. 13/768,801.
Notice of Allowance dated Nov. 6, 2015 in U.S. Appl. No. 13/768,801.
Office Action dated Jun. 9, 2015 in U.S. Appl. No. 14/294,968.
Office Action dated Dec. 3, 2015 in U.S. Appl. No. 14/294,968.
Advisory Action dated Mar. 29, 2016 in U.S. Appl. No. 14/294,968.
Notice of Allowance dated Jul. 26, 2016 in U.S. Appl. No. 14/294,968.
Liu et al., "Recombinant dengue virus-like particles from Pichia pastoris: efficient production and immunological properties," Vir. Genes, 2010: 40:53-59.
Berthet et al. GenBank: AHF49783.1; 2015.
Enfissi et al. GenBank: ALX35659.1, 2016.
Manjila et al., "Novel Gene Delivery Systems", International Journal of Pharmaceutical Investigation, Jan. 2013, vol. 3, Issue 1, pp. 1-7.
Chhabra, et al., "Chikungunya fever: A re-emerging viral infection" Indian J Med Microbiol. Jan.-Mar. 2008, vol. 26, No. 1, pp. 5-12.
De Lamballerie et al., "Chikungunya virus adapts to tiger mosquito via evolutionary convergence: a sign of things to come?", Virology Journal 2008, vol. 5, No. 33, pp. 1-4.
Veltrop-Duits et al., "Human CD4+ T cells stimulated by conserved adenovirus 5 hexon peptides recognize cells infected with different species of human adenovirus", Eur. J. Immunol., 2006, vol. 36, pp. 2410-2423 (14 pages total).
Akane Urakami et al., "An Envelope-Modified Tetravalent Dengue Virus-Like-Particle Vaccine Has Implications for Flavivirus Vaccine Design", Journal of Virology, Dec. 2017, vol. 91, Issue 23, e01181-17 (16 pages total).
Palucha et al., "Virus-Like Particles: Models for Assembly Studies and Foreign Epitope Carriers," Progress in Nucleic Acid Research and Molecular Biology, 2005, vol. 30, pp. 135-168.
Metz et al., "Low Temperature-Dependent Salmonid Alphavirus Glycoprotein Processing and Recombinant Virus-Like Particle Formation," PLoS One, 2011, vol. 6, Issue 10, pp. 1-10.
Chhabra, et al., "Chikungunya fever: A re-emerging viral infection" Indian J Med Microbiol. Jan-Mar 2008, Vol.26, no. 1, pp. 5-12.
Veltrop-Duits et al., "Human CD4+ T cells stimulated by conserved adenovirus 5 hexon peptides recognize cells infected with different species of human adenovirus", Eur. J. Immunol., 2006, vol. 36, pp. 2410-2423 (14 pp. total).
Akane Urakami et al., "An Envelope-Modified Tetravalent Dengue Virus-Like-Particle Vaccine Has Implications for Flavivirus Vaccine Design", Journal of Virology, Dec. 2017, vol. 91, Issue 23, e01181-17 (16 pp. total).

SEQUENCE LISTING

<160> NUMBER OF SEQ ID NOS: 64

<210> SEQ ID NO 1
<211> LENGTH: 1248
<212> TYPE: PRT
<213> ORGANISM: Chikungunya virus

<400> SEQUENCE: 1

```
Met Glu Phe Ile Pro Thr Gln Thr Phe Tyr Asn Arg Arg Tyr Gln Pro
1               5                   10                  15

Arg Pro Trp Thr Pro Arg Pro Thr Ile Gln Val Ile Arg Pro Arg Pro
            20                  25                  30

Arg Pro Gln Arg Gln Ala Gly Gln Leu Ala Gln Leu Ile Ser Ala Val
        35                  40                  45

Asn Lys Leu Thr Met Arg Ala Val Pro Gln Gln Lys Pro Arg Arg Asn
    50                  55                  60

Arg Lys Asn Lys Lys Gln Lys Gln Lys Gln Gln Ala Pro Gln Asn Asn
65                  70                  75                  80
```

-continued

```
Thr Asn Gln Lys Lys Gln Pro Pro Lys Lys Pro Ala Gln Lys Lys
                85                  90                  95
Lys Lys Pro Gly Arg Arg Glu Arg Met Cys Met Lys Ile Glu Asn Asp
            100                 105                 110
Cys Ile Phe Glu Val Lys His Glu Gly Lys Val Thr Gly Tyr Ala Cys
            115                 120                 125
Leu Val Gly Asp Lys Val Met Lys Pro Ala His Val Lys Gly Thr Ile
        130                 135                 140
Asp Asn Ala Asp Leu Ala Lys Leu Ala Phe Lys Arg Ser Ser Lys Tyr
145                 150                 155                 160
Asp Leu Glu Cys Ala Gln Ile Pro Val His Met Lys Ser Asp Ala Ser
                165                 170                 175
Lys Phe Thr His Glu Lys Pro Glu Gly Tyr Tyr Asn Trp His His Gly
            180                 185                 190
Ala Val Gln Tyr Ser Gly Gly Arg Phe Thr Ile Pro Thr Gly Ala Gly
            195                 200                 205
Lys Pro Gly Asp Ser Gly Arg Pro Ile Phe Asp Asn Lys Gly Arg Val
        210                 215                 220
Val Ala Ile Val Leu Gly Gly Ala Asn Glu Gly Ala Arg Thr Ala Leu
225                 230                 235                 240
Ser Val Val Thr Trp Asn Lys Asp Ile Val Thr Lys Ile Thr Pro Glu
                245                 250                 255
Gly Ala Glu Glu Trp Ser Leu Ala Ile Pro Val Met Cys Leu Leu Ala
            260                 265                 270
Asn Thr Thr Phe Pro Cys Ser Gln Pro Pro Cys Thr Pro Cys Cys Tyr
            275                 280                 285
Glu Lys Glu Pro Glu Glu Thr Leu Arg Met Leu Glu Asp Asn Val Met
        290                 295                 300
Arg Pro Gly Tyr Tyr Gln Leu Leu Gln Ala Ser Leu Thr Cys Ser Pro
305                 310                 315                 320
His Arg Gln Arg Arg Ser Thr Lys Asp Asn Phe Asn Val Tyr Lys Ala
                325                 330                 335
Thr Arg Pro Tyr Leu Ala His Cys Pro Asp Cys Gly Glu Gly His Ser
            340                 345                 350
Cys His Ser Pro Val Ala Leu Glu Arg Ile Arg Asn Glu Ala Thr Asp
            355                 360                 365
Gly Thr Leu Lys Ile Gln Val Ser Leu Gln Ile Gly Ile Lys Thr Asp
        370                 375                 380
Asp Ser His Asp Trp Thr Lys Leu Arg Tyr Met Asp Asn His Met Pro
385                 390                 395                 400
Ala Asp Ala Glu Arg Ala Gly Leu Phe Val Arg Thr Ser Ala Pro Cys
                405                 410                 415
Thr Ile Thr Gly Thr Met Gly His Phe Ile Leu Ala Arg Cys Pro Lys
            420                 425                 430
Gly Glu Thr Leu Thr Val Gly Phe Thr Asp Ser Arg Lys Ile Ser His
            435                 440                 445
Ser Cys Thr His Pro Phe His His Asp Pro Pro Val Ile Gly Arg Glu
        450                 455                 460
Lys Phe His Ser Arg Pro Gln His Gly Lys Glu Leu Pro Cys Ser Thr
465                 470                 475                 480
Tyr Val Gln Ser Thr Ala Ala Thr Glu Glu Ile Glu Val His Met
                485                 490                 495
```

-continued

```
Pro Pro Asp Thr Pro Asp Arg Thr Leu Met Ser Gln Gln Ser Gly Asn
            500             505             510

Val Lys Ile Thr Val Asn Gly Gln Thr Val Arg Tyr Lys Cys Asn Cys
            515             520             525

Gly Gly Ser Asn Glu Gly Leu Thr Thr Thr Asp Lys Val Ile Asn Asn
            530             535             540

Cys Lys Val Asp Gln Cys His Ala Ala Val Thr Asn His Lys Lys Trp
545             550             555             560

Gln Tyr Asn Ser Pro Leu Val Pro Arg Asn Ala Glu Leu Gly Asp Arg
            565             570             575

Lys Gly Lys Ile His Ile Pro Phe Pro Leu Ala Asn Val Thr Cys Arg
            580             585             590

Val Pro Lys Ala Arg Asn Pro Thr Val Thr Tyr Gly Lys Asn Gln Val
            595             600             605

Ile Met Leu Leu Tyr Pro Asp His Pro Thr Leu Leu Ser Tyr Arg Asn
            610             615             620

Met Gly Glu Glu Pro Asn Tyr Gln Glu Glu Trp Val Met His Lys Lys
625             630             635             640

Glu Val Val Leu Thr Val Pro Thr Glu Gly Leu Glu Val Thr Trp Gly
            645             650             655

Asn Asn Glu Pro Tyr Lys Tyr Trp Pro Gln Leu Ser Thr Asn Gly Thr
            660             665             670

Ala His Gly His Pro His Glu Ile Ile Leu Tyr Tyr Tyr Glu Leu Tyr
            675             680             685

Pro Thr Met Thr Val Val Val Ser Val Ala Thr Phe Ile Leu Leu
            690             695             700

Ser Met Val Gly Met Ala Ala Gly Met Cys Met Cys Ala Arg Arg Arg
705             710             715             720

Cys Ile Thr Pro Tyr Glu Leu Thr Pro Gly Ala Thr Val Pro Phe Leu
            725             730             735

Leu Ser Leu Ile Cys Cys Ile Arg Thr Ala Lys Ala Ala Thr Tyr Gln
            740             745             750

Glu Ala Ala Ile Tyr Leu Trp Asn Glu Gln Gln Pro Leu Phe Trp Leu
            755             760             765

Gln Ala Leu Ile Pro Leu Ala Ala Leu Ile Val Leu Cys Asn Cys Leu
            770             775             780

Arg Leu Leu Pro Cys Cys Cys Lys Thr Leu Ala Phe Leu Ala Val Met
785             790             795             800

Ser Val Gly Ala His Thr Val Ser Ala Tyr Glu His Val Thr Val Ile
            805             810             815

Pro Asn Thr Val Gly Val Pro Tyr Lys Thr Leu Val Asn Arg Pro Gly
            820             825             830

Tyr Ser Pro Met Val Leu Glu Met Glu Leu Leu Ser Val Thr Leu Glu
            835             840             845

Pro Thr Leu Ser Leu Asp Tyr Ile Thr Cys Glu Tyr Lys Thr Val Ile
            850             855             860

Pro Ser Pro Tyr Val Lys Cys Cys Gly Thr Ala Glu Cys Lys Asp Lys
865             870             875             880

Asn Leu Pro Asp Tyr Ser Cys Lys Val Phe Thr Gly Val Tyr Pro Phe
            885             890             895

Met Trp Gly Gly Ala Tyr Cys Phe Cys Asp Ala Glu Asn Thr Gln Leu
            900             905             910
```

```
Ser Glu Ala His Val Glu Lys Ser Glu Ser Cys Lys Thr Glu Phe Ala
            915                 920                 925

Ser Ala Tyr Arg Ala His Thr Ala Ser Ala Ser Ala Lys Leu Arg Val
        930                 935                 940

Leu Tyr Gln Gly Asn Asn Ile Thr Val Thr Ala Tyr Ala Asn Gly Asp
945                 950                 955                 960

His Ala Val Thr Val Lys Asp Ala Lys Phe Ile Val Gly Pro Met Ser
                965                 970                 975

Ser Ala Trp Thr Pro Phe Asp Asn Lys Ile Val Val Tyr Lys Gly Asp
            980                 985                 990

Val Tyr Asn Met Asp Tyr Pro Pro Phe Gly Ala Gly Arg Pro Gly Gln
        995                 1000                1005

Phe Gly Asp Ile Gln Ser Arg Thr Pro Glu Ser Lys Asp Val Tyr
    1010                1015                1020

Ala Asn Thr Gln Leu Val Leu Gln Arg Pro Ala Val Gly Thr Val
    1025                1030                1035

His Val Pro Tyr Ser Gln Ala Pro Ser Gly Phe Lys Tyr Trp Leu
    1040                1045                1050

Lys Glu Arg Gly Ala Ser Leu Gln His Thr Ala Pro Phe Gly Cys
    1055                1060                1065

Gln Ile Ala Thr Asn Pro Val Arg Ala Val Asn Cys Ala Val Gly
    1070                1075                1080

Asn Met Pro Ile Ser Ile Asp Ile Pro Glu Ala Ala Phe Thr Arg
    1085                1090                1095

Val Val Asp Ala Pro Ser Leu Thr Asp Met Ser Cys Glu Val Pro
    1100                1105                1110

Ala Cys Thr His Ser Ser Asp Phe Gly Gly Val Ala Ile Ile Lys
    1115                1120                1125

Tyr Ala Ala Ser Lys Lys Gly Lys Cys Ala Val His Ser Met Thr
    1130                1135                1140

Asn Ala Val Thr Ile Arg Glu Ala Glu Ile Glu Val Glu Gly Asn
    1145                1150                1155

Ser Gln Leu Gln Ile Ser Phe Ser Thr Ala Leu Ala Ser Ala Glu
    1160                1165                1170

Phe Arg Val Gln Val Cys Ser Thr Gln Val His Cys Ala Ala Glu
    1175                1180                1185

Cys His Pro Pro Lys Asp His Ile Val Asn Tyr Pro Ala Ser His
    1190                1195                1200

Thr Thr Leu Gly Val Gln Asp Ile Ser Ala Thr Ala Met Ser Trp
    1205                1210                1215

Val Gln Lys Ile Thr Gly Gly Val Gly Leu Val Val Ala Val Ala
    1220                1225                1230

Ala Leu Ile Leu Ile Val Val Leu Cys Val Ser Phe Ser Arg His
    1235                1240                1245

<210> SEQ ID NO 2
<211> LENGTH: 1248
<212> TYPE: PRT
<213> ORGANISM: Chikungunya virus

<400> SEQUENCE: 2

Met Glu Phe Ile Pro Thr Gln Thr Phe Tyr Asn Arg Arg Tyr Gln Pro
1               5                   10                  15

Arg Pro Trp Ala Pro Arg Pro Thr Ile Gln Val Ile Arg Pro Arg Pro
            20                  25                  30
```

```
Arg Pro Gln Arg Gln Ala Gly Gln Leu Ala Gln Leu Ile Ser Ala Val
        35                  40                  45

Asn Lys Leu Thr Met Arg Ala Val Pro Gln Gln Lys Pro Arg Arg Asn
 50                  55                  60

Arg Lys Asn Lys Lys Gln Arg Gln Lys Gln Ala Pro Gln Asn Asp
 65                  70                  75                  80

Pro Lys Gln Lys Gln Pro Gln Lys Lys Pro Ala Gln Lys Lys
                     85                  90                  95

Lys Lys Pro Gly Arg Arg Glu Arg Met Cys Met Lys Ile Glu Asn Asp
                100                 105                 110

Cys Ile Phe Glu Val Lys His Glu Gly Lys Val Met Gly Tyr Ala Cys
            115                 120                 125

Leu Val Gly Asp Lys Val Met Lys Pro Ala His Val Lys Gly Thr Ile
            130                 135                 140

Asp Asn Ala Asp Leu Ala Lys Leu Ala Phe Lys Arg Ser Ser Lys Tyr
145                 150                 155                 160

Asp Leu Glu Cys Ala Gln Ile Pro Val His Met Lys Ser Asp Ala Ser
                165                 170                 175

Lys Phe Thr His Glu Lys Pro Glu Gly Tyr Tyr Asn Trp His His Gly
            180                 185                 190

Ala Val Gln Tyr Ser Gly Gly Arg Phe Thr Ile Pro Thr Gly Ala Gly
            195                 200                 205

Lys Pro Gly Asp Ser Gly Arg Pro Ile Phe Asp Asn Lys Gly Arg Val
            210                 215                 220

Val Ala Ile Val Leu Gly Gly Ala Asn Glu Gly Ala Arg Thr Ala Leu
225                 230                 235                 240

Ser Val Val Thr Trp Asn Lys Asp Ile Val Thr Lys Ile Thr Pro Glu
                245                 250                 255

Gly Ala Glu Glu Trp Ser Leu Ala Leu Pro Val Leu Cys Leu Leu Ala
                260                 265                 270

Asn Thr Thr Phe Pro Cys Ser Gln Pro Pro Cys Thr Pro Cys Cys Tyr
            275                 280                 285

Glu Lys Glu Pro Glu Ser Thr Leu Arg Met Leu Glu Asp Asn Val Met
            290                 295                 300

Arg Pro Gly Tyr Tyr Gln Leu Leu Lys Ala Ser Leu Thr Cys Ser Pro
305                 310                 315                 320

His Arg Gln Arg Arg Ser Thr Lys Asp Asn Phe Asn Val Tyr Lys Ala
                325                 330                 335

Thr Arg Pro Tyr Leu Ala His Cys Pro Asp Cys Gly Glu Gly His Ser
                340                 345                 350

Cys His Ser Pro Ile Ala Leu Glu Arg Ile Arg Asn Glu Ala Thr Asp
            355                 360                 365

Gly Thr Leu Lys Ile Gln Val Ser Leu Gln Ile Gly Ile Lys Thr Asp
            370                 375                 380

Asp Ser His Asp Trp Thr Lys Leu Arg Tyr Met Asp Ser His Thr Pro
385                 390                 395                 400

Ala Asp Ala Glu Arg Ala Gly Leu Leu Val Arg Thr Ser Ala Pro Cys
                405                 410                 415

Thr Ile Thr Gly Thr Met Gly His Phe Ile Leu Ala Arg Cys Pro Lys
            420                 425                 430

Gly Glu Thr Leu Thr Val Gly Phe Thr Asp Ser Arg Lys Ile Ser His
            435                 440                 445
```

-continued

```
Thr Cys Thr His Pro Phe His His Glu Pro Pro Val Ile Gly Arg Glu
    450                 455                 460

Arg Phe His Ser Arg Pro Gln His Gly Lys Glu Leu Pro Cys Ser Thr
465                 470                 475                 480

Tyr Val Gln Ser Thr Ala Ala Thr Ala Glu Glu Ile Glu Val His Met
                485                 490                 495

Pro Pro Asp Thr Pro Asp Arg Thr Leu Met Thr Gln Gln Ser Gly Asn
            500                 505                 510

Val Lys Ile Thr Val Asn Gly Gln Thr Val Arg Tyr Lys Cys Asn Cys
        515                 520                 525

Gly Gly Ser Asn Glu Gly Leu Thr Thr Thr Asp Lys Val Ile Asn Asn
530                 535                 540

Cys Lys Ile Asp Gln Cys His Ala Ala Val Thr Asn His Lys Asn Trp
545                 550                 555                 560

Gln Tyr Asn Ser Pro Leu Val Pro Arg Asn Ala Glu Leu Gly Asp Arg
                565                 570                 575

Lys Gly Lys Ile His Ile Pro Phe Pro Leu Ala Asn Val Thr Cys Arg
            580                 585                 590

Val Pro Lys Ala Arg Asn Pro Thr Val Thr Tyr Gly Lys Asn Gln Val
        595                 600                 605

Thr Met Leu Leu Tyr Pro Asp His Pro Thr Leu Leu Ser Tyr Arg Asn
610                 615                 620

Met Gly Gln Glu Pro Asn Tyr His Glu Glu Trp Val Thr His Lys Lys
625                 630                 635                 640

Glu Val Thr Leu Thr Val Pro Thr Glu Gly Leu Glu Val Thr Trp Gly
                645                 650                 655

Asn Asn Glu Pro Tyr Lys Tyr Trp Pro Gln Met Ser Thr Asn Gly Thr
            660                 665                 670

Ala His Gly His Pro His Glu Ile Ile Leu Tyr Tyr Tyr Glu Leu Tyr
        675                 680                 685

Pro Thr Met Thr Val Val Ile Val Ser Val Ala Ser Phe Val Leu Leu
690                 695                 700

Ser Met Val Gly Thr Ala Val Gly Met Cys Val Cys Ala Arg Arg Arg
705                 710                 715                 720

Cys Ile Thr Pro Tyr Glu Leu Thr Pro Gly Ala Thr Val Pro Phe Leu
                725                 730                 735

Leu Ser Leu Leu Cys Cys Val Arg Thr Thr Lys Ala Ala Thr Tyr Tyr
            740                 745                 750

Glu Ala Ala Ala Tyr Leu Trp Asn Glu Gln Gln Pro Leu Phe Trp Leu
        755                 760                 765

Gln Ala Leu Ile Pro Leu Ala Ala Leu Ile Val Leu Cys Asn Cys Leu
770                 775                 780

Lys Leu Leu Pro Cys Cys Cys Lys Thr Leu Ala Phe Leu Ala Val Met
785                 790                 795                 800

Ser Ile Gly Ala His Thr Val Ser Ala Tyr Glu His Val Thr Val Ile
                805                 810                 815

Pro Asn Thr Val Gly Val Pro Tyr Lys Thr Leu Val Asn Arg Pro Gly
            820                 825                 830

Tyr Ser Pro Met Val Leu Glu Met Glu Leu Gln Ser Val Thr Leu Glu
        835                 840                 845

Pro Thr Leu Ser Leu Asp Tyr Ile Thr Cys Glu Tyr Lys Thr Val Ile
850                 855                 860

Pro Ser Pro Tyr Val Lys Cys Cys Gly Thr Ala Glu Cys Lys Asp Lys
```

```
                    865                 870                 875                 880
Ser Leu Pro Asp Tyr Ser Cys Lys Val Phe Thr Gly Val Tyr Pro Phe
                885                 890                 895
Met Trp Gly Gly Ala Tyr Cys Phe Cys Asp Ala Glu Asn Thr Gln Leu
                900                 905                 910
Ser Glu Ala His Val Glu Lys Ser Glu Ser Cys Lys Thr Glu Phe Ala
                915                 920                 925
Ser Ala Tyr Arg Ala His Thr Ala Ser Ala Ser Ala Lys Leu Arg Val
                930                 935                 940
Leu Tyr Gln Gly Asn Asn Ile Thr Val Ala Ala Tyr Ala Asn Gly Asp
945                 950                 955                 960
His Ala Val Thr Val Lys Asp Ala Lys Phe Val Val Gly Pro Met Ser
                965                 970                 975
Ser Ala Trp Thr Pro Phe Asp Asn Lys Ile Val Val Tyr Lys Gly Asp
                980                 985                 990
Val Tyr Asn Met Asp Tyr Pro Pro Phe Gly Ala Gly Arg Pro Gly Gln
                995                 1000                1005
Phe Gly Asp Ile Gln Ser Arg Thr Pro Glu Ser Lys Asp Val Tyr
            1010                1015                1020
Ala Asn Thr Gln Leu Val Leu Gln Arg Pro Ala Ala Gly Thr Val
            1025                1030                1035
His Val Pro Tyr Ser Gln Ala Pro Ser Gly Phe Lys Tyr Trp Leu
            1040                1045                1050
Lys Glu Arg Gly Ala Ser Leu Gln His Thr Ala Pro Phe Gly Cys
            1055                1060                1065
Gln Ile Ala Thr Asn Pro Val Arg Ala Val Asn Cys Ala Val Gly
            1070                1075                1080
Asn Ile Pro Ile Ser Ile Asp Ile Pro Asp Ala Ala Phe Thr Arg
            1085                1090                1095
Val Val Asp Ala Pro Ser Val Thr Asp Met Ser Cys Glu Val Pro
            1100                1105                1110
Ala Cys Thr His Ser Ser Asp Phe Gly Gly Val Ala Ile Ile Lys
            1115                1120                1125
Tyr Thr Ala Ser Lys Lys Gly Lys Cys Ala Val His Ser Met Thr
            1130                1135                1140
Asn Ala Val Thr Ile Arg Glu Ala Asp Val Glu Val Glu Gly Asn
            1145                1150                1155
Ser Gln Leu Gln Ile Ser Phe Ser Thr Ala Leu Ala Ser Ala Glu
            1160                1165                1170
Phe Arg Val Gln Val Cys Ser Thr Gln Val His Cys Ala Ala Ala
            1175                1180                1185
Cys His Pro Pro Lys Asp His Ile Val Asn Tyr Pro Ala Ser His
            1190                1195                1200
Thr Thr Leu Gly Val Gln Asp Ile Ser Thr Thr Ala Met Ser Trp
            1205                1210                1215
Val Gln Lys Ile Thr Gly Gly Val Gly Leu Ile Val Ala Val Ala
            1220                1225                1230
Ala Leu Ile Leu Ile Val Val Leu Cys Val Ser Phe Ser Arg His
            1235                1240                1245

<210> SEQ ID NO 3
<211> LENGTH: 1255
<212> TYPE: PRT
<213> ORGANISM: Venesuelan equine encephalitis virus
```

<400> SEQUENCE: 3

```
Met Phe Pro Phe Gln Pro Met Tyr Pro Met Gln Pro Met Pro Tyr Arg
1               5                   10                  15

Asn Pro Phe Ala Ala Pro Arg Arg Pro Trp Phe Pro Arg Thr Asp Pro
                20                  25                  30

Phe Leu Ala Met Gln Val Gln Glu Leu Thr Arg Ser Met Ala Asn Leu
                35                  40                  45

Thr Phe Lys Gln Arg Arg Asp Ala Pro Pro Glu Gly Pro Ser Ala Ala
            50                  55                  60

Lys Pro Lys Lys Glu Ala Ser Gln Lys Gln Lys Gly Gly Gln Gly
65                  70                  75                  80

Lys Lys Lys Lys Asn Gln Gly Lys Lys Ala Lys Thr Gly Pro Pro
                85                  90                  95

Asn Pro Lys Ala Gln Asn Gly Asn Lys Lys Thr Asn Lys Lys Pro
                100                 105                 110

Gly Lys Arg Gln Arg Met Val Met Lys Leu Glu Ser Asp Lys Thr Phe
                115                 120                 125

Pro Ile Met Leu Glu Gly Lys Ile Asn Gly Tyr Ala Cys Val Val Gly
        130                 135                 140

Gly Lys Leu Phe Arg Pro Met His Val Glu Gly Lys Ile Asp Asn Asp
145                 150                 155                 160

Val Leu Ala Ala Leu Lys Thr Lys Lys Ala Ser Lys Tyr Asp Leu Glu
                165                 170                 175

Tyr Ala Asp Val Pro Gln Asn Met Arg Ala Asp Thr Phe Lys Tyr Thr
                180                 185                 190

His Glu Lys Pro Gln Gly Tyr Tyr Ser Trp His His Gly Ala Val Gln
                195                 200                 205

Tyr Glu Asn Gly Arg Phe Thr Val Pro Lys Gly Val Gly Ala Lys Gly
        210                 215                 220

Asp Ser Gly Arg Pro Ile Leu Asp Asn Gln Gly Arg Val Val Ala Ile
225                 230                 235                 240

Val Leu Gly Gly Val Asn Glu Gly Ser Arg Thr Ala Leu Ser Val Val
                245                 250                 255

Met Trp Asn Glu Lys Gly Val Thr Val Lys Tyr Thr Pro Glu Asn Cys
                260                 265                 270

Glu Gln Trp Ser Leu Val Thr Thr Met Cys Leu Leu Ala Asn Val Thr
                275                 280                 285

Phe Pro Cys Ala Gln Pro Pro Ile Cys Tyr Asp Arg Lys Pro Ala Glu
                290                 295                 300

Thr Leu Ala Met Leu Ser Val Asn Val Asp Asn Pro Gly Tyr Asp Glu
305                 310                 315                 320

Leu Leu Glu Ala Ala Val Lys Cys Pro Gly Arg Lys Arg Arg Ser Thr
                325                 330                 335

Glu Glu Leu Phe Asn Glu Tyr Lys Leu Thr Arg Pro Tyr Met Ala Arg
                340                 345                 350

Cys Ile Arg Cys Ala Val Gly Ser Cys His Ser Pro Ile Ala Ile Glu
            355                 360                 365

Ala Val Lys Ser Asp Gly His Asp Gly Tyr Val Arg Leu Gln Thr Ser
            370                 375                 380

Ser Gln Tyr Gly Leu Asp Ser Ser Gly Asn Leu Lys Gly Arg Thr Met
385                 390                 395                 400

Arg Tyr Asp Met His Gly Thr Ile Lys Glu Ile Pro Leu His Gln Val
```

-continued

```
              405                 410                 415
Ser Leu Tyr Thr Ser Arg Pro Cys His Ile Val Asp Gly His Gly Tyr
            420                 425                 430

Phe Leu Leu Ala Arg Cys Pro Ala Gly Asp Ser Ile Thr Met Glu Phe
            435                 440                 445

Lys Lys Asp Ser Val Arg His Ser Cys Ser Val Pro Tyr Glu Val Lys
            450                 455                 460

Phe Asn Pro Val Gly Arg Glu Leu Tyr Thr His Pro Pro Glu His Gly
465                 470                 475                 480

Val Glu Gln Ala Cys Gln Val Tyr Ala His Asp Ala Gln Asn Arg Gly
                485                 490                 495

Ala Tyr Val Glu Met His Leu Pro Gly Ser Glu Val Asp Ser Ser Leu
            500                 505                 510

Val Ser Leu Ser Gly Ser Ser Val Thr Val Thr Pro Pro Asp Gly Thr
            515                 520                 525

Ser Ala Leu Val Glu Cys Glu Cys Gly Gly Thr Lys Ile Ser Glu Thr
            530                 535                 540

Ile Asn Lys Thr Lys Gln Phe Ser Gln Cys Thr Lys Lys Glu Gln Cys
545                 550                 555                 560

Arg Ala Tyr Arg Leu Gln Asn Asp Lys Trp Val Tyr Asn Ser Asp Lys
                565                 570                 575

Leu Pro Lys Ala Ala Gly Ala Thr Leu Lys Gly Lys Leu His Val Pro
            580                 585                 590

Phe Leu Leu Ala Asp Gly Lys Cys Thr Val Pro Leu Ala Pro Glu Pro
            595                 600                 605

Met Ile Thr Phe Gly Phe Arg Ser Val Ser Leu Lys Leu His Pro Lys
            610                 615                 620

Asn Pro Thr Tyr Leu Ile Thr Arg Gln Leu Ala Asp Glu Pro His Tyr
625                 630                 635                 640

Thr His Glu Leu Ile Ser Glu Pro Ala Val Arg Asn Phe Thr Val Thr
                645                 650                 655

Glu Lys Gly Trp Glu Phe Val Trp Gly Asn His Pro Pro Lys Arg Phe
            660                 665                 670

Trp Ala Gln Glu Thr Ala Pro Gly Asn Pro His Gly Leu Pro His Glu
            675                 680                 685

Val Ile Thr His Tyr Tyr His Arg Tyr Pro Met Ser Thr Ile Leu Gly
            690                 695                 700

Leu Ser Ile Cys Ala Ala Ile Ala Thr Val Ser Val Ala Ala Ser Thr
705                 710                 715                 720

Trp Leu Phe Cys Arg Ser Arg Val Ala Cys Leu Thr Pro Tyr Arg Leu
                725                 730                 735

Thr Pro Asn Ala Arg Ile Pro Phe Cys Leu Ala Val Leu Cys Cys Ala
            740                 745                 750

Arg Thr Ala Arg Ala Glu Thr Thr Trp Glu Ser Leu Asp His Leu Trp
            755                 760                 765

Asn Asn Asn Gln Gln Met Phe Trp Ile Gln Leu Leu Ile Pro Leu Ala
            770                 775                 780

Ala Leu Ile Val Val Thr Arg Leu Leu Arg Cys Val Cys Cys Val Val
785                 790                 795                 800

Pro Phe Leu Val Met Ala Gly Ala Ala Gly Ala Gly Ala Tyr Glu His
                805                 810                 815

Ala Thr Thr Met Pro Ser Gln Ala Gly Ile Ser Tyr Asn Thr Ile Val
            820                 825                 830
```

```
Asn Arg Ala Gly Tyr Ala Pro Leu Pro Ile Ser Ile Thr Pro Thr Lys
        835                 840                 845

Ile Lys Leu Ile Pro Thr Val Asn Leu Glu Tyr Val Thr Cys His Tyr
850                 855                 860

Lys Thr Gly Met Asp Ser Pro Ala Ile Lys Cys Cys Gly Ser Gln Glu
865                 870                 875                 880

Cys Thr Pro Thr Tyr Arg Pro Asp Glu Gln Cys Lys Val Phe Thr Gly
                885                 890                 895

Val Tyr Pro Phe Met Trp Gly Gly Ala Tyr Cys Phe Cys Asp Thr Glu
                900                 905                 910

Asn Thr Gln Val Ser Lys Ala Tyr Val Met Lys Ser Asp Asp Cys Leu
        915                 920                 925

Ala Asp His Ala Glu Ala Tyr Lys Ala His Thr Ala Ser Val Gln Ala
930                 935                 940

Phe Leu Asn Ile Thr Val Gly Glu His Ser Ile Val Thr Thr Val Tyr
945                 950                 955                 960

Val Asn Gly Glu Thr Pro Val Asn Phe Asn Gly Val Lys Ile Thr Ala
                965                 970                 975

Gly Pro Leu Ser Thr Ala Trp Thr Pro Phe Asp Arg Lys Ile Val Gln
                980                 985                 990

Tyr Ala Gly Glu Ile Tyr Asn Tyr Asp Phe Pro Glu Tyr Gly Ala Gly
                995                 1000                1005

Gln Pro Gly Ala Phe Gly Asp Ile Gln Ser Arg Thr Val Ser Ser
    1010                1015                1020

Ser Asp Leu Tyr Ala Asn Thr Asn Leu Val Leu Gln Arg Pro Lys
    1025                1030                1035

Ala Gly Ala Ile His Val Pro Tyr Thr Gln Ala Pro Ser Gly Phe
    1040                1045                1050

Glu Gln Trp Lys Lys Asp Lys Ala Pro Ser Leu Lys Phe Thr Ala
    1055                1060                1065

Pro Phe Gly Cys Glu Ile Tyr Thr Asn Pro Ile Arg Ala Glu Asn
    1070                1075                1080

Cys Ala Val Gly Ser Ile Pro Leu Ala Phe Asp Ile Pro Asp Ala
    1085                1090                1095

Leu Phe Thr Arg Val Ser Glu Thr Pro Thr Leu Ser Ala Ala Glu
    1100                1105                1110

Cys Thr Leu Asn Glu Cys Val Tyr Ser Ser Asp Phe Gly Gly Ile
    1115                1120                1125

Ala Thr Val Lys Tyr Ser Ala Ser Lys Ser Gly Lys Cys Ala Val
    1130                1135                1140

His Val Pro Ser Gly Thr Ala Thr Leu Lys Glu Ala Ala Val Glu
    1145                1150                1155

Leu Thr Glu Gln Gly Ser Ala Thr Ile His Phe Ser Thr Ala Asn
    1160                1165                1170

Ile His Pro Glu Phe Arg Leu Gln Ile Cys Thr Ser Tyr Val Thr
    1175                1180                1185

Cys Lys Gly Asp Cys His Pro Pro Lys Asp His Ile Val Thr His
    1190                1195                1200

Pro Gln Tyr His Ala Gln Thr Phe Thr Ala Ala Val Ser Lys Thr
    1205                1210                1215

Ala Trp Thr Trp Leu Thr Ser Leu Leu Gly Gly Ser Ala Val Ile
    1220                1225                1230
```

```
Ile Ile  Ile Gly Leu Val Leu  Ala Thr Ile Val Ala  Met Tyr Val
    1235             1240              1245

Leu Thr  Asn Gln Lys His Asn
    1250             1255

<210> SEQ ID NO 4
<211> LENGTH: 18
<212> TYPE: PRT
<213> ORGANISM: Artificial Sequence
<220> FEATURE:
<223> OTHER INFORMATION: Synthetic peptide

<400> SEQUENCE: 4

Leu Asn Trp Tyr Arg Met Ser Pro Ser Asn Gln Thr Asp Lys Leu Ala
1               5                   10                  15

Ala Phe

<210> SEQ ID NO 5
<211> LENGTH: 20
<212> TYPE: PRT
<213> ORGANISM: Artificial Sequence
<220> FEATURE:
<223> OTHER INFORMATION: Synthetic peptide

<400> SEQUENCE: 5

Met Leu Asn Trp Tyr Arg Met Ser Pro Ser Asn Gln Thr Asp Lys Leu
1               5                   10                  15

Ala Ala Phe Ser
            20

<210> SEQ ID NO 6
<211> LENGTH: 20
<212> TYPE: PRT
<213> ORGANISM: Artificial Sequence
<220> FEATURE:
<223> OTHER INFORMATION: Synthetic peptide

<400> SEQUENCE: 6

Val Leu Asn Trp Tyr Arg Met Ser Pro Ser Asn Gln Thr Asp Lys Leu
1               5                   10                  15

Ala Ala Phe Pro
            20

<210> SEQ ID NO 7
<211> LENGTH: 14
<212> TYPE: PRT
<213> ORGANISM: Artificial Sequence
<220> FEATURE:
<223> OTHER INFORMATION: Synthetic peptide

<400> SEQUENCE: 7

Gly Ala Ile Ser Leu His Pro Lys Ala Lys Ile Glu Glu Ser
1               5                   10

<210> SEQ ID NO 8
<211> LENGTH: 15
<212> TYPE: PRT
<213> ORGANISM: Artificial Sequence
<220> FEATURE:
<223> OTHER INFORMATION: Synthetic peptide

<400> SEQUENCE: 8

Cys Gly Ala Ile Ser Leu His Pro Lys Ala Lys Ile Glu Glu Cys
1               5                   10                  15
```

<210> SEQ ID NO 9
<211> LENGTH: 19
<212> TYPE: PRT
<213> ORGANISM: Artificial Sequence
<220> FEATURE:
<223> OTHER INFORMATION: Synthetic peptide

<400> SEQUENCE: 9

Val Leu Asn Trp Tyr Arg Met Ser Pro Ser Asn Gln Thr Asp Lys Leu
1               5                   10                  15

Ala Ala Phe

<210> SEQ ID NO 10
<211> LENGTH: 14
<212> TYPE: PRT
<213> ORGANISM: Artificial Sequence
<220> FEATURE:
<223> OTHER INFORMATION: Synthetic peptide

<400> SEQUENCE: 10

Gly Ala Ile Ser Leu Ala Pro Lys Ala Gln Ile Lys Glu Ser
1               5                   10

<210> SEQ ID NO 11
<211> LENGTH: 31
<212> TYPE: PRT
<213> ORGANISM: Artificial Sequence
<220> FEATURE:
<223> OTHER INFORMATION: Synthetic peptide

<400> SEQUENCE: 11

Arg Asn Asp Ser Gly Thr Tyr Leu Cys Gly Ala Ile Ser Leu Ala Pro
1               5                   10                  15

Lys Ala Gln Ile Lys Glu Ser Leu Arg Ala Glu Leu Arg Val Thr
            20                  25                  30

<210> SEQ ID NO 12
<211> LENGTH: 31
<212> TYPE: PRT
<213> ORGANISM: Artificial Sequence
<220> FEATURE:
<223> OTHER INFORMATION: Synthetic peptide

<400> SEQUENCE: 12

Arg Asn Asp Ser Gly Ile Tyr Leu Cys Gly Ala Ile Ser Leu His Pro
1               5                   10                  15

Lys Ala Lys Ile Glu Glu Ser Pro Gly Ala Glu Leu Val Val Thr
            20                  25                  30

<210> SEQ ID NO 13
<211> LENGTH: 11
<212> TYPE: PRT
<213> ORGANISM: Artificial Sequence
<220> FEATURE:
<223> OTHER INFORMATION: Synthetic peptide

<400> SEQUENCE: 13

Cys Ile Ile Ser Tyr Gly Gly Ala Asp Tyr Cys
1               5                   10

<210> SEQ ID NO 14
<211> LENGTH: 11
<212> TYPE: PRT
<213> ORGANISM: Artificial Sequence
<220> FEATURE:

```
<223> OTHER INFORMATION: Synthetic peptide

<400> SEQUENCE: 14

Cys Met Ile Ser Tyr Gly Gly Ala Asp Tyr Cys
1               5                   10

<210> SEQ ID NO 15
<211> LENGTH: 26
<212> TYPE: PRT
<213> ORGANISM: Artificial Sequence
<220> FEATURE:
<223> OTHER INFORMATION: Synthetic peptide

<400> SEQUENCE: 15

Leu Gln Asp Ala Gly Val Tyr Arg Cys Met Ile Ser Tyr Gly Gly Ala
1               5                   10                  15

Asp Tyr Lys Arg Ile Thr Val Lys Val Asn
            20                  25

<210> SEQ ID NO 16
<211> LENGTH: 26
<212> TYPE: PRT
<213> ORGANISM: Artificial Sequence
<220> FEATURE:
<223> OTHER INFORMATION: Synthetic peptide

<400> SEQUENCE: 16

Leu Gln Asp Ala Gly Val Tyr Arg Ala Met Ile Ser Tyr Gly Gly Ala
1               5                   10                  15

Asp Tyr Lys Arg Ile Thr Val Lys Val Asn
            20                  25

<210> SEQ ID NO 17
<211> LENGTH: 21
<212> TYPE: PRT
<213> ORGANISM: Artificial Sequence
<220> FEATURE:
<223> OTHER INFORMATION: Synthetic peptide

<400> SEQUENCE: 17

Asp Leu Ala Ala Leu Ile Val Tyr Trp Glu Met Glu Asp Lys Asn Ile
1               5                   10                  15

Ile Gln Phe Val His
            20

<210> SEQ ID NO 18
<211> LENGTH: 23
<212> TYPE: PRT
<213> ORGANISM: Artificial Sequence
<220> FEATURE:
<223> OTHER INFORMATION: Synthetic peptide

<400> SEQUENCE: 18

Asp Leu Ala Ala Leu Ile Val Tyr Trp Glu Met Glu Asp Lys Asn Ile
1               5                   10                  15

Ile Gln Phe Val His Gly Gly
            20

<210> SEQ ID NO 19
<211> LENGTH: 27
<212> TYPE: PRT
<213> ORGANISM: Artificial Sequence
<220> FEATURE:
<223> OTHER INFORMATION: Synthetic peptide
```

```
<400> SEQUENCE: 19

Phe Thr Val Thr Val Pro Lys Asp Leu Tyr Val Val Glu Tyr Gly Ser
1               5                   10                  15

Asn Met Thr Ile Glu Cys Lys Phe Pro Val Glu
            20                  25

<210> SEQ ID NO 20
<211> LENGTH: 26
<212> TYPE: PRT
<213> ORGANISM: Artificial Sequence
<220> FEATURE:
<223> OTHER INFORMATION: Synthetic peptide

<400> SEQUENCE: 20

Leu Gln Asp Ala Gly Val Tyr Cys Cys Ile Ile Ser Tyr Gly Gly Ala
1               5                   10                  15

Asp Tyr Lys Arg Ile Thr Leu Lys Val Asn
            20                  25

<210> SEQ ID NO 21
<211> LENGTH: 26
<212> TYPE: PRT
<213> ORGANISM: Artificial Sequence
<220> FEATURE:
<223> OTHER INFORMATION: Synthetic peptide

<400> SEQUENCE: 21

Leu Gln Asp Ala Gly Val Tyr Ala Ala Ile Ile Ser Tyr Gly Gly Ala
1               5                   10                  15

Asp Tyr Lys Arg Ile Thr Leu Lys Val Asn
            20                  25

<210> SEQ ID NO 22
<211> LENGTH: 21
<212> TYPE: PRT
<213> ORGANISM: Artificial Sequence
<220> FEATURE:
<223> OTHER INFORMATION: Synthetic peptide

<400> SEQUENCE: 22

Asp Leu Leu Ala Leu Val Val Tyr Trp Glu Lys Glu Asp Glu Gln Val
1               5                   10                  15

Ile Gln Phe Val Ala
            20

<210> SEQ ID NO 23
<211> LENGTH: 23
<212> TYPE: PRT
<213> ORGANISM: Artificial Sequence
<220> FEATURE:
<223> OTHER INFORMATION: Synthetic peptide

<400> SEQUENCE: 23

Asp Leu Leu Ala Leu Val Val Tyr Trp Glu Lys Glu Asp Glu Gln Val
1               5                   10                  15

Ile Gln Phe Val Ala Gly Gly
            20

<210> SEQ ID NO 24
<211> LENGTH: 27
<212> TYPE: PRT
<213> ORGANISM: Artificial Sequence
<220> FEATURE:
<223> OTHER INFORMATION: Synthetic peptide
```

<400> SEQUENCE: 24

Phe Thr Ile Thr Ala Pro Lys Asp Leu Tyr Val Val Glu Tyr Gly Ser
1               5                   10                  15

Asn Val Thr Met Glu Cys Arg Phe Pro Val Glu
            20                  25

<210> SEQ ID NO 25
<211> LENGTH: 8410
<212> TYPE: DNA
<213> ORGANISM: Artificial Sequence
<220> FEATURE:
<223> OTHER INFORMATION: Synthetic polynucleotide

<400> SEQUENCE: 25

```
gaattcccat tgcatacgtt gtatccatat cataatatgt acatttatat tggctcatgt      60
ccaacattac cgccatgttg acattgatta ttgactagtt attaatagta atcaattacg     120
gggtcattag ttcatagccc atatatggag ttccgcgtta cataacttac ggtaaatggc     180
ccgcctggct gaccgcccaa cgacccccgc ccattgacgt caataatgac gtatgttccc     240
atagtaacgc caatagggac tttccattga cgtcaatggg tggagtattt acggtaaact     300
gcccacttgg cagtacatca agtgtatcat atgccaagta cgccccctat tgacgtcaat     360
gacggtaaat ggcccgcctg gcattatgcc cagtacatga ccttatggga ctttcctact     420
tggcagtaca tctacgtatt agtcatcgct attaccatgg tgatgcggtt ttggcagtac     480
atcaatgggc gtggatagcg gtttgactca cggggatttc caagtctcca ccccattgac     540
gtcaatggga gtttgttttg gcaccaaaat caacgggact ttccaaaatg tcgtaacaac     600
tccgccccat tgacgcaaat gggcggtagg cgtgtacggt gggaggtcta taagcagag     660
gctcgtttag tgaaccgtca gatcgcctgg agacgccatc cacgctgttt tgacctccat     720
agaagacacc gggaccgatc cagcctccgt taacggtgga gggcagtgta gtctgagcag     780
tactcgttgc tgccgcgcgc gccaccagac ataatagctg acagactaac agactgttcc     840
tttccatggg tcttttctgc agtcaccgtc gtcgacacgt gtgatcagat atcgcggccg     900
ccaccatgga gttcatcccg acgcaaactt tctataacag aaggtaccaa ccccgaccct     960
gggccccacg ccctacaatt caagtaatta gacctagacc acgtccacag aggcaggctg    1020
ggcaactcgc ccagctgatc tccgcagtca acaaattgac catgcgcgcg gtacctcaac    1080
agaagcctcg cagaaatcgg aaaaacaaga agcaaaggca agaagcag gcgccgcaaa    1140
acgacccaaa gcaaaagaag caaccaccac aaaagaagcc ggctcaaaag aagaagaaac    1200
caggccgtag ggagagaatg tgcatgaaaa ttgaaaatga ttgcatcttc gaagtcaagc    1260
atgaaggcaa agtgatgggc tacgcatgcc tggtggggga taaagtaatg aaaccagcac    1320
atgtgaaggg aactatcgac aatgccgatc tggctaaact ggcctttaag cggtcgtcta    1380
aatacgatct tgaatgtgca cagataccgg tgcacatgaa gtctgatgcc tcgaagttta    1440
cccacgagaa acccgagggg tactataact ggcatcacgg agcagtgcag tattcaggag    1500
gccggttcac tatcccgacg ggtgcaggca agcggggaga cagcggcaga ccgatcttcg    1560
acaacaaagg acgggtggtg gccatcgtcc taggaggggc caacgaaggt gcccgcacgg    1620
ccctctccgt ggtgacgtgg aacaaagaca tcgtcacaaa aattaccccct gagggagccg    1680
aagagtggag cctcgccctc ccggtcttgt gcctgttggc aaacactaca ttcccctgct    1740
ctcagccgcc ttgcacaccc tgctgctacg aaaaggaacc ggaaagcacc ttgcgcatgc    1800
```

```
ttgaggacaa cgtgatgaga cccggatact accagctact aaaagcatcg ctgacttgct    1860
ctccccaccg ccaaagacgc agtactaagg acaattttaa tgtctataaa gccacaagac    1920
catatctagc tcattgtcct gactgcggag aagggcattc gtgccacagc cctatcgcat    1980
tggagcgcat cagaaatgaa gcaacggacg gaacgctgaa atccaggtc tctttgcaga     2040
tcgggataaa gacagatgac agccacgatt ggaccaagct gcgctatatg gatagccata    2100
cgccagcgga cgcggagcga gccggattgc ttgtaaggac ttcagcaccg tgcacgatca    2160
ccgggaccat gggacacttt attctcgccc gatgcccgaa aggagagacg ctgacagtgg    2220
gatttacgga cagcagaaag atcagccaca catgcacaca cccgttccat catgaaccac    2280
ctgtgatagg tagggagagg ttccactctc gaccacaaca tggtaaagag ttaccttgca    2340
gcacgtacgt gcagagcacc gctgccactg ctgaggagat agaggtgcat atgcccccag    2400
atactcctga ccgcacgctg atgacgcagc agtctggcaa cgtgaagatc acagttaatg    2460
ggcagacggt gcggtacaag tgcaactgcg gtggctccgg aagtggatcc aacgagggac    2520
tgacaaccac agacaaagtg atcaataact gcaaaattga tcagtgccat gctgcagtca    2580
ctaatcacaa gaattggcaa tacaactccc ctttagtccc gcgcaacgct gaactcgggg    2640
accgtaaagg aaagatccac atcccattcc cattggcaaa cgtgacttgc agagtgccaa    2700
aagcaagaaa ccctacagta acttacggaa aaaccaagt caccatgctg ctgtatcctg     2760
accatccgac actcttgtct taccgtaaca tgggacagga accaaattac cacgaggagt    2820
gggtgacaca caagaaggag gttaccttga ccgtgcctac tgagggtctg gaggtcactt    2880
ggggcaacaa cgaaccatac aagtactggc gcagatgtc tacgaacggt actgctcatg     2940
gtcacccaca tgagataatc ttgtactatt atgagctgta ccccactatg actgtagtca    3000
ttgtgtcggt ggcctcgttc gtgcttctgt cgatggtggg cacagcagtg gaatgtgtg     3060
tgtgcgcacg gcgcagatgc attacaccat atgaattaac accaggagcc actgttccct    3120
tcctgctcag cctgctatgc tgcgtcagaa cgaccaaggc ggccacatat tacgaggctg    3180
cggcatatct atggaacgaa cagcagcccc tgttctggtt gcaggctctt atcccgctgg    3240
ccgccttgat cgtcctgtgc aactgtctga aactcttgcc atgctgctgt aagaccctgg    3300
cttttttagc cgtaatgagc atcggtgccc acactgtgag cgcgtacgaa cacgtaacag    3360
tgatcccgaa cacggtggga gtaccgtata agactcttgt caacagaccg ggttacagcc    3420
ccatggtgtt ggagatggag ctacaatcag tcaccttgga accaacactg tcacttgact    3480
acatcacgtg cgagtacaaa actgtcatcc cctccccgta cgtgaagtgc tgtggtacag    3540
cagagtgcaa ggacaagagc ctaccagact acagctgcaa ggtctttact ggagtctacc    3600
catttatgtg gggcggcgcc tactgctttt gcgacgccga aaatacgcaa ttgagcgagg    3660
cacatgtaga gaaatctgaa tcttgcaaaa cagagtttgc atcggcctac agagcccaca    3720
ccgcatcggc gtcggcgaag ctccgcgtcc tttaccaagg aaacaacatt accgtagctg    3780
cctacgctaa cggtgaccat gccgtcacag taaaggacgc caagtttgtc gtgggcccaa    3840
tgtcctccgc ctggacacct tttgacaaca aaatcgtggt gtacaaaggc gacgtctaca    3900
acatggacta cccaccttt ggcgcaggaa gaccaggaca atttggtgac attcaaagtc     3960
gtacaccgga aagtaaagac gtttatgcca acactcagtt ggtactacag aggccagcag    4020
caggcacggt acatgtacca tactctcagg caccatctgg cttcaagtat tggctgaagg    4080
aacgaggagc atcgctacag cacacggcac cgttcggttg ccagattgcg acaaacccgg    4140
taagagctgt aaattgcgct gtggggaaca taccaatttc catcgacata ccggatgcgg    4200
```

```
cctttactag ggttgtcgat gcaccctctg taacggacat gtcatgcgaa gtaccagcct    4260
gcactcactc ctccgacttt gggggcgtcg ccatcatcaa atacacagct agcaagaaag    4320
gtaaatgtgc agtacattcg atgaccaacg ccgttaccat tcgagaagcc gacgtagaag    4380
tagagcggaa ctcccagctg caaatatcct tctcaacagc cctggcaagc gccgagtttc    4440
gcgtgcaagt gtgctccaca caagtacact gcgcagccgc atgccaccct ccaaaggacc    4500
acatagtcaa ttacccagca tcacacacca cccttggggt ccaggatata tccacaacgg    4560
caatgtcttg ggtgcagaag attacgggag gagtaggatt aattgttgct gttgctgcct    4620
taattttaat tgtggtgcta tgcgtgtcgt ttagcaggca ctaaggatct agatctgctg    4680
tgccttctag ttgccagcca tctgttgttt gcccctcccc cgtgccttcc ttgaccctgg    4740
aaggtgccac tcccactgtc ctttcctaat aaaatgagga aattgcatcg cattgtctga    4800
gtaggtgtca ttctattctg ggggtgggg tggggcagga cagcaagggg gaggattggg     4860
aagacaatag caggcatgct ggggatgcgg tgggctctat gggtacccag gtgctgaaga    4920
attgacccgg ttcctcctgg gccagaaaga agcaggcaca tccccttctc tgtgacacac    4980
cctgtccacg cccctggttc ttagttccag ccccactcat aggacactca tagctcagga    5040
gggctccgcc ttcaatccca cccgctaaag tacttggagc ggtctctccc tccctcatca    5100
gcccaccaaa ccaaacctag cctccaagag tgggaagaaa ttaaagcaag ataggctatt    5160
aagtgcagag ggagagaaaa tgcctccaac atgtgaggaa gtaatgagag aaatcataga    5220
attttaaggc catgatttaa ggccatcatg gcctaagctt gaaaggagat aggatccaag    5280
cttggcgtaa tcatggtcat agctgtttcc tgtgtgaaat tgttatccgc tcacaattcc    5340
acacaacata cgagccggaa gcataaagtg taaagcctgg ggtgcctaat gagtgagcta    5400
actcacatta attgcgttgc gctcactgcc cgctttccag tcgggaaacc tgtcgtgcca    5460
gctgcattaa tgaatcggcc aacgcgcggg gagaggcggt ttgcgtattg ggcgctcttc    5520
cgcttcctcg ctcactgact cgctgcgctc ggtcgttcgg ctgcggcgag cggtatcagc    5580
tcactcaaag gcggtaatac ggttatccac agaatcaggg gataacgcag gaaagaacat    5640
gtgagcaaaa ggccagcaaa aggccaggaa ccgtaaaaag gccgcgttgc tggcgttttt    5700
ccataggctc cgcccccctg acgagcatca caaaaatcga cgctcaagtc agaggtggcg    5760
aaacccgaca ggactataaa gataccaggc gtttccccct ggaagctccc tcgtgcgctc    5820
tcctgttccg accctgccgc ttaccggata cctgtccgcc tttctccctt cgggaagcgt    5880
ggcgctttct catagctcac gctgtaggta tctcagttcg gtgtaggtcg ttcgctccaa    5940
gctgggctgt gtgcacgaac cccccgttca gcccgaccgc tgcgccttat ccggtaacta    6000
tcgtcttgag tccaacccgg taagacacga cttatcgcca ctggcagcag ccactggtaa    6060
caggattagc agagcgaggt atgtaggcgg tgctacagag ttcttgaagt ggtggcctaa    6120
ctacggctac actagaagaa cagtatttgg tatctgcgct ctgctgaagc cagttacctt    6180
cggaaaaaga gttggtagct cttgatccgg caaacaaacc accgctggta gcggtggttt    6240
ttttgtttgc aagcagcaga ttacgcgcag aaaaaaagga tctcaagaag atcctttgat    6300
cttttctacg gggtctgacg ctcagtggaa cgaaaactca cgttaaggga ttttggtcat    6360
gagattatca aaaaggatct tcacctagat ccttttaaat taaaaatgaa gttttaaatc    6420
aatctaaagt atatatgagt aaacttggtc tgacagttac caatgcttaa tcagtgaggc    6480
acctatctca gcgatctgtc tatttcgttc atccatagtt gcctgactcc ccgtcgtgta    6540
```

| | | |
|---|---|---|
| gataactacg atacgggagg gcttaccatc tggccccagt gctgcaatga taccgcgaga | 6600 | |
| accacgctca ccggctccag atttatcagc aataaaccag ccagccggaa gggccgagcg | 6660 | |
| cagaagtggt cctgcaactt tatccgcctc catccagtct attaattgtt gccgggaagc | 6720 | |
| tagagtaagt agttcgccag ttaatagttt gcgcaacgtt gttgccattg ctacaggcat | 6780 | |
| cgtggtgtca cgctcgtcgt ttggtatggc ttcattcagc tccggttccc aacgatcaag | 6840 | |
| gcgagttaca tgatccccca tgttgtgcaa aaaagcggtt agctccttcg gtcctccgat | 6900 | |
| cgttgtcaga agtaagttgg ccgcagtgtt atcactcatg gttatggcag cactgcataa | 6960 | |
| ttctcttact gtcatgccat ccgtaagatg cttttctgtg actggtgagt actcaaccaa | 7020 | |
| gtcattctga aatagtgta tgcggcgacc gagttgctct tgcccggcgt caatacggga | 7080 | |
| taataccgcg ccacatagca gaactttaaa agtgctcatc attggaaaac gttcttcggg | 7140 | |
| gcgaaaactc tcaaggatct taccgctgtt gagatccagt tcgatgtaac ccactcgtgc | 7200 | |
| acccaactga tcttcagcat cttttacttt caccagcgtt tctgggtgag caaaaacagg | 7260 | |
| aaggcaaaat gccgcaaaaa agggaataag ggcgacacgg aaatgttgaa tactcatact | 7320 | |
| cttcctttt caatattatt gaagcattta tcagggttat tgtctcatga gcggatacat | 7380 | |
| atttgaatgt atttagaaaa ataaacaaat aggggttccg cgcacatttc cccgaaaagt | 7440 | |
| gccacctgac gtctaagaaa ccattattat catgacatta acctataaaa ataggcgtat | 7500 | |
| cacgaggccc tttcgggtcg cgcgtttcgg tgatgacggt gaaaacctct gacacatgca | 7560 | |
| gctcccgttg acggtcacag cttgtctgta agcggatgcc gggagcagac aagcccgtca | 7620 | |
| gggcgcgtca gcgggtgttg gcgggtgtcg ggctggctt aactatgcgg catcagagca | 7680 | |
| gattgtactg agagtgcacc ataaaattgt aaacgttaat attttgttaa aattcgcgtt | 7740 | |
| aaattttgt taaatcagct cattttttaa ccaataggcc gaaatcggca aaatccctta | 7800 | |
| taaatcaaaa gaatagcccg agatagggtt gagtgttgtt ccagtttgga acaagagtcc | 7860 | |
| actattaaag aacgtggact ccaacgtcaa agggcgaaaa accgtctatc agggcgatgg | 7920 | |
| cccactacgt gaaccatcac ccaaatcaag ttttttgggg tcgaggtgcc gtaaagcact | 7980 | |
| aaatcggaac cctaaaggga gcccccgatt tagagcttga cggggaaagc cggcgaacgt | 8040 | |
| ggcgagaaag gaagggaaga agcgaaagg agcgggcgct agggcgctgg caagtgtagc | 8100 | |
| ggtcacgctg cgcgtaacca ccacacccgc cgcgcttaat gcgccgctac agggcgcgta | 8160 | |
| ctatggttgc tttgacgtat gcggtgtgaa ataccgcaca gatgcgtaag gagaaaatac | 8220 | |
| cgcatcaggc gccattcgcc attcaggctg cgcaactgtt gggaagggcg atcggtgcgg | 8280 | |
| gcctcttcgc tattacgcca gctggcgaaa gggggatgtg ctgcaaggcg attaagttgg | 8340 | |
| gtaacgccag ggttttccca gtcacgacgt tgtaaaacga cggccagtga attccatggt | 8400 | |
| ctcaactttc | 8410 | |

<210> SEQ ID NO 26
<211> LENGTH: 8431
<212> TYPE: DNA
<213> ORGANISM: Artificial Sequence
<220> FEATURE:
<223> OTHER INFORMATION: Synthetic polynucleotide

<400> SEQUENCE: 26

| | | |
|---|---|---|
| gaattcccat tgcatacgtt gtatccatat cataatatgt acatttatat tggctcatgt | 60 | |
| ccaacattac cgccatgttg acattgatta ttgactagtt attaatagta atcaattacg | 120 | |
| gggtcattag ttcatagccc atatatggag ttccgcgtta cataacttac ggtaaatggc | 180 | |

```
ccgcctggct gaccgcccaa cgaccccgc ccattgacgt caataatgac gtatgttccc    240
atagtaacgc caatagggac tttccattga cgtcaatggg tggagtattt acggtaaact    300
gcccacttgg cagtacatca agtgtatcat atgccaagta cgccccctat tgacgtcaat    360
gacggtaaat ggcccgcctg gcattatgcc cagtacatga ccttatggga ctttcctact    420
tggcagtaca tctacgtatt agtcatcgct attaccatgg tgatgcggtt ttggcagtac    480
atcaatgggc gtggatagcg gtttgactca cggggatttc caagtctcca ccccattgac    540
gtcaatggga gtttgttttg gcaccaaaat caacgggact ttccaaaatg tcgtaacaac    600
tccgccccat tgacgcaaat gggcggtagg cgtgtacggt gggaggtcta tataagcaga    660
gctcgtttag tgaaccgtca gatcgcctgg agacgccatc cacgctgttt tgacctccat    720
agaagacacc gggaccgatc cagcctccgt taacggtgga gggcagtgta gtctgagcag    780
tactcgttgc tgccgcgcgc gccaccagac ataatagctg acagactaac agactgttcc    840
tttccatggg tcttttctgc agtcaccgtc gtcgacacgt gtgatcagat atcgcggccg    900
ccaccatgtt cccgttccag ccaatgtatc cgatgcagcc aatgccctat cgcaacccgt    960
tcgcggcccc gcgcaggccc tggttcccca gaaccgaccc ttttctggcg atgcaggtgc   1020
aggaattaac ccgctcgatg gctaacctga cgttcaagca acgccgggac gcgccacctg   1080
aggggccatc cgctaataaa ccgaagaagg aggcctcgca aaacagaaa ggggaggcc   1140 aagggaagaa gaagaagaac caagggaaga agaaggctaa gacagggccg cctaatccga   1200
aggcacagaa tggaaacaag aagaagacca acaagaaacc aggcaagaga cagcgcatgg   1260
tcatgaaatt ggaatctgac aagacgttcc caatcatgtt ggaagggaag ataaacggct   1320
acgcttgtgt ggtcggaggg aagttattca ggccgatgca tgtggaaggc aagatcgaca   1380
acgacgttct ggccgcgctt aagacgaaga aagcatccaa atacgatctt gagtatgcag   1440
atgtgccaca gaacatgcgg gccgatacat tcaaatacac ccatgagaaa ccccaaggct   1500
attacagctg gcatcatgga gcagtccaat atgaaaatgg gcgtttcacg gtgccgaaag   1560
gagttggggc caagggagac agcggacgac ccattctgga taaccaggga cgggtggtcg   1620
ctattgtgct gggaggtgtg aatgaaggat ctaggacagc cctttcagtc gtcatgtgga   1680
acgagaaggg agttaccgtg aagtatactc cagagaactg cgagcaatgg tcactagtga   1740
ccaccatgtg tctgctcgcc aatgtgacgt tcccatgtgc tcaaccacca atttgctacg   1800
acagaaaacc agcagagact ttggccatgc tcagcgttaa cgttgacaac ccgggctacg   1860
atgagctgct ggaagcagct gttaagtgcc ccggaaggaa aaggagatcc accgaggagc   1920
tgtttaatga gtataagcta acgcgccctt acatggccag atgcatcaga tgtgcagttg   1980
ggagctgcca tagtccaata gcaatcgagg cagtaaagag cgacgggcac gacggttatg   2040
ttagacttca gacttcctcg cagtatggcc tggattcctc cggcaactta aagggcagga   2100
ccatgcggta tgacatgcac gggaccatta aagagatacc actacatcaa gtgtcactct   2160
atacatctcg cccgtgtcac attgtggatg gcacggtta tttcctgctt gccaggtgcc   2220
cggcagggga ctccatcacc atggaattta gaaaagattc cgtcagacac tcctgctcgg   2280
tgccgtatga agtgaaattt aatcctgtag gcagagaact ctatactcat cccccagaac   2340
acggagtaga gcaagcgtgc caagtctacg cacatgatgc acagaacaga ggagcttatg   2400
tcgagatgca cctcccgggc tcagaagtgg acagcagttt ggtttccttg agcggctccg   2460
gaggatccag ttcagtcacc gtgacacctc ctgatgggac tagcgccctg gtggaatgcg   2520
```

```
agtgtggcgg cacaaagatc tccgagacca tcaacaagac aaaacagttc agccagtgca    2580
caaagaagga gcagtgcaga gcatatcggc tgcagaacga taagtgggtg tataattctg    2640
acaaactgcc caaagcagcg ggagccacct aaaaggaaa actgcatgtc ccattcttgc     2700
tggcagacgg caaatgcacc gtgcctctag caccagaacc tatgataacc ttcggtttca    2760
gatcagtgtc actgaaactg caccctaaga atcccacata tctaatcacc cgccaacttg    2820
ctgatgagcc tcactacacg cacgagctca tatctgaacc agctgttagg aattttaccg    2880
tcaccgaaaa agggtgggag tttgtatggg gaaaccaccc gccgaaaagg tttttgggcac   2940 aggaaacagc acccggaaat ccacatgggc taccgcacga ggtgataact cattattacc    3000
acagataccc tatgtccacc atcctgggtt tgtcaatttg tgccgccatt gcaaccgttt    3060
ccgttgcagc gtctacctgg ctgttttgca gatcaagagt tgcgtgccta actccttacc    3120
ggctaacacc taacgctagg ataccatttt gtctggctgt gctttgctgc gcccgcactg    3180
cccgggccga gaccacctgg gagtccttgg atcacctatg gaacaataac caacagatgt    3240
tctggattca attgctgatc cctctggccg ccttgatcgt agtgactcgc ctgctcaggt    3300
gcgtgtgctg tgtcgtgcct ttttagtca tggccggcgc cgcaggcgcc ggcgcctacg     3360
agcacgcgac cacgatgccg agccaagcgg gaatctcgta taacactata gtcaacagag    3420
caggctacgc accactccct atcagcataa caccaacaaa gatcaagctg atacctacag    3480
tgaacttgga gtacgtcacc tgccactaca aaacaggaat ggattcacca gccatcaaat    3540
gctgcggatc tcaggaatgc actccaactt acaggcctga tgaacagtgc aaagtcttca    3600
caggggttta cccgttcatg tggggtggtg catattgctt ttgcgacact gagaacaccc    3660
aagtcagcaa ggcctacgta atgaaatctg acgactgcct tgcggatcat gctgaagcat    3720
ataaagcgca cacagcctca gtgcaggcgt tcctcaacat cacagtggga gaacactcta    3780
ttgtgactac cgtgtatgtg aatggagaaa ctcctgtgaa tttcaatggg gtcaaaataa    3840
ctgcaggtcc gctttccaca gcttggacac ccttttgatcg caaaatcgtg cagtatgccg    3900
gggagatcta taattatgat tttcctgagt atggggcagg acaaccagga gcatttggag    3960
atatacaatc cagaacagtc tcaagctctg atctgtatgc caataccaac ctagtgctgc    4020
agagacccaa agcaggagcg atccacgtgc catacactca ggcaccttcg ggttttgagc    4080
aatgcaagaa agataaagct ccatcattga aatttaccgc cccttttcgga tgcgaaatat    4140 atacaaaccc cattcgcgcc gaaaactgtg ctgtagggtc aattccatta gccttttgaca   4200 ttcccgacgc cttgttcacc agggtgtcag aaacaccgac actttcagcg gccgaatgca    4260
ctcttaacga gtgcgtgtat tcttccgact ttggtgggat cgccacggtc aagtactcgg    4320
ccagcaagtc aggcaagtgc gcagtccatg tgccatcagg gactgctacc ctaaaagaag    4380
cagcagtcga gctaaccgag caagggtcgg cgactatcca tttctcgacc gcaaatatcc    4440
acccggagtt caggctccaa atatgcacat catatgttac gtgcaaaggt gattgtcacc    4500
ccccgaaaga ccatattgtg acacaccctc agtatcacgc ccaaacattt acagccgcgg    4560
tgtcaaaaac cgcgtggacg tggttaacat ccctgctggg aggatcagcc gtaattatta    4620
taattggctt ggtgctggct actattgtgg ccatgtacgt gctgaccaac cagaaacata    4680
attaaggatc tagatctgct gtgccttcta gttgccagcc atctgttgtt tgcccctccc    4740
ccgtgccttc cttgaccctg gaaggtgcca ctcccactgt cctttcctaa taaaatgagg    4800
aaattgcatc gcattgtctg agtaggtgtc attctattct ggggggtggg gtggggcagg    4860
acagcaaggg ggaggattgg gaagacaata gcaggcatgc tggggatgcg gtgggctcta    4920
```

```
tgggtaccca ggtgctgaag aattgacccg gttcctcctg ggccagaaag aagcaggcac    4980 atcccttct  ctgtgacaca ccctgtccac gcccctggtt cttagttcca gccccactca    5040
taggacactc atagctcagg agggctccgc cttcaatccc accgctaaa  gtacttggag    5100 cggtctctcc ctccctcatc agcccaccaa accaaaccta gcctcaaga  gtgggaagaa    5160 attaaagcaa gataggctat taagtgcaga gggagagaaa atgcctccaa catgtgagga    5220
agtaatgaga gaaatcatag aattttaagg ccatgattta aggccatcat ggcctaagct    5280
tgaaaggaga taggatcaaa gcttggcgta atcatggtca tagctgtttc ctgtgtgaaa    5340
ttgttatccg ctcacaattc cacacaacat acgagccgga agcataaagt gtaaagcctg    5400
gggtgcctaa tgagtgagct aactcacatt aattgcgttg cgctcactgc ccgctttcca    5460
gtcgggaaac ctgtcgtgcc agctgcatta atgaatcggc caacgcgcgg ggagaggcgg    5520
tttgcgtatt gggcgctctt ccgcttcctc gctcactgac tcgctgcgct cggtcgttcg    5580
gctgcggcga gcggtatcag ctcactcaaa ggcggtaata cggttatcca cagaatcagg    5640
ggataacgca ggaaagaaca tgtgagcaaa aggccagcaa aaggccagga accgtaaaaa    5700
ggccgcgttg ctggcgtttt tccataggct ccgcccccct gacgagcatc acaaaaatcg    5760
acgctcaagt cagaggtggc gaaacccgac aggactataa agataccagg cgtttccccc    5820
tggaagctcc ctcgtgcgct ctcctgttcc gaccctgccg cttaccggat acctgtccgc    5880
cttctcccct tcgggaagcg tggcgctttc tcatagctca cgctgtaggt atctcagttc    5940
ggtgtaggtc gttcgctcca agctgggctg tgtgcacgaa ccccccgttc agcccgaccg    6000
ctgcgcctta tccggtaact atcgtcttga gtccaacccg gtaagacacg acttatcgcc    6060
actggcagca gccactggta acaggattag cagagcgagg tatgtaggcg gtgctacaga    6120
gttcttgaag tggtggccta actacggcta cactagaaga acagtatttg gtatctgcgc    6180
tctgctgaag ccagttacct tcggaaaaag agttggtagc tcttgatccg gcaaacaaac    6240
caccgctggt agcggtggtt tttttgtttg caagcagcag attacgcgca gaaaaaaagg    6300
atctcaagaa gatcctttga tcttttctac ggggtctgac gctcagtgga acgaaaactc    6360
acgttaaggg attttggtca tgagattatc aaaaaggatc ttcacctaga tccttttaaa    6420
ttaaaaatga agttttaaat caatctaaag tatatatgag taaacttggt ctgacagtta    6480
ccaatgctta atcagtgagg cacctatctc agcgatctgt ctatttcgtt catccatagt    6540
tgcctgactc cccgtcgtgt agataactac gatacgggag ggcttaccat ctggccccag    6600
tgctgcaatg ataccgcgag aaccacgctc accggctcca gatttatcag caataaacca    6660
gccagccgga agggccgagc gcagaagtgg tcctgcaact ttatccgcct ccatccagtc    6720
tattaattgt tgccgggaag ctagagtaag tagttcgcca gttaatagtt tgcgcaacgt    6780
tgttgccatt gctacaggca tcgtggtgtc acgctcgtcg tttggtatgg cttcattcag    6840
ctccggttcc caacgatcaa ggcgagttac atgatccccc atgttgtgca aaaaagcggt    6900
tagctccttc ggtcctccga tcgttgtcag aagtaagttg gccgcagtgt tatcactcat    6960
ggttatggca gcactgcata attctcttac tgtcatgcca tccgtaagat gcttttctgt    7020
gactggtgag tactcaacca agtcattctg agaatagtgt atgcggcgac cgagttgctc    7080
ttgcccggcg tcaatacggg ataataccgc gccacatagc agaactttaa aagtgctcat    7140
cattggaaaa cgttcttcgg ggcgaaaact ctcaaggatc ttaccgctgt tgagatccag    7200
ttcgatgtaa cccactcgtg cacccaactg atcttcagca tcttttactt tcaccagcgt    7260
```

```
ttctgggtga gcaaaaacag gaaggcaaaa tgccgcaaaa agggaataa gggcgacacg    7320 gaaatgttga atactcatac tcttcctttt tcaatattat tgaagcattt atcagggtta    7380
ttgtctcatg agcggataca tatttgaatg tatttagaaa aataaacaaa tagggggttcc   7440 gcgcacattt ccccgaaaag tgccacctga cgtctaagaa accattatta tcatgacatt    7500
aacctataaa aataggcgta tcacgaggcc ctttcgggtc gcgcgtttcg tgatgacgg     7560 tgaaaacctc tgacacatgc agctcccgtt gacggtcaca gcttgtctgt aagcggatgc    7620
cgggagcaga caagcccgtc agggcgcgtc agcgggtgtt ggcgggtgtc ggggctggct    7680
taactatgcg gcatcagagc agattgtact gagagtgcac cataaaattg taaacgttaa    7740
tattttgtta aaattcgcgt taaattttg ttaaatcagc tcatttttta accaataggc     7800
cgaaatcggc aaaatccctt ataaatcaaa agaatagccc gagatagggt tgagtgttgt    7860
tccagtttgg aacaagagtc cactattaaa gaacgtggac tccaacgtca aagggcgaaa    7920
aaccgtctat cagggcgatg gcccactacg tgaaccatca cccaaatcaa gttttttggg    7980
gtcgaggtgc cgtaaagcac taaatcggaa ccctaaaggg agcccccgat ttagagcttg    8040
acggggaaag ccggcgaacg tggcgagaaa ggaagggaag aaagcgaaag gagcgggcgc    8100
tagggcgctg gcaagtgtag cggtcacgct gcgcgtaacc accacacccg ccgcgcttaa    8160
tgcgccgcta cagggcgcgt actatggttg ctttgacgta tgcggtgtga ataccgcac    8220 agatgcgtaa ggagaaaata ccgcatcagg cgccattcgc cattcaggct gcgcaactgt    8280
tgggaagggc gatcggtgcg ggcctcttcg ctattacgcc agctggcgaa aggggatgt    8340 gctgcaaggc gattaagttg ggtaacgcca gggttttccc agtcacgacg ttgtaaaacg    8400
acggccagtg aattccatgg tctcaacttt c                                  8431

<210> SEQ ID NO 27
<211> LENGTH: 3813
<212> TYPE: DNA
<213> ORGANISM: Artificial Sequence
<220> FEATURE:
<223> OTHER INFORMATION: Synthetic polynucleotide

<400> SEQUENCE: 27
atggagttca tcccgacgca aactttctat aacagaaggt accaaccccg accctgggcc     60
ccacgcccta caattcaagt aattagacct agaccacgtc cacagaggca ggctgggcaa    120
ctcgcccagc tgatctccgc agtcaacaaa ttgaccatgc gcgcggtacc tcaacagaag    180
cctcgcagaa atcggaaaaa caagaagcaa aggcagaaga agcaggcgcc gcaaaacgac    240
ccaaagcaaa agaagcaacc accacaaaag aagccggctc aaaagaagaa gaaaccaggc    300
cgtagggaga gaatgtgcat gaaaattgaa aatgattgca tcttcgaagt caagcatgaa    360
ggcaaagtga tgggctacgc atgcctggtg ggggataaag taatgaaacc agcacatgtg    420
aagggaacta tcgacaatgc cgatctggct aaactggcct ttaagcggtc gtctaaatac    480
gatcttgaat gtgcacagat accggtgcac atgaagtctg atgcctcgaa gtttacccac    540
gagaaacccg aggggtacta taactggcat cacggagcag tgcagtattc aggaggccgg    600
ttcactatcc cgacgggtgc aggcaagccg ggagacagcg gcagaccgat cttcgacaac    660
aaaggacggg tggtggccat cgtcctagga ggggccaacg aaggtgcccg cacggccctc    720
tccgtggtga cgtggaacaa agacatcgtc acaaaaatta cccctgaggg agccgaagag    780
tggagcctcg ccctcccggt cttgtgcctg ttggcaaaca ctacattccc ctgctctcag    840
ccgcctttgc acccctgctg ctacgaaaag gaaccggaaa gcaccttgcg catgcttgag    900
```

```
gacaacgtga tgagacccgg atactaccag ctactaaaag catcgctgac ttgctctccc    960
caccgccaaa gacgcagtac taaggacaat tttaatgtct ataaagccac aagaccatat   1020
ctagctcatt gtcctgactg cggagaaggg cattcgtgcc acagccctat cgcattggag   1080
cgcatcagaa atgaagcaac ggacggaacg ctgaaaatcc aggtctcttt gcagatcggg   1140
ataaagacag atgacagcca cgattggacc aagctgcgct atatggatag ccatacgcca   1200
gcggacgcgg agcgagccgg attgcttgta aggacttcag caccgtgcac gatcaccggg   1260
accatgggac actttattct cgcccgatgc ccgaaggag agacgctgac agtgggattt    1320
acggacagca gaaagatcag ccacacatgc acacacccgt tccatcatga accacctgtg   1380
ataggtaggg agaggttcca ctctcgacca caacatggta aagagttacc ttgcagcacg   1440
tacgtgcaga gcaccgctgc cactgctgag gagatagagg tgcatatgcc cccagatact   1500
cctgaccgca cgctgatgac gcagcagtct ggcaacgtga agatcacagt taatgggcag   1560
acggtgcggt acaagtgcaa ctgcggtggc tccggaggac taaactggta ccgcatgagc   1620
cccagcaacc agacggacaa gctggccgcc ttcgaggat ccaacgaggg actgacaacc    1680
acagacaaag tgatcaataa ctgcaaaatt gatcagtgcc atgctgcagt cactaatcac   1740
aagaattggc aatacaactc ccctttagtc ccgcgcaacg ctgaactcgg ggaccgtaaa   1800
ggaaagatcc acatcccatt cccattggca aacgtgactt gcagagtgcc aaaagcaaga   1860
aaccctacag taacttacgg aaaaaaccaa gtcaccatgc tgctgtatcc tgaccatccg   1920
acactcttgt cttaccgtaa catgggacag gaaccaaatt accacgagga gtgggtgaca   1980
cacaagaagg aggttacctt gaccgtgcct actgagggtc tggaggtcac ttggggcaac   2040
aacgaaccat acaagtactg gccgcagatg tctacgaacg gtactgctca tggtcaccca   2100
catgagataa tcttgtacta ttatgagctg taccccacta tgactgtagt cattgtgtcg   2160
gtggcctcgt tcgtgcttct gtcgatggtg ggcacagcag tgggaatgtg tgtgtgcgca   2220
cggcgcagat gcattacacc atatgaatta acaccaggag ccactgttcc cttcctgctc   2280
agcctgctat gctgcgtcag aacgaccaag gcggccacat attacgaggc tgcggcatat   2340
ctatggaacg aacagcagcc cctgttctgg ttgcaggctc ttatcccgct ggccgccttg   2400
atcgtcctgt gcaactgtct gaaactcttg ccatgctgct gtaagaccct ggcttttta    2460
gccgtaatga gcatcggtgc ccacactgtg agcgcgtacg aacacgtaac agtgatcccg   2520
aacacggtgg gagtaccgta taagactctt gtcaacagac cgggttacag ccccatggtg   2580
ttggagatgg agctacaatc agtcaccttg gaaccaacac tgtcacttga ctacatcacg   2640
tgcgagtaca aaactgtcat cccctccccg tacgtgaagt gctgtggtac agcagagtgc   2700
aaggacaaga gcctaccaga ctacagctgc aaggtcttta ctggagtcta cccatttatg   2760
tggggcggcg cctactgctt ttgcgacgcc gaaaatacgc aattgagcga ggcacatgta   2820
gagaaatctg atcttgcaa aacagagttt gcatcggcct acagagccca caccgcatcg   2880
gcgtcggcga agctccgcgt cctttaccaa ggaaacaaca ttaccgtagc tgcctacgct   2940
aacggtgacc atgccgtcac agtaaaggac gccaagtttg tcgtgggccc aatgtcctcc   3000
gcctggacac cttttgacaa caaatcgtg gtgtacaaag cgacgtcta caacatggac    3060
tacccacctt ttggcgcagg aagaccagga caatttggtg acattcaaag tcgtacaccg   3120
gaaagtaaag acgtttatgc caacactcag ttggtactac agaggccagc agcaggcacg   3180
gtacatgtac catactctca ggcaccatct ggcttcaagt attggctgaa ggaacgagga   3240
```

| | |
|---|---:|
| gcatcgctac agcacacggc accgttcggt tgccagattg cgacaaaccc ggtaagagct | 3300 |
| gtaaattgcg ctgtggggaa cataccaatt tccatcgaca taccggatgc ggcctttact | 3360 |
| agggttgtcg atgcaccctc tgtaacggac atgtcatgcg aagtaccagc ctgcactcac | 3420 |
| tcctccgact ttgggggcgt cgccatcatc aaatacacag ctagcaagaa aggtaaatgt | 3480 |
| gcagtacatt cgatgaccaa cgccgttacc attcgagaag ccgacgtaga agtagagggg | 3540 |
| aactcccagc tgcaaatatc cttctcaaca gccctggcaa cgccgagtt tcgcgtgcaa | 3600 |
| gtgtgctcca cacaagtaca ctgcgcagcc gcatgccacc ctccaaagga ccacatagtc | 3660 |
| aattacccag catcacacac cacccttggg gtccaggata tatccacaac ggcaatgtct | 3720 |
| tgggtgcaga agattacggg aggagtagga ttaattgttg ctgttgctgc cttaatttta | 3780 |
| attgtggtgc tatgcgtgtc gtttagcagg cac | 3813 |

<210> SEQ ID NO 28
<211> LENGTH: 3837
<212> TYPE: DNA
<213> ORGANISM: Artificial Sequence
<220> FEATURE:
<223> OTHER INFORMATION: Synthetic polynucleotide

<400> SEQUENCE: 28

| | |
|---|---:|
| atgttcccgt tccagccaat gtatccgatg cagccaatgc cctatcgcaa cccgttcgcg | 60 |
| gccccgcgca ggccctggtt ccccagaacc gacccttttc tggcgatgca ggtgcaggaa | 120 |
| ttaacccgct cgatggctaa cctgacgttc aagcaacgcc gggacgcgcc acctgagggg | 180 |
| ccatccgcta ataaaccgaa gaaggaggcc tcgcaaaaac agaaagggg aggccaaggg | 240 |
| aagaagaaga gaaccaagg gaagaagaag gctaagacag gccgcctaa tccgaaggca | 300 |
| cagaatggaa acaagaagaa gaccaacaag aaaccaggca agagacagcg catggtcatg | 360 |
| aaattggaat ctgacaagac gttcccaatc atgttggaag ggaagataaa cggctacgct | 420 |
| tgtgtggtcg gagggaagtt attcaggccg atgcatgtgg aaggcaagat cgacaacgac | 480 |
| gttctggccg cgcttaagac gaagaaagca tccaaatacg atcttgagta tgcagatgtg | 540 |
| ccacagaaca tgcgggccga tacattcaaa tacacccatg agaaaccca aggctattac | 600 |
| agctggcatc atggagcagt ccaatatgaa atgggcgtt tcacggtgcc gaaaggagtt | 660 |
| ggggccaagg gagacagcgg acgacccatt ctggataacc agggacgggt ggtcgctatt | 720 |
| gtgctgggag gtgtgaatga aggatctagg acagcccttt cagtcgtcat gtggaacgag | 780 |
| aagggagtta ccgtgaagta tactccagag aactgcgagc aatggtcact agtgaccacc | 840 |
| atgtgtctgc tcgccaatgt gacgttccca tgtgctcaac caccaattg ctacgacaga | 900 |
| aaaccagcag agactttggc catgctcagc gttaacgttg acaacccggg ctacgatgag | 960 |
| ctgctggaag cagctgttaa gtgccccgga aggaaaagga gatccaccga ggagctgttt | 1020 |
| aatgagtata gctaacgcg cccttacatg gccagatgca tcagatgtgc agttgggagc | 1080 |
| tgccatagtc caatagcaat cgaggcagta aagagcgacg ggcacgacgg ttatgttaga | 1140 |
| cttcagactt cctcgcagta tggcctggat tcctccggca acttaaaggg caggaccatg | 1200 |
| cggtatgaca tgcacgggac cattaaagag ataccactac atcaagtgtc actctataca | 1260 |
| tctcgcccgt gtcacattgt ggatgggcac ggttatttcc tgcttgccag gtgcccggca | 1320 |
| ggggactcca tcaccatgga atttaagaaa gattccgtca gacactcctg ctcggtgccg | 1380 |
| tatgaagtga aatttaatcc tgtaggcaga gaactctata ctcatccccc agaacacgga | 1440 |
| gtagagcaag cgtgccaagt ctacgcacat gatgcacaga acagaggagc ttatgtcgag | 1500 |

```
atgcacctcc cgggctcaga agtggacagc agtttggttt ccttgagcgg cagttccgga   1560
ggactaaact ggtaccgcat gagccccagc aaccagacgg acaagctggc cgccttcgga   1620
ggatcctcag tcaccgtgac acctcctgat gggactagcg ccctggtgga atgcgagtgt   1680
ggcggcacaa agatctccga gaccatcaac aagacaaaac agttcagcca gtgcacaaag   1740
aaggagcagt gcagagcata tcggctgcag aacgataagt gggtgtataa ttctgacaaa   1800
ctgcccaaag cagcgggagc caccttaaaa ggaaaactgc atgtcccatt cttgctggca   1860
gacggcaaat gcaccgtgcc tctagcacca gaacctatga taaccttcgg tttcagatca   1920
gtgtcactga aactgcaccc taagaatccc acatatctaa tcacccgcca acttgctgat   1980
gagcctcact acacgcacga gctcatatct gaaccagctg ttaggaattt taccgtcacc   2040
gaaaaagggt gggagtttgt atggggaaac caccccgccga aaaggttttg ggcacaggaa   2100
acagcacccg aaatccaca tgggctaccg cacgaggtga taactcatta ttaccacaga   2160
taccctatgt ccaccatcct gggtttgtca atttgtgccg ccattgcaac cgtttccgtt   2220
gcagcgtcta cctggctgtt ttgcagatca agagttgcgt gcctaactcc ttaccggcta   2280
acacctaacg ctaggatacc attttgtctg gctgtgcttt gctgcgcccg cactgcccgg   2340
gccgagacca cctgggagtc cttggatcac ctatggaaca ataaccaaca gatgttctgg   2400
attcaattgc tgatccctct ggccgccttg atcgtagtga ctcgcctgct caggtgcgtg   2460
tgctgtgtcg tgccttttttt agtcatggcc ggcgccgcag gcgccggcgc ctacgagcac   2520
gcgaccacga tgccgagcca agcgggaatc tcgtataaca ctatagtcaa cagagcaggc   2580
tacgcaccac tccctatcag cataacacca acaaagatca agctgatacc tacagtgaac   2640
ttggagtacg tcacctgcca ctacaaaaca ggaatggatt caccagccat caaatgctgc   2700
ggatctcagg aatgcactcc aacttacagg cctgatgaac agtgcaaagt cttcacaggg   2760
gtttacccgt tcatgtgggg tggtgcatat tgcttttgcg cactgagaa cacccaagtc   2820 agcaaggcct acgtaatgaa atctgacgac tgccttgcgg atcatgctga agcatataaa   2880
gcgcacacag cctcagtgca ggcgttcctc aacatcacag tgggagaaca ctctattgtg   2940
actaccgtgt atgtgaatgg agaaactcct gtgaatttca atggggtcaa ataactgca   3000 ggtccgcttt ccacagcttg acaccctttg atcgcaaaa tcgtgcagta tgccggggag   3060
atctataatt atgattttcc tgagtatggg gcaggacaac caggagcatt ggagatata   3120 caatccagaa cagtctcaag ctctgatctg tatgccaata ccaacctagt gctgcagaga   3180
cccaaagcag gagcgatcca cgtgccatac actcaggcac cttcgggttt tgagcaatgg   3240
aagaaagata agctccatc attgaaattt accgcccctt tcggatgcga aatatataca   3300
aaccccattc gcgccgaaaa ctgtgctgta gggtcaattc cattagcctt tgacattccc   3360
gacgccttgt tcaccagggt gtcagaaaca ccgacactt cagcggccga atgcactctt   3420
aacgagtgcg tgtattcttc cgactttggt gggatcgcca cggtcaagta ctcggccagc   3480
aagtcaggca agtgcgcagt ccatgtgcca tcagggactg ctaccctaaa agaagcagca   3540
gtcgagctaa ccgagcaagg gtcggcgact atccatttct cgaccgcaaa tatccacccg   3600
gagttcaggc tccaaatatg cacatcatat gttacgtgca aggtgattg tcacccccg   3660 aaagaccata ttgtgacaca ccctcagtat cacgcccaaa catttacagc cgcggtgtca   3720
aaaaccgcgt ggacgtggtt aacatccctg ctgggaggat cagccgtaat tattataatt   3780
ggcttggtgc tggctactat tgtggccatg tacgtgctga ccaaccagaa acataat     3837
```

<210> SEQ ID NO 29
<211> LENGTH: 3798
<212> TYPE: DNA
<213> ORGANISM: Artificial Sequence
<220> FEATURE:
<223> OTHER INFORMATION: Synthetic polynucleotide

<400> SEQUENCE: 29

| | | | | | |
|---|---|---|---|---|---|
| atggagttca | tcccgacgca | aactttctat | aacagaaggt | accaaccccg | accctgggcc | 60 |
| ccacgcccta | caattcaagt | aattagacct | agaccacgtc | cacagaggca | ggctgggcaa | 120 |
| ctcgcccagc | tgatctccgc | agtcaacaaa | ttgaccatgc | gcgcggtacc | tcaacagaag | 180 |
| cctcgcagaa | atcggaaaaa | caagaagcaa | aggcagaaga | agcaggcgcc | gcaaaacgac | 240 |
| ccaaagcaaa | agaagcaacc | accacaaaag | aagccggctc | aaaagaagaa | gaaaccaggc | 300 |
| cgtagggaga | gaatgtgcat | gaaaattgaa | aatgattgca | tcttcgaagt | caagcatgaa | 360 |
| ggcaaagtga | tgggctacgc | atgcctggtg | ggggataaag | taatgaaacc | agcacatgtg | 420 |
| aagggaacta | tcgacaatgc | cgatctggct | aaactggcct | ttaagcggtc | gtctaaatac | 480 |
| gatcttgaat | gtgcacagat | accggtgcac | atgaagtctg | atgcctcgaa | gtttacccac | 540 |
| gagaaacccg | aggggtacta | taactggcat | cacgagcag | tgcagtattc | aggaggccgg | 600 |
| ttcactatcc | cgacgggtgc | aggcaagccg | ggagacagcg | gcagaccgat | cttcgacaac | 660 |
| aaaggacggg | tggtggccat | cgtcctagga | ggggccaacg | aaggtgcccg | cacggccctc | 720 |
| tccgtggtga | cgtggaacaa | agacatcgtc | acaaaaatta | cccctgaggg | agccgaagag | 780 |
| tggagcctcg | ccctcccggt | cttgtgcctg | ttggcaaaca | ctacattccc | ctgctctcag | 840 |
| ccgccttgca | caccctgctg | ctacgaaaag | gaaccggaaa | gcaccttgcg | catgcttgag | 900 |
| gacaacgtga | tgagacccgg | atactaccag | ctactaaaag | catcgctgac | ttgctctccc | 960 |
| caccgccaaa | gacgcagtac | taaggacaat | tttaatgtct | ataaagccac | aagaccatat | 1020 |
| ctagctcatt | gtcctgactg | cggagaaggg | cattcgtgcc | acagccctat | cgcattggag | 1080 |
| cgcatcagaa | atgaagcaac | ggacggaacg | ctgaaaatcc | aggtctcttt | gcagatcggg | 1140 |
| ataaagacag | atgacagcca | cgattggacc | aagctgcgct | atatggatag | ccatacgcca | 1200 |
| gcggacgcgg | agcgagccgg | attgcttgta | aggacttcag | caccgtgcac | gatcaccggg | 1260 |
| accatgggac | actttattct | cgcccgatgc | ccgaaggag | agacgctgac | agtgggattt | 1320 |
| acggacagca | gaaagatcag | ccacacatgc | acacacccgt | tccatcatga | accacctgtg | 1380 |
| ataggtaggg | agaggttcca | ctctcgacca | caacatggta | agagttacc | ttgcagcacg | 1440 |
| tacgtgcaga | gcaccgctgc | cactgctgag | gagatagagg | tgcatatgcc | cccagatact | 1500 |
| cctgaccgca | cgctgatgac | gcagcagtct | ggcaacgtga | agatcacagt | taatgggcag | 1560 |
| acggtgcggt | acaagtgcaa | ctgcggtggc | tccggaggcg | gcgccatcag | cctgcacccc | 1620 |
| aaggccaaga | tcgaggaatc | tggatccaac | gagggactga | caaccacaga | caaagtgatc | 1680 |
| aataactgca | aaattgatca | gtgccatgct | gcagtcacta | atcacaagaa | ttggcaatac | 1740 |
| aactccccctt | tagtcccgcg | caacgctgaa | ctcgggacc | gtaaaggaaa | gatccacatc | 1800 |
| ccattcccat | tggcaaacgt | gacttgcaga | gtgccaaaag | caagaaaccc | tacagtaact | 1860 |
| tacggaaaaa | accaagtcac | catgctgctg | tatcctgacc | atccgacact | cttgtcttac | 1920 |
| cgtaacatgg | acaggaacc | aaattaccac | gaggagtggg | tgacacacaa | gaaggaggtt | 1980 |
| accttgaccg | tgcctactga | gggtctggag | gtcacttggg | gcaacaacga | accatacaag | 2040 |
| tactggccgc | agatgtctac | gaacggtact | gctcatggtc | acccacatga | gataatcttg | 2100 |

```
tactattatg agctgtaccc cactatgact gtagtcattg tgtcggtggc ctcgttcgtg      2160
cttctgtcga tggtgggcac agcagtggga atgtgtgtgt gcgcacggcg cagatgcatt      2220
acaccatatg aattaacacc aggagccact gttcccttcc tgctcagcct gctatgctgc      2280
gtcagaacga ccaaggcggc cacatattac gaggctgcgg catatctatg aacgaacag       2340 cagcccctgt tctggttgca ggctcttatc ccgctggccg ccttgatcgt cctgtgcaac      2400
tgtctgaaac tcttgccatg ctgctgtaag accctggctt ttttagccgt aatgagcatc      2460
ggtgcccaca ctgtgagcgc gtacgaacac gtaacagtga tcccgaacac ggtgggagta      2520
ccgtataaga ctcttgtcaa cagaccgggt tacagcccca tggtgttgga gatggagcta      2580
caatcagtca ccttggaacc aacactgtca cttgactaca tcacgtgcga gtacaaaact      2640
gtcatcccct ccccgtacgt gaagtgctgt ggtacagcag agtgcaagga caagagccta      2700
ccagactaca gctgcaaggt ctttactgga gtctacccat ttatgtgggg cggcgcctac      2760
tgcttttgcg acgccgaaaa tacgcaattg agcgaggcac atgtagagaa atctgaatct      2820
tgcaaaacag agtttgcatc ggcctacaga gcccacaccg catcggcgtc ggcgaagctc      2880
cgcgtccttt accaaggaaa caacattacc gtagctgcct acgctaacgg tgaccatgcc      2940
gtcacagtaa aggacgccaa gtttgtcgtg ggcccaatgt cctccgcctg acacctttt       3000 gacaacaaaa tcgtggtgta caaaggcgac gtctacaaca tggactaccc acctttggc      3060 gcaggaagac caggacaatt tggtgacatt caaagtcgta caccggaaag taaagacgtt      3120
tatgccaaca ctcagttggt actacagagg ccagcagcag gcacggtaca tgtaccatac      3180
tctcaggcac catctggctt caagtattgg ctgaaggaac gaggagcatc gctacagcac      3240
acggcaccgt tcggttgcca gattgcgaca aacccggtaa gagctgtaaa ttgcgctgtg      3300
gggaacatac caatttccat cgacataccg gatgcggcct tactagggt tgtcgatgca       3360 ccctctgtaa cggacatgtc atgcgaagta ccagcctgca ctcactcctc cgactttggg      3420
ggcgtcgcca tcatcaaata cacagctagc aagaaaggta atgtgcagt acattcgatg       3480 accaacgccg ttaccattcg agaagccgac gtagaagtag aggggaactc ccagctgcaa      3540
atatccttct caacagccct ggcaagcgcc gagtttcgcg tgcaagtgtg ctccacacaa      3600
gtacactgcg cagccgcatg ccaccctcca aaggaccaca tagtcaatta cccagcatca      3660
cacaccaccc ttggggtcca ggatatatcc acaacgcaa tgtcttgggt gcagaagatt       3720
acgggaggag taggattaat tgttgctgtt gctgccttaa ttttaattgt ggtgctatgc      3780
gtgtcgttta gcaggcac                                                    3798
```

<210> SEQ ID NO 30
<211> LENGTH: 3822
<212> TYPE: DNA
<213> ORGANISM: Artificial Sequence
<220> FEATURE:
<223> OTHER INFORMATION: Synthetic polynucleotide

<400> SEQUENCE: 30

```
atgttcccgt tccagccaat gtatccgatg cagccaatgc cctatcgcaa cccgttcgcg        60
gccccgcgca ggccctggtt ccccagaacc gaccctttc tggcgatgca ggtgcaggaa        120
ttaacccgct cgatggctaa cctgacgttc aagcaacgcc gggacgcgcc acctgagggg       180
ccatccgcta ataaaccgaa gaaggaggcc tcgcaaaaac agaaaggggg aggccaaggg       240
aagaagaaga agaaccaagg gaagaagaag gctaagacag ggccgcctaa tccgaaggca       300
```

```
cagaatggaa acaagaagaa gaccaacaag aaaccaggca agagacagcg catggtcatg      360
aaattggaat ctgacaagac gttcccaatc atgttggaag ggaagataaa cggctacgct      420
tgtgtggtcg gagggaagtt attcaggccg atgcatgtgg aaggcaagat cgacaacgac      480
gttctggccg cgcttaagac gaagaaagca tccaaatacg atcttgagta tgcagatgtg      540
ccacagaaca tgcgggccga tacattcaaa tacacccatg agaaacccca aggctattac      600
agctggcatc atggagcagt ccaatatgaa aatgggcgtt tcacggtgcc gaaaggagtt      660
ggggccaagg gagacagcgg acgacccatt ctggataacc agggacgggt ggtcgctatt      720
gtgctgggag gtgtgaatga aggatctagg acagccettt cagtcgtcat gtggaacgag      780
aagggagtta ccgtgaagta tactccagag aactgcgagc aatggtcact agtgaccacc      840
atgtgtctgc tcgccaatgt gacgttccca tgtgctcaac caccaatttg ctacgacaga      900
aaaccagcag agactttggc catgctcagc gttaacgttg acaacccggg ctacgatgag      960
ctgctggaag cagctgttaa gtgccccgga aggaaaagga gatccaccga ggagctgttt     1020
aatgagtata agctaacgcg cccttacatg gccagatgca tcagatgtgc agttgggagc     1080
tgccatagtc caatagcaat cgaggcagta aagagcgacg gcacgacgg ttatgttaga      1140 cttcagactt cctcgcagta tggcctggat tcctccggca acttaaaggg caggaccatg     1200
cggtatgaca tgcacgggac cattaaagag ataccactac atcaagtgtc actctataca     1260
tctcgcccgt gtcacattgt ggatgggcac ggttatttcc tgcttgccag gtgcccggca     1320
ggggactcca tcaccatgga atttaagaaa gattccgtca gacactcctg ctcggtgccg     1380
tatgaagtga aatttaatcc tgtaggcaga gaactctata ctcatccccc agaacacgga     1440
gtagagcaag cgtgccaagt ctacgcacat gatgcacaga acagaggagc ttatgtcgag     1500
atgcacctcc cgggctcaga agtggacagc agtttggttt ccttgagcgg cagttccgga     1560
ggcggcgcca tcagcctgca ccccaaggcc aagatcgagg aatctggatc ctcagtcacc     1620
gtgacacctc ctgatgggac tagcgccctg gtggaatgcg agtgtggcgg cacaaagatc     1680
tccgagacca tcaacaagac aaaacagttc agccagtgca aagaagga gcagtgcaga       1740 gcatatcggc tgcagaacga taagtgggtg tataattctg acaaactgcc caaagcagcg     1800
ggagccacct aaaaggaaa actgcatgtc ccattcttgc tggcagacgg caaatgcacc      1860
gtgcctctag caccagaacc tatgataacc ttcggttca gatcagtgtc actgaaactg      1920 cacccctaaga atcccacata tctaatcacc cgccaacttg ctgatgagcc tcactacacg     1980
cacgagctca tatctgaacc agctgttagg aattttaccg tcaccgaaaa agggtgggag     2040
tttgtatggg gaaaccaccc gccgaaaagg ttttgggcac aggaaacagc acccggaaat     2100
ccacatgggc taccgcacga ggtgataact cattattacc acagataccc tatgtccacc     2160
atcctgggtt tgtcaatttg tgccgccatt gcaaccgttt ccgttgcagc gtctacctgg     2220
ctgttttgca gatcaagagt tgcgtgccta actccttacc ggctaacacc taacgctagg     2280
ataccatttt gtctggctgt gctttgctgc gcccgcactg cccgggccga gaccacctgg     2340
gagtccttgg atcacctatg gaacaataac caacagatgt tctggattca attgctgatc     2400
cctctggccg ccttgatcgt agtgactcgc tgctcaggt gcgtgtgctg tgtcgtgcct      2460
tttttagtca tggccggcgc cgcaggcgcc ggcgcctacg agcacgcgac cacgatgccg     2520
agccaagcgg gaatctcgta taacactata gtcaacagag caggctacgc accactccct     2580
atcagcataa caccaacaaa gatcaagctg ataccctacag tgaacttgga gtacgtcacc      2640
tgccactaca aaacaggaat ggattcacca gccatcaaat gctgcggatc tcaggaatgc     2700
```

```
actccaactt acaggcctga tgaacagtgc aaagtcttca cagggggttta cccgttcatg    2760 tggggtggtg catattgctt ttgcgacact gagaacaccc aagtcagcaa ggcctacgta    2820
atgaaatctg acgactgcct tgcggatcat gctgaagcat ataaagcgca cacagcctca    2880
gtgcaggcgt tcctcaacat cacagtggga gaacactcta ttgtgactac cgtgtatgtg    2940
aatggagaaa ctcctgtgaa tttcaatggg gtcaaaataa ctgcaggtcc gctttccaca    3000
gcttggacac cctttgatcg caaaatcgtg cagtatgccg gggagatcta taattatgat    3060
tttcctgagt atggggcagg acaaccagga gcatttggag atatacaatc agaacagtc    3120 tcaagctctg atctgtatgc caataccaac ctagtgctgc agagacccaa agcaggagcg    3180
atccacgtgc catacactca ggcaccttcg ggttttgagc aatggaagaa agataaagct    3240
ccatcattga aatttaccgc ccctttcgga tgcgaaatat atacaaaccc cattcgcgcc    3300
gaaaactgtg ctgtagggtc aattccatta gcctttgaca ttcccgacgc cttgttcacc    3360
agggtgtcag aaaaccgac actttcagcg gccgaatgca ctcttaacga gtgcgtgtat    3420
tcttccgact ttggtgggat cgccacggtc aagtactcgg ccagcaagtc aggcaagtgc    3480
gcagtccatg tgccatcagg gactgctacc ctaaaagaag cagcagtcga gctaaccgag    3540
caagggtcgg cgactatcca tttctcgacc gcaaatatcc acccggagtt caggctccaa    3600
atatgcacat catatgttac gtgcaaaggt gattgtcacc ccccgaaaga ccatattgtg    3660
acacaccctc agtatcacgc ccaaacattt acagccgcgg tgtcaaaaac cgcgtggacg    3720
tggttaacat ccctgctggg aggatcagcc gtaattatta taattggctt ggtgctggct    3780
actattgtgg ccatgtacgt gctgaccaac cagaaacata at                       3822
```

<210> SEQ ID NO 31
<211> LENGTH: 3792
<212> TYPE: DNA
<213> ORGANISM: Artificial Sequence
<220> FEATURE:
<223> OTHER INFORMATION: Synthetic polynucleotide

<400> SEQUENCE: 31

```
atggagttca tcccgacgca aactttctat aacagaaggt accaaccccg accctgggcc     60
ccacgcccta caattcaagt aattagacct agaccacgtc cacagaggca ggctgggcaa    120
ctcgcccagc tgatctccgc agtcaacaaa ttgaccatgc gcgcggtacc tcaacagaag    180
cctcgcagaa atcggaaaaa caagaagcaa aggcagaaga agcaggcgcc gcaaaacgac    240
ccaaagcaaa agaagcaacc accacaaaag aagccggctc aaaagaagaa gaaaccaggc    300
cgtagggaga gaatgtgcat gaaaattgaa aatgattgca tcttcgaagt caagcatgaa    360
ggcaaagtga tgggctacgc atgcctggtg ggggataaag taatgaaacc agcacatgtg    420
aagggaacta tcgacaatgc cgatctggct aaactggcct ttaagcggtc gtctaaatac    480
gatcttgaat gtgcacagat accggtgcac atgaagtctg atgcctcgaa gtttacccac    540
gagaaacccg agggggtacta taactggcat cacggagcag tgcagtattc aggaggccgg    600
ttcactatcc cgacgggtgc aggcaagccg ggagacagcg gcagaccgat cttcgacaac    660
aaaggacggg tggtggccat cgtcctagga ggggccaacg aaggtgcccg cacggccctc    720
tccgtggtga cgtggaacaa agacatcgtc acaaaaatta cccctgaggg agccgaagag    780
tggagcctcg ccctcccggt cttgtgcctg ttggcaaaca ctacattccc ctgctctcag    840 ccgcccttgca caccctgctg ctacgaaaag gaaccggaaa gcacccttgcg catgcttgag    900
```

```
gacaacgtga tgagacccgg atactaccag ctactaaaag catcgctgac ttgctctccc    960
caccgccaaa gacgcagtac taaggacaat tttaatgtct ataaagccac aagaccatat   1020
ctagctcatt gtcctgactg cggagaaggg cattcgtgcc acagccctat cgcattggag   1080
cgcatcagaa atgaagcaac ggacggaacg ctgaaaatcc aggtctcttt gcagatcggg   1140
ataaagacag atgacagcca cgattggacc aagctgcgct atatggatag ccatacgcca   1200
gcggacgcgg agcgagccgg attgcttgta aggacttcag caccgtgcac gatcaccggg   1260
accatgggac actttattct cgcccgatgc ccgaaaggag agacgctgac agtgggattt   1320
acggacagca gaaagatcag ccacacatgc acacacccgt tccatcatga accacctgtg   1380
ataggtaggg agaggttcca ctctcgacca caacatggta aagagttacc ttgcagcacg   1440
tacgtgcaga gcaccgctgc cactgctgag gagatagagg tgcatatgcc cccagatact   1500
cctgaccgca cgctgatgac gcagcagtct ggcaacgtga agatcacagt taatgggcag   1560
acggtgcggt acaagtgcaa ctgcggtggc tccggaggct gcatcatcag ctacggcgga   1620
gccgactact gcggcggatc caacgaggga ctgacaacca cagacaaagt gatcaataac   1680
tgcaaaattg atcagtgcca tgctgcagtc actaatcaca agaattggca atacaactcc   1740
cctttagtcc cgcgcaacgc tgaactcggg gaccgtaaag gaaagatcca catcccattc   1800
ccattggcaa acgtgacttg cagagtgcca aaagcaagaa accctacagt aacttacgga   1860
aaaaaccaag tcaccatgct gctgtatcct gaccatccga cactcttgtc ttaccgtaac   1920
atgggacagg aaccaaatta ccacgaggag tgggtgacac acaagaagga ggttaccttg   1980
accgtgccta ctgagggtct ggaggtcact tggggcaaca acgaaccata caagtactgg   2040
ccgcagatgt ctacgaacgg tactgctcat ggtcacccac atgagataat cttgtactat   2100
tatgagctgt accccactat gactgtagtc attgtgtcgg tggcctcgtt cgtgcttctg   2160
tcgatggtgg gcacagcagt gggaatgtgt gtgtgcgcac ggcgcagatg cattacacca   2220
tatgaattaa caccaggagc cactgttccc ttcctgctca gcctgctatg ctgcgtcaga   2280
acgaccaagg cggccacata ttacgaggct gcggcatatc tatggaacga acagcagccc   2340
ctgttctggt tgcaggctct tatcccgctg ccgccttga tcgtcctgtg caactgtctg   2400
aaactcttgc catgctgctg taagaccctg gcttttttag ccgtaatgag catcggtgcc   2460
cacactgtga gcgcgtacga acacgtaaca gtgatcccga acacggtggg agtaccgtat   2520
aagactcttg tcaacagacc gggttacagc cccatggtgt tggagatgga gctacaatca   2580
gtcaccttgg aaccaacact gtcacttgac tacatcacgt gcgagtacaa aactgtcatc   2640
ccctccccgt acgtgaagtg ctgtggtaca gcagagtgca aggacaagag cctaccagac   2700
tacagctgca aggtctttac tggagtctac ccatttatgt ggggcggcgc ctactgcttt   2760
tgcgacgccg aaaatacgca attgagcgag gcacatgtag agaaatctga atcttgcaaa   2820
acagagtttg catcggccta cagagcccac accgcatcgg cgtcggcgaa gctccgcgtc   2880
ctttaccaag gaaacaacat taccgtagct gcctacgcta acggtgacca tgccgtcaca   2940
gtaaaggacg ccaagtttgt cgtgggccca atgtcctccg cctggacacc ttttgacaac   3000
aaaatcgtgg tgtacaaagg cgacgtctac aacatggact accccacctt tggcgcagga   3060
agaccaggac aatttggtga cattcaaagt cgtacaccgg aaagtaaaga cgtttatgcc   3120
aacactcagt tggtactaca gaggccagca gcaggcacgg tacatgtacc atactctcag   3180
gcaccatctg gcttcaagta ttggctgaag gaacgaggag catcgctaca gcacacggca   3240
ccgttcggtt gccagattgc gacaaacccg gtaagagctg taaattgcgc tgtggggaac   3300
```

| | |
|---|---|
| ataccaattt ccatcgacat accggatgcg gcctttacta gggttgtcga tgcaccctct | 3360 |
| gtaacggaca tgtcatgcga agtaccagcc tgcactcact cctccgactt tgggggcgtc | 3420 |
| gccatcatca aatacacagc tagcaagaaa ggtaaatgtg cagtacattc gatgaccaac | 3480 |
| gccgttacca ttcgagaagc cgacgtagaa gtagagggga actcccagct gcaaatatcc | 3540 |
| ttctcaacag ccctggcaag cgccgagttt cgcgtgcaag tgtgctccac acaagtacac | 3600 |
| tgcgcagccg catgccaccc tccaaaggac cacatagtca attacccagc atcacacacc | 3660 |
| acccttgggg tccaggatat atccacaacg gcaatgtctt gggtgcagaa gattacggga | 3720 |
| ggagtaggat taattgttgc tgttgctgcc ttaattttaa ttgtggtgct atgcgtgtcg | 3780 |
| tttagcaggc ac | 3792 |

<210> SEQ ID NO 32
<211> LENGTH: 3816
<212> TYPE: DNA
<213> ORGANISM: Artificial Sequence
<220> FEATURE:
<223> OTHER INFORMATION: Synthetic polynucleotide

<400> SEQUENCE: 32

| | |
|---|---|
| atgttcccgt tccagccaat gtatccgatg cagccaatgc cctatcgcaa cccgttcgcg | 60 |
| gccccgcgca ggccctggtt ccccagaacc gacccttttc tggcgatgca ggtgcaggaa | 120 |
| ttaacccgct cgatggctaa cctgacgttc aagcaacgcc gggacgcgcc acctgagggg | 180 |
| ccatccgcta ataaaccgaa gaaggaggcc tcgcaaaaac agaaagggg aggccaaggg | 240 |
| aagaagaaga agaaccaagg gaagaagaag gctaagacag gccgcctaa tccgaaggca | 300 |
| cagaatggaa acaagaagaa gaccaacaag aaaccaggca agagacagcg catggtcatg | 360 |
| aaattggaat ctgacaagac gttcccaatc atgttggaag ggaagataaa cggctacgct | 420 |
| tgtgtggtcg gagggaagtt attcaggccg atgcatgtgg aaggcaagat cgacaacgac | 480 |
| gttctggccg cgcttaagac gaagaaagca tccaaatacg atcttgagta tgcagatgtg | 540 |
| ccacagaaca tgcgggccga tacattcaaa tacacccatg agaaacccca aggctattac | 600 |
| agctggcatc atgagcagt ccaatatgaa atgggcgtt tcacggtgcc gaaaggagtt | 660 |
| ggggccaagg gagacagcgg acgacccatt ctggataacc agggacgggt ggtcgctatt | 720 |
| gtgctgggag gtgtgaatga aggatctagg acagcccttt cagtcgtcat gtggaacgag | 780 |
| aagggagtta ccgtgaagta tactccagag aactgcgagc aatggtcact agtgaccacc | 840 |
| atgtgtctgc tcgccaatgt gacgttccca tgtgctcaac caccaatttg ctacgacaga | 900 |
| aaaccagcag agactttggc catgctcagc gttaacgttg acaacccggg ctacgatgag | 960 |
| ctgctggaag cagctgttaa gtgccccgga aggaaaagga gatccaccga ggagctgttt | 1020 |
| aatgagtata agctaacgcg cccttacatg gccagatgca tcagatgtgc agttgggagc | 1080 |
| tgccatagtc caatagcaat cgaggcagta aagagcgacg gcacgacgg ttatgttaga | 1140 |
| cttcagactt cctcgcagta tggcctggat cctccggca acttaaaggg caggaccatg | 1200 |
| cggtatgaca tgcacgggac cattaaagag ataccactac atcaagtgtc actctataca | 1260 |
| tctcgcccgt gtcacattgt ggatgggcac ggttatttcc tgcttgccag tgccccggca | 1320 |
| ggggactcca tcaccatgga atttaagaaa gattccgtca gacactcctg ctcggtgccg | 1380 |
| tatgaagtga aatttaatcc tgtaggcaga gaactctata ctcatccccc agaacacgga | 1440 |
| gtagagcaag cgtgccaagt ctacgcacat gatgcacaga acagaggagc ttatgtcgag | 1500 |

-continued

```
atgcacctcc cgggctcaga agtggacagc agtttggttt ccttgagcgg cagttccgga    1560
ggctgcatca tcagctacgg cggagccgac tactgcggcg gatcctcagt caccgtgaca    1620
cctcctgatg ggactagcgc cctggtggaa tgcgagtgtg gcggcacaaa gatctccgag    1680
accatcaaca agacaaaaca gttcagccag tgcacaaaga aggagcagtg cagagcatat    1740
cggctgcaga acgataagtg ggtgtataat tctgacaaac tgcccaaagc agcgggagcc    1800
accttaaaag gaaaactgca tgtcccattc ttgctggcag acggcaaatg caccgtgcct    1860
ctagcaccag aacctatgat aaccttcggt ttcagatcag tgtcactgaa actgcaccct    1920
aagaatccca catatctaat cacccgccaa cttgctgatg agcctcacta cacgcacgag    1980
ctcatatctg aaccagctgt taggaatttt accgtcaccg aaaaagggtg ggagtttgta    2040
tggggaaacc acccgccgaa aaggttttgg gcacaggaaa cagcacccgg aaatccacat    2100
gggctaccgc acgaggtgat aactcattat taccacagat accctatgtc caccatcctg    2160
ggtttgtcaa tttgtgccgc cattgcaacc gtttccgttg cagcgtctac ctggctgttt    2220
tgcagatcaa gagttgcgtg cctaactcct taccggctaa cacctaacgc taggatacca    2280
ttttgtctgg ctgtgctttg ctgcgcccgc actgcccggg ccgagaccac ctgggagtcc    2340
ttggatcacc tatggaacaa taaccaacag atgttctgga ttcaattgct gatccctctg    2400
gccgccttga tcgtagtgac tcgcctgctc aggtgcgtgt gctgtgtcgt gcctttttta    2460
gtcatggccg gcgccgcagg cgccggcgcc tacgagcacg cgaccacgat gccgagccaa    2520
gcgggaatct cgtataacac tatagtcaac agagcaggct acgcaccact ccctatcagc    2580
ataaccaccaa caaagatcaa gctgatacct acagtgaact tggagtacgt cacctgccac    2640
tacaaaacag gaatggattc accagccatc aaatgctgcg gatctcagga atgcactcca    2700
acttacaggc ctgatgaaca gtgcaaagtc ttcacggggg tttacccgtt catgtggggt    2760
ggtgcatatt gcttttgcga cactgagaac acccaagtca gcaaggccta cgtaatgaaa    2820
tctgacgact gccttgcgga tcatgctgaa gcatataaag cgcacacagc ctcagtgcag    2880
gcgttcctca acatcacagt gggagaacac tctattgtga ctaccgtgta tgtgaatgga    2940
gaaactcctg tgaatttcaa tggggtcaaa ataactgcag gtccgctttc cacagcttgg    3000
acacccttg atcgcaaaat cgtgcagtat gccggggaga tatataatta tgattttcct    3060
gagtatgggg caggacaacc aggagcattt ggagatatac aatccagaac agtctcaagc    3120
tctgatctgt atgccaatac caacctagtg ctgcagagac ccaaagcagg agcgatccac    3180
gtgccataca ctcaggcacc ttcgggtttt gagcaatgga gaaagataaa agctccatca    3240
ttgaaattta ccgccccttt cggatgcgaa atatatacaa accccattcg cgccgaaaac    3300
tgtgctgtag gtcaattcc attagccttt gacattcccg acgccttgtt caccagggtg    3360
tcagaaacac cgacactttc agcggccgaa tgcactctta acgagtgcgt gtattcttcc    3420
gactttggtg gatcgccac ggtcaagtac tcggccagca gtcaggcaa gtgcgcagtc    3480
catgtgccat cagggactgc taccctaaaa gaagcagcag tcgagctaac cgagcaaggg    3540
tcggcgacta tccatttctc gaccgcaaat atccacccgg agttcaggct ccaaatatgc    3600
acatcatatg ttacgtgcaa aggtgattgt cacccccga aagaccatat tgtgacacac    3660
cctcagtatc acgcccaaac atttacagcc gcggtgtcaa aaaccgcgtg acgtggtta    3720
acatccctgc tgggaggatc agccgtaatt attataattg gcttggtgct ggctactatt    3780
gtggccatgt acgtgctgac caaccagaaa cataat    3816
```

<210> SEQ ID NO 33
<211> LENGTH: 446
<212> TYPE: PRT
<213> ORGANISM: Artificial Sequence
<220> FEATURE:
<223> OTHER INFORMATION: Synthetic peptide

<400> SEQUENCE: 33

```
Ser Thr Lys Asp Asn Phe Asn Val Tyr Lys Ala Thr Arg Pro Tyr Leu
1               5                   10                  15

Ala His Cys Pro Asp Cys Gly Glu Gly His Ser Cys His Ser Pro Ile
                20                  25                  30

Ala Leu Glu Arg Ile Arg Asn Glu Ala Thr Asp Gly Thr Leu Lys Ile
            35                  40                  45

Gln Val Ser Leu Gln Ile Gly Ile Lys Thr Asp Asp Ser His Asp Trp
        50                  55                  60

Thr Lys Leu Arg Tyr Met Asp Ser His Thr Pro Ala Asp Ala Glu Arg
65                  70                  75                  80

Ala Gly Leu Leu Val Arg Thr Ser Ala Pro Cys Thr Ile Thr Gly Thr
                85                  90                  95

Met Gly His Phe Ile Leu Ala Arg Cys Pro Lys Gly Glu Thr Leu Thr
                100                 105                 110

Val Gly Phe Thr Asp Ser Arg Lys Ile Ser His Thr Cys Thr His Pro
            115                 120                 125

Phe His His Glu Pro Pro Val Ile Gly Arg Glu Arg Phe His Ser Arg
        130                 135                 140

Pro Gln His Gly Lys Glu Leu Pro Cys Ser Thr Tyr Val Gln Ser Thr
145                 150                 155                 160

Ala Ala Thr Ala Glu Glu Ile Glu Val His Met Pro Pro Asp Thr Pro
                165                 170                 175

Asp Arg Thr Leu Met Thr Gln Gln Ser Gly Asn Val Lys Ile Thr Val
            180                 185                 190

Asn Gly Gln Thr Val Arg Tyr Lys Cys Asn Cys Gly Gly Ser Gly Gly
        195                 200                 205

Leu Asn Trp Tyr Arg Met Ser Pro Ser Asn Gln Thr Asp Lys Leu Ala
        210                 215                 220

Ala Phe Gly Gly Ser Asn Glu Gly Leu Thr Thr Thr Asp Lys Val Ile
225                 230                 235                 240

Asn Asn Cys Lys Ile Asp Gln Cys His Ala Ala Val Thr Asn His Lys
                245                 250                 255

Asn Trp Gln Tyr Asn Ser Pro Leu Val Pro Arg Asn Ala Glu Leu Gly
            260                 265                 270

Asp Arg Lys Gly Lys Ile His Ile Pro Phe Pro Leu Ala Asn Val Thr
        275                 280                 285

Cys Arg Val Pro Lys Ala Arg Asn Pro Thr Val Thr Tyr Gly Lys Asn
    290                 295                 300

Gln Val Thr Met Leu Leu Tyr Pro Asp His Pro Thr Leu Leu Ser Tyr
305                 310                 315                 320

Arg Asn Met Gly Gln Glu Pro Asn Tyr His Glu Glu Trp Val Thr His
                325                 330                 335

Lys Lys Glu Val Thr Leu Thr Val Pro Thr Glu Gly Leu Glu Val Thr
            340                 345                 350

Trp Gly Asn Asn Glu Pro Tyr Lys Tyr Trp Pro Gln Met Ser Thr Asn
        355                 360                 365

Gly Thr Ala His Gly His Pro His Glu Ile Ile Leu Tyr Tyr Tyr Glu
```

```
              370                 375                 380
Leu Tyr Pro Thr Met Thr Val Ile Val Ser Val Ala Ser Phe Val
385                 390                 395                 400

Leu Leu Ser Met Val Gly Thr Ala Val Gly Met Cys Val Cys Ala Arg
                405                 410                 415

Arg Arg Cys Ile Thr Pro Tyr Glu Leu Thr Pro Gly Ala Thr Val Pro
                420                 425                 430

Phe Leu Leu Ser Leu Leu Cys Cys Val Arg Thr Thr Lys Ala
            435                 440                 445

<210> SEQ ID NO 34
<211> LENGTH: 440
<212> TYPE: PRT
<213> ORGANISM: Artificial Sequence
<220> FEATURE:
<223> OTHER INFORMATION: Synthetic peptide

<400> SEQUENCE: 34

Ser Thr Lys Asp Asn Phe Asn Val Tyr Lys Ala Thr Arg Pro Tyr Leu
1               5                   10                  15

Ala His Cys Pro Asp Cys Gly Glu Gly His Ser Cys His Ser Pro Ile
                20                  25                  30

Ala Leu Glu Arg Ile Arg Asn Glu Ala Thr Asp Gly Thr Leu Lys Ile
            35                  40                  45

Gln Val Ser Leu Gln Ile Gly Ile Lys Thr Asp Asp Ser His Asp Trp
        50                  55                  60

Thr Lys Leu Arg Tyr Met Asp Ser His Thr Pro Ala Asp Ala Glu Arg
65                  70                  75                  80

Ala Gly Leu Leu Val Arg Thr Ser Ala Pro Cys Thr Ile Thr Gly Thr
                85                  90                  95

Met Gly His Phe Ile Leu Ala Arg Cys Pro Lys Gly Glu Thr Leu Thr
                100                 105                 110

Val Gly Phe Thr Asp Ser Arg Lys Ile Ser His Thr Cys Thr His Pro
            115                 120                 125

Phe His His Glu Pro Pro Val Ile Gly Arg Glu Arg Phe His Ser Arg
        130                 135                 140

Pro Gln His Gly Lys Glu Leu Pro Cys Ser Thr Tyr Val Gln Ser Thr
145                 150                 155                 160

Ala Ala Thr Ala Glu Glu Ile Glu Val His Met Pro Pro Asp Thr Pro
                165                 170                 175

Asp Arg Thr Leu Met Thr Gln Gln Ser Gly Asn Val Lys Ile Thr Val
            180                 185                 190

Asn Gly Gln Thr Val Arg Tyr Lys Cys Asn Cys Gly Gly Ser Gly Gly
        195                 200                 205

Gly Ala Ile Ser Leu His Pro Lys Ala Lys Ile Glu Glu Ser Gly Ser
    210                 215                 220

Asn Glu Gly Leu Thr Thr Thr Asp Lys Val Ile Asn Asn Cys Lys Ile
225                 230                 235                 240

Asp Gln Cys His Ala Ala Val Thr Asn His Lys Asn Trp Gln Tyr Asn
                245                 250                 255

Ser Pro Leu Val Pro Arg Asn Ala Glu Leu Gly Asp Arg Lys Gly Lys
            260                 265                 270

Ile His Ile Pro Phe Pro Leu Ala Asn Val Thr Cys Arg Val Pro Lys
        275                 280                 285

Ala Arg Asn Pro Thr Val Thr Tyr Gly Lys Asn Gln Val Thr Met Leu
```

```
              290                 295                 300
Leu Tyr Pro Asp His Pro Thr Leu Leu Ser Tyr Arg Asn Met Gly Gln
305                 310                 315                 320

Glu Pro Asn Tyr His Glu Glu Trp Val Thr His Lys Lys Glu Val Thr
                325                 330                 335

Leu Thr Val Pro Thr Glu Gly Leu Glu Val Thr Trp Gly Asn Asn Glu
                340                 345                 350

Pro Tyr Lys Tyr Trp Pro Gln Met Ser Thr Asn Gly Thr Ala His Gly
                355                 360                 365

His Pro His Glu Ile Ile Leu Tyr Tyr Tyr Glu Leu Tyr Pro Thr Met
                370                 375                 380

Thr Val Val Ile Val Ser Val Ala Ser Phe Val Leu Leu Ser Met Val
385                 390                 395                 400

Gly Thr Ala Val Gly Met Cys Val Cys Ala Arg Arg Arg Cys Ile Thr
                405                 410                 415

Pro Tyr Glu Leu Thr Pro Gly Ala Thr Val Pro Phe Leu Leu Ser Leu
                420                 425                 430

Leu Cys Cys Val Arg Thr Thr Lys
        435                 440

<210> SEQ ID NO 35
<211> LENGTH: 443
<212> TYPE: PRT
<213> ORGANISM: Artificial Sequence
<220> FEATURE:
<223> OTHER INFORMATION: Synthetic peptide

<400> SEQUENCE: 35

Ser Thr Lys Asp Asn Phe Asn Val Tyr Lys Ala Thr Arg Pro Tyr Leu
1               5                   10                  15

Ala His Cys Pro Asp Cys Gly Glu Gly His Ser Cys His Ser Pro Ile
                20                  25                  30

Ala Leu Glu Arg Ile Arg Asn Glu Ala Thr Asp Gly Thr Leu Lys Ile
                35                  40                  45

Gln Val Ser Leu Gln Ile Gly Ile Lys Thr Asp Ser His Asp Trp
50                  55                  60

Thr Lys Leu Arg Tyr Met Asp Ser His Thr Pro Ala Asp Ala Glu Arg
65                  70                  75                  80

Ala Gly Leu Leu Val Arg Thr Ser Ala Pro Cys Thr Ile Thr Gly Thr
                85                  90                  95

Met Gly His Phe Ile Leu Ala Arg Cys Pro Lys Gly Glu Thr Leu Thr
                100                 105                 110

Val Gly Phe Thr Asp Ser Arg Lys Ile Ser His Thr Cys Thr His Pro
                115                 120                 125

Phe His His Glu Pro Pro Val Ile Gly Arg Glu Arg Phe His Ser Arg
                130                 135                 140

Pro Gln His Gly Lys Glu Leu Pro Cys Ser Thr Tyr Val Gln Ser Thr
145                 150                 155                 160

Ala Ala Thr Ala Glu Glu Ile Glu Val His Met Pro Pro Asp Thr Pro
                165                 170                 175

Asp Arg Thr Leu Met Thr Gln Gln Ser Gly Asn Val Lys Ile Thr Val
                180                 185                 190

Asn Gly Gln Thr Val Arg Tyr Lys Cys Asn Cys Gly Gly Ser Gly Gly
                195                 200                 205

Cys Gly Ala Ile Ser Leu His Pro Lys Ala Lys Ile Glu Glu Cys Gly
```

Gly Ser Asn Glu Gly Leu Thr Thr Thr Asp Lys Val Ile Asn Asn Cys
225                 230                 235                 240

Lys Ile Asp Gln Cys His Ala Ala Val Thr Asn His Lys Asn Trp Gln
                245                 250                 255

Tyr Asn Ser Pro Leu Val Pro Arg Asn Ala Glu Leu Gly Asp Arg Lys
            260                 265                 270

Gly Lys Ile His Ile Pro Phe Pro Leu Ala Asn Val Thr Cys Arg Val
        275                 280                 285

Pro Lys Ala Arg Asn Pro Thr Val Thr Tyr Gly Lys Asn Gln Val Thr
290                 295                 300

Met Leu Leu Tyr Pro Asp His Pro Thr Leu Leu Ser Tyr Arg Asn Met
305                 310                 315                 320

Gly Gln Glu Pro Asn Tyr His Glu Glu Trp Val Thr His Lys Lys Glu
                325                 330                 335

Val Thr Leu Thr Val Pro Thr Glu Gly Leu Glu Val Thr Trp Gly Asn
            340                 345                 350

Asn Glu Pro Tyr Lys Tyr Trp Pro Gln Met Ser Thr Asn Gly Thr Ala
        355                 360                 365

His Gly His Pro His Glu Ile Ile Leu Tyr Tyr Glu Leu Tyr Pro
370                 375                 380

Thr Met Thr Val Val Ile Val Ser Val Ala Ser Phe Val Leu Leu Ser
385                 390                 395                 400

Met Val Gly Thr Ala Val Gly Met Cys Val Cys Ala Arg Arg Arg Cys
                405                 410                 415

Ile Thr Pro Tyr Glu Leu Thr Pro Gly Ala Thr Val Pro Phe Leu Leu
            420                 425                 430

Ser Leu Leu Cys Cys Val Arg Thr Thr Lys Ala
        435                 440

<210> SEQ ID NO 36
<211> LENGTH: 439
<212> TYPE: PRT
<213> ORGANISM: Artificial Sequence
<220> FEATURE:
<223> OTHER INFORMATION: Synthetic peptide

<400> SEQUENCE: 36

Ser Thr Lys Asp Asn Phe Asn Val Tyr Lys Ala Thr Arg Pro Tyr Leu
1               5                   10                  15

Ala His Cys Pro Asp Cys Gly Glu Gly His Ser Cys His Ser Pro Ile
                20                  25                  30

Ala Leu Glu Arg Ile Arg Asn Glu Ala Thr Asp Gly Thr Leu Lys Ile
            35                  40                  45

Gln Val Ser Leu Gln Ile Gly Ile Lys Thr Asp Ser His Asp Trp
        50                  55                  60

Thr Lys Leu Arg Tyr Met Asp Ser His Thr Pro Ala Asp Ala Glu Arg
65                  70                  75                  80

Ala Gly Leu Leu Val Arg Thr Ser Ala Pro Cys Thr Ile Thr Gly Thr
                85                  90                  95

Met Gly His Phe Ile Leu Ala Arg Cys Pro Lys Gly Glu Thr Leu Thr
            100                 105                 110

Val Gly Phe Thr Asp Ser Arg Lys Ile Ser His Thr Cys Thr His Pro
        115                 120                 125

Phe His His Glu Pro Pro Val Ile Gly Arg Glu Arg Phe His Ser Arg 130                 135                 140
Pro Gln His Gly Lys Glu Leu Pro Cys Ser Thr Tyr Val Gln Ser Thr
145                 150                 155                 160

Ala Ala Thr Ala Glu Glu Ile Glu Val His Met Pro Pro Asp Thr Pro
                165                 170                 175

Asp Arg Thr Leu Met Thr Gln Gln Ser Gly Asn Val Lys Ile Thr Val
            180                 185                 190

Asn Gly Gln Thr Val Arg Tyr Lys Cys Asn Cys Gly Gly Ser Gly Gly
            195                 200                 205

Cys Ile Ile Ser Tyr Gly Gly Ala Asp Tyr Cys Gly Gly Ser Asn Glu
        210                 215                 220

Gly Leu Thr Thr Thr Asp Lys Val Ile Asn Asn Cys Lys Ile Asp Gln
225                 230                 235                 240

Cys His Ala Ala Val Thr Asn His Lys Asn Trp Gln Tyr Asn Ser Pro
                245                 250                 255

Leu Val Pro Arg Asn Ala Glu Leu Gly Asp Arg Lys Gly Lys Ile His
            260                 265                 270

Ile Pro Phe Pro Leu Ala Asn Val Thr Cys Arg Val Pro Lys Ala Arg
        275                 280                 285

Asn Pro Thr Val Thr Tyr Gly Lys Asn Gln Val Thr Met Leu Leu Tyr
        290                 295                 300

Pro Asp His Pro Thr Leu Leu Ser Tyr Arg Asn Met Gly Gln Glu Pro
305                 310                 315                 320

Asn Tyr His Glu Glu Trp Val Thr His Lys Lys Glu Val Thr Leu Thr
                325                 330                 335

Val Pro Thr Glu Gly Leu Glu Val Thr Trp Gly Asn Asn Glu Pro Tyr
            340                 345                 350

Lys Tyr Trp Pro Gln Met Ser Thr Asn Gly Thr Ala His Gly His Pro
            355                 360                 365

His Glu Ile Ile Leu Tyr Tyr Tyr Glu Leu Tyr Pro Thr Met Thr Val
        370                 375                 380

Val Ile Val Ser Val Ala Ser Phe Val Leu Leu Ser Met Val Gly Thr
385                 390                 395                 400

Ala Val Gly Met Cys Val Cys Ala Arg Arg Arg Cys Ile Thr Pro Tyr
                405                 410                 415

Glu Leu Thr Pro Gly Ala Thr Val Pro Phe Leu Leu Ser Leu Leu Cys
            420                 425                 430

Cys Val Arg Thr Thr Lys Ala
        435

<210> SEQ ID NO 37
<211> LENGTH: 439
<212> TYPE: PRT
<213> ORGANISM: Chikungunya virus

<400> SEQUENCE: 37

Tyr Glu His Val Thr Val Ile Pro Asn Thr Val Gly Val Pro Tyr Lys
1               5                   10                  15

Thr Leu Val Asn Arg Pro Gly Tyr Ser Pro Met Val Leu Glu Met Glu
            20                  25                  30

Leu Gln Ser Val Thr Leu Glu Pro Thr Leu Ser Leu Asp Tyr Ile Thr
        35                  40                  45

Cys Glu Tyr Lys Thr Val Ile Pro Ser Pro Tyr Val Lys Cys Cys Gly
    50                  55                  60

Thr Ala Glu Cys Lys Asp Lys Ser Leu Pro Asp Tyr Ser Cys Lys Val
65                  70                  75                  80

Phe Thr Gly Val Tyr Pro Phe Met Trp Gly Gly Ala Tyr Cys Phe Cys
                85                  90                  95

Asp Ala Glu Asn Thr Gln Leu Ser Glu Ala His Val Glu Lys Ser Glu
            100                 105                 110

Ser Cys Lys Thr Glu Phe Ala Ser Ala Tyr Arg Ala His Thr Ala Ser
            115                 120                 125

Ala Ser Ala Lys Leu Arg Val Leu Tyr Gln Gly Asn Asn Ile Thr Val
130                 135                 140

Ala Ala Tyr Ala Asn Gly Asp His Ala Val Thr Val Lys Asp Ala Lys
145                 150                 155                 160

Phe Val Val Gly Pro Met Ser Ser Ala Trp Thr Pro Phe Asp Asn Lys
                165                 170                 175

Ile Val Val Tyr Lys Gly Asp Val Tyr Asn Met Asp Tyr Pro Pro Phe
                180                 185                 190

Gly Ala Gly Arg Pro Gly Gln Phe Gly Asp Ile Gln Ser Arg Thr Pro
            195                 200                 205

Glu Ser Lys Asp Val Tyr Ala Asn Thr Gln Leu Val Leu Gln Arg Pro
210                 215                 220

Ala Ala Gly Thr Val His Val Pro Tyr Ser Gln Ala Pro Ser Gly Phe
225                 230                 235                 240

Lys Tyr Trp Leu Lys Glu Arg Gly Ala Ser Leu Gln His Thr Ala Pro
                245                 250                 255

Phe Gly Cys Gln Ile Ala Thr Asn Pro Val Arg Ala Val Asn Cys Ala
            260                 265                 270

Val Gly Asn Ile Pro Ile Ser Ile Asp Ile Pro Asp Ala Ala Phe Thr
            275                 280                 285

Arg Val Val Asp Ala Pro Ser Val Thr Asp Met Ser Cys Glu Val Pro
290                 295                 300

Ala Cys Thr His Ser Ser Asp Phe Gly Gly Val Ala Ile Ile Lys Tyr
305                 310                 315                 320

Thr Ala Ser Lys Lys Gly Lys Cys Ala Val His Ser Met Thr Asn Ala
                325                 330                 335

Val Thr Ile Arg Glu Ala Asp Val Glu Val Glu Gly Asn Ser Gln Leu
            340                 345                 350

Gln Ile Ser Phe Ser Thr Ala Leu Ala Ser Ala Glu Phe Arg Val Gln
            355                 360                 365

Val Cys Ser Thr Gln Val His Cys Ala Ala Cys His Pro Pro Lys
370                 375                 380

Asp His Ile Val Asn Tyr Pro Ala Ser His Thr Thr Leu Gly Val Gln
385                 390                 395                 400

Asp Ile Ser Thr Thr Ala Met Ser Trp Val Gln Lys Ile Thr Gly Gly
            405                 410                 415

Val Gly Leu Ile Val Ala Val Ala Ala Leu Ile Leu Ile Val Val Leu
            420                 425                 430

Cys Val Ser Phe Ser Arg His
        435

<210> SEQ ID NO 38
<211> LENGTH: 261
<212> TYPE: PRT
<213> ORGANISM: Chikungunya virus

<400> SEQUENCE: 38

```
Met Glu Phe Ile Pro Thr Gln Thr Phe Tyr Asn Arg Arg Tyr Gln Pro
1               5                   10                  15

Arg Pro Trp Ala Pro Arg Pro Thr Ile Gln Val Ile Arg Pro Arg Pro
            20                  25                  30

Arg Pro Gln Arg Gln Ala Gly Gln Leu Ala Gln Leu Ile Ser Ala Val
        35                  40                  45

Asn Lys Leu Thr Met Arg Ala Val Pro Gln Gln Lys Pro Arg Arg Asn
50                  55                  60

Arg Lys Asn Lys Lys Gln Arg Gln Lys Lys Gln Ala Pro Gln Asn Asp
65                  70                  75                  80

Pro Lys Gln Lys Gln Pro Pro Gln Lys Pro Ala Gln Lys Lys
                85                  90                  95

Lys Lys Pro Gly Arg Arg Glu Arg Met Cys Met Lys Ile Glu Asn Asp
            100                 105                 110

Cys Ile Phe Glu Val Lys His Glu Gly Lys Val Met Gly Tyr Ala Cys
            115                 120                 125

Leu Val Gly Asp Lys Val Met Lys Pro Ala His Val Lys Gly Thr Ile
        130                 135                 140

Asp Asn Ala Asp Leu Ala Lys Leu Ala Phe Lys Arg Ser Ser Lys Tyr
145                 150                 155                 160

Asp Leu Glu Cys Ala Gln Ile Pro Val His Met Lys Ser Asp Ala Ser
            165                 170                 175

Lys Phe Thr His Glu Lys Pro Glu Gly Tyr Tyr Asn Trp His His Gly
            180                 185                 190

Ala Val Gln Tyr Ser Gly Gly Arg Phe Thr Ile Pro Thr Gly Ala Gly
        195                 200                 205

Lys Pro Gly Asp Ser Gly Arg Pro Ile Phe Asp Asn Lys Gly Arg Val
    210                 215                 220

Val Ala Ile Val Leu Gly Gly Ala Asn Glu Gly Ala Arg Thr Ala Leu
225                 230                 235                 240

Ser Val Val Thr Trp Asn Lys Asp Ile Val Thr Lys Ile Thr Pro Glu
            245                 250                 255

Gly Ala Glu Glu Trp
            260

<210> SEQ ID NO 39
<211> LENGTH: 447
<212> TYPE: PRT
<213> ORGANISM: Artificial Sequence
<220> FEATURE:
<223> OTHER INFORMATION: Synthetic peptide

<400> SEQUENCE: 39

Ser Thr Glu Glu Leu Phe Asn Glu Tyr Lys Leu Thr Arg Pro Tyr Met
1               5                   10                  15

Ala Arg Cys Ile Arg Cys Ala Val Gly Ser Cys His Ser Pro Ile Ala
            20                  25                  30

Ile Glu Ala Val Lys Ser Asp Gly His Asp Gly Tyr Val Arg Leu Gln
        35                  40                  45

Thr Ser Ser Gln Tyr Gly Leu Asp Ser Ser Gly Asn Leu Lys Gly Arg
    50                  55                  60

Thr Met Arg Tyr Asp Met His Gly Thr Ile Lys Glu Ile Pro Leu His
65                  70                  75                  80

Gln Val Ser Leu Tyr Thr Ser Arg Pro Cys His Ile Val Asp Gly His
            85                  90                  95
```

```
Gly Tyr Phe Leu Leu Ala Arg Cys Pro Ala Gly Asp Ser Ile Thr Met
            100                 105                 110
Glu Phe Lys Lys Asp Ser Val Arg His Ser Cys Ser Val Pro Tyr Glu
        115                 120                 125
Val Lys Phe Asn Pro Val Gly Arg Glu Leu Tyr Thr His Pro Pro Glu
    130                 135                 140
His Gly Val Glu Gln Ala Cys Gln Val Tyr Ala His Asp Ala Gln Asn
145                 150                 155                 160
Arg Gly Ala Tyr Val Glu Met His Leu Pro Gly Ser Glu Val Asp Ser
                165                 170                 175
Ser Leu Val Ser Leu Ser Gly Ser Gly Gly Leu Asn Trp Tyr Arg
            180                 185                 190
Met Ser Pro Ser Asn Gln Thr Asp Lys Leu Ala Ala Phe Gly Gly Ser
        195                 200                 205
Ser Val Thr Val Thr Pro Pro Asp Gly Thr Ser Ala Leu Val Glu Cys
    210                 215                 220
Glu Cys Gly Gly Thr Lys Ile Ser Glu Thr Ile Asn Lys Thr Lys Gln
225                 230                 235                 240
Phe Ser Gln Cys Thr Lys Glu Gln Cys Arg Ala Tyr Arg Leu Gln
                245                 250                 255
Asn Asp Lys Trp Val Tyr Asn Ser Asp Lys Leu Pro Lys Ala Ala Gly
            260                 265                 270
Ala Thr Leu Lys Gly Lys Leu His Val Pro Phe Leu Leu Ala Asp Gly
        275                 280                 285
Lys Cys Thr Val Pro Leu Ala Pro Glu Pro Met Ile Thr Phe Gly Phe
    290                 295                 300
Arg Ser Val Ser Leu Lys Leu His Pro Lys Asn Pro Thr Tyr Leu Ile
305                 310                 315                 320
Thr Arg Gln Leu Ala Asp Glu Pro His Tyr Thr His Glu Leu Ile Ser
                325                 330                 335
Glu Pro Ala Val Arg Asn Phe Thr Val Thr Glu Lys Gly Trp Glu Phe
            340                 345                 350
Val Trp Gly Asn His Pro Pro Lys Arg Phe Trp Ala Gln Glu Thr Ala
        355                 360                 365
Pro Gly Asn Pro His Gly Leu Pro His Glu Val Ile Thr His Tyr Tyr
    370                 375                 380
His Arg Tyr Pro Met Ser Thr Ile Leu Gly Leu Ser Ile Cys Ala Ala
385                 390                 395                 400
Ile Ala Thr Val Ser Val Ala Ala Ser Thr Trp Leu Phe Cys Arg Ser
                405                 410                 415
Arg Val Ala Cys Leu Thr Pro Tyr Arg Leu Thr Pro Asn Ala Arg Ile
            420                 425                 430
Pro Phe Cys Leu Ala Val Leu Cys Cys Ala Arg Thr Ala Arg Ala
        435                 440                 445

<210> SEQ ID NO 40
<211> LENGTH: 442
<212> TYPE: PRT
<213> ORGANISM: Artificial Sequence
<220> FEATURE:
<223> OTHER INFORMATION: Synthetic peptide

<400> SEQUENCE: 40

Ser Thr Glu Glu Leu Phe Asn Glu Tyr Lys Leu Thr Arg Pro Tyr Met
1               5                   10                  15
```

-continued

```
Ala Arg Cys Ile Arg Cys Ala Val Gly Ser Cys His Ser Pro Ile Ala
            20                  25                  30

Ile Glu Ala Val Lys Ser Asp Gly His Asp Gly Tyr Val Arg Leu Gln
        35                  40                  45

Thr Ser Ser Gln Tyr Gly Leu Asp Ser Ser Gly Asn Leu Lys Gly Arg
    50                  55                  60

Thr Met Arg Tyr Asp Met His Gly Thr Ile Lys Glu Ile Pro Leu His
65                  70                  75                  80

Gln Val Ser Leu Tyr Thr Ser Arg Pro Cys His Ile Val Asp Gly His
                85                  90                  95

Gly Tyr Phe Leu Leu Ala Arg Cys Pro Ala Gly Asp Ser Ile Thr Met
            100                 105                 110

Glu Phe Lys Lys Asp Ser Val Arg His Ser Cys Ser Val Pro Tyr Glu
        115                 120                 125

Val Lys Phe Asn Pro Val Gly Arg Glu Leu Tyr Thr His Pro Pro Glu
    130                 135                 140

His Gly Val Glu Gln Ala Cys Gln Val Tyr Ala His Asp Ala Gln Asn
145                 150                 155                 160

Arg Gly Ala Tyr Val Glu Met His Leu Pro Gly Ser Glu Val Asp Ser
                165                 170                 175

Ser Leu Val Ser Leu Ser Gly Ser Gly Gly Ala Ile Ser Leu
            180                 185                 190

His Pro Lys Ala Lys Ile Glu Glu Ser Gly Ser Ser Val Thr Val Thr
        195                 200                 205

Pro Pro Asp Gly Thr Ser Ala Leu Val Glu Cys Glu Cys Gly Gly Thr
    210                 215                 220

Lys Ile Ser Glu Thr Ile Asn Lys Thr Lys Gln Phe Ser Gln Cys Thr
225                 230                 235                 240

Lys Lys Glu Gln Cys Arg Ala Tyr Arg Leu Gln Asn Asp Lys Trp Val
                245                 250                 255

Tyr Asn Ser Asp Lys Leu Pro Lys Ala Ala Gly Ala Thr Leu Lys Gly
            260                 265                 270

Lys Leu His Val Pro Phe Leu Leu Ala Asp Gly Lys Cys Thr Val Pro
        275                 280                 285

Leu Ala Pro Glu Pro Met Ile Thr Phe Gly Phe Arg Ser Val Ser Leu
    290                 295                 300

Lys Leu His Pro Lys Asn Pro Thr Tyr Leu Ile Thr Arg Gln Leu Ala
305                 310                 315                 320

Asp Glu Pro His Tyr Thr His Glu Leu Ile Ser Glu Pro Ala Val Arg
                325                 330                 335

Asn Phe Thr Val Thr Glu Lys Gly Trp Glu Phe Val Trp Gly Asn His
            340                 345                 350

Pro Pro Lys Arg Phe Trp Ala Gln Glu Thr Ala Pro Gly Asn Pro His
        355                 360                 365

Gly Leu Pro His Glu Val Ile Thr His Tyr Tyr His Arg Tyr Pro Met
    370                 375                 380

Ser Thr Ile Leu Gly Leu Ser Ile Cys Ala Ala Ile Ala Thr Val Ser
385                 390                 395                 400

Val Ala Ala Ser Thr Trp Leu Phe Cys Arg Ser Arg Val Ala Cys Leu
                405                 410                 415

Thr Pro Tyr Arg Leu Thr Pro Asn Ala Arg Ile Pro Phe Cys Leu Ala
            420                 425                 430
```

Val Leu Cys Cys Ala Arg Thr Ala Arg Ala
        435                 440

<210> SEQ ID NO 41
<211> LENGTH: 444
<212> TYPE: PRT
<213> ORGANISM: Artificial Sequence
<220> FEATURE:
<223> OTHER INFORMATION: Synthetic peptide

<400> SEQUENCE: 41

Ser Thr Glu Glu Leu Phe Asn Glu Tyr Lys Leu Thr Arg Pro Tyr Met
1               5                   10                  15

Ala Arg Cys Ile Arg Cys Ala Val Gly Ser Cys His Ser Pro Ile Ala
            20                  25                  30

Ile Glu Ala Val Lys Ser Asp Gly His Asp Gly Tyr Val Arg Leu Gln
        35                  40                  45

Thr Ser Ser Gln Tyr Gly Leu Asp Ser Ser Gly Asn Leu Lys Gly Arg
50                  55                  60

Thr Met Arg Tyr Asp Met His Gly Thr Ile Lys Glu Ile Pro Leu His
65              70                  75                  80

Gln Val Ser Leu Tyr Thr Ser Arg Pro Cys His Ile Val Asp Gly His
                85                  90                  95

Gly Tyr Phe Leu Leu Ala Arg Cys Pro Ala Gly Asp Ser Ile Thr Met
            100                 105                 110

Glu Phe Lys Lys Asp Ser Val Arg His Ser Cys Ser Val Pro Tyr Glu
        115                 120                 125

Val Lys Phe Asn Pro Val Gly Arg Glu Leu Tyr Thr His Pro Pro Glu
130                 135                 140

His Gly Val Glu Gln Ala Cys Gln Val Tyr Ala His Asp Ala Gln Asn
145                 150                 155                 160

Arg Gly Ala Tyr Val Glu Met His Leu Pro Gly Ser Glu Val Asp Ser
                165                 170                 175

Ser Leu Val Ser Leu Ser Gly Ser Gly Gly Cys Gly Ala Ile Ser
            180                 185                 190

Leu His Pro Lys Ala Lys Ile Glu Glu Cys Gly Gly Ser Ser Val Thr
        195                 200                 205

Val Thr Pro Pro Asp Gly Thr Ser Ala Leu Val Glu Cys Glu Cys Gly
210                 215                 220

Gly Thr Lys Ile Ser Glu Thr Ile Asn Lys Thr Lys Gln Phe Ser Gln
225                 230                 235                 240

Cys Thr Lys Lys Glu Gln Cys Arg Ala Tyr Arg Leu Gln Asn Asp Lys
                245                 250                 255

Trp Val Tyr Asn Ser Asp Lys Leu Pro Lys Ala Gly Ala Thr Leu
            260                 265                 270

Lys Gly Lys Leu His Val Pro Phe Leu Leu Ala Asp Gly Lys Cys Thr
        275                 280                 285

Val Pro Leu Ala Pro Glu Pro Met Ile Thr Phe Gly Phe Arg Ser Val
290                 295                 300

Ser Leu Lys Leu His Pro Lys Asn Pro Thr Tyr Leu Ile Thr Arg Gln
305                 310                 315                 320

Leu Ala Asp Glu Pro His Tyr Thr His Glu Leu Ile Ser Glu Pro Ala
                325                 330                 335

Val Arg Asn Phe Thr Val Thr Glu Lys Gly Trp Glu Phe Val Trp Gly
            340                 345                 350

```
Asn His Pro Pro Lys Arg Phe Trp Ala Gln Glu Thr Ala Pro Gly Asn
        355                 360                 365

Pro His Gly Leu Pro His Glu Val Ile Thr His Tyr Tyr His Arg Tyr
370                 375                 380

Pro Met Ser Thr Ile Leu Gly Leu Ser Ile Cys Ala Ala Ile Ala Thr
385                 390                 395                 400

Val Ser Val Ala Ala Ser Thr Trp Leu Phe Cys Arg Ser Arg Val Ala
                405                 410                 415

Cys Leu Thr Pro Tyr Arg Leu Thr Pro Asn Ala Arg Ile Pro Phe Cys
                420                 425                 430

Leu Ala Val Leu Cys Cys Ala Arg Thr Ala Arg Ala
            435                 440

<210> SEQ ID NO 42
<211> LENGTH: 440
<212> TYPE: PRT
<213> ORGANISM: Artificial Sequence
<220> FEATURE:
<223> OTHER INFORMATION: Synthetic peptide

<400> SEQUENCE: 42

Ser Thr Glu Glu Leu Phe Asn Glu Tyr Lys Leu Thr Arg Pro Tyr Met
1               5                   10                  15

Ala Arg Cys Ile Arg Cys Ala Val Gly Ser Cys His Ser Pro Ile Ala
                20                  25                  30

Ile Glu Ala Val Lys Ser Asp Gly His Asp Gly Tyr Val Arg Leu Gln
            35                  40                  45

Thr Ser Ser Gln Tyr Gly Leu Asp Ser Ser Gly Asn Leu Lys Gly Arg
    50                  55                  60

Thr Met Arg Tyr Asp Met His Gly Thr Ile Lys Glu Ile Pro Leu His
65                  70                  75                  80

Gln Val Ser Leu Tyr Thr Ser Arg Pro Cys His Ile Val Asp Gly His
                85                  90                  95

Gly Tyr Phe Leu Leu Ala Arg Cys Pro Ala Gly Asp Ser Ile Thr Met
                100                 105                 110

Glu Phe Lys Lys Asp Ser Val Arg His Ser Cys Ser Val Pro Tyr Glu
            115                 120                 125

Val Lys Phe Asn Pro Val Gly Arg Glu Leu Tyr Thr His Pro Pro Glu
    130                 135                 140

His Gly Val Glu Gln Ala Cys Gln Val Tyr Ala His Asp Ala Gln Asn
145                 150                 155                 160

Arg Gly Ala Tyr Val Glu Met His Leu Pro Gly Ser Glu Val Asp Ser
                165                 170                 175

Ser Leu Val Ser Leu Ser Gly Ser Gly Gly Cys Ile Ile Ser Tyr
                180                 185                 190

Gly Gly Ala Asp Tyr Cys Gly Gly Ser Val Thr Val Thr Pro Pro
            195                 200                 205

Asp Gly Thr Ser Ala Leu Val Glu Cys Glu Cys Gly Gly Thr Lys Ile
    210                 215                 220

Ser Glu Thr Ile Asn Lys Thr Lys Gln Phe Ser Gln Cys Thr Lys Lys
225                 230                 235                 240

Glu Gln Cys Arg Ala Tyr Arg Leu Gln Asn Asp Lys Trp Val Tyr Asn
                245                 250                 255

Ser Asp Lys Leu Pro Lys Ala Ala Gly Ala Thr Leu Lys Gly Lys Leu
            260                 265                 270
```

-continued

```
His Val Pro Phe Leu Leu Ala Asp Gly Lys Cys Thr Val Pro Leu Ala
            275                 280                 285

Pro Glu Pro Met Ile Thr Phe Gly Phe Arg Ser Val Ser Leu Lys Leu
            290                 295                 300

His Pro Lys Asn Pro Thr Tyr Leu Ile Thr Arg Gln Leu Ala Asp Glu
305                 310                 315                 320

Pro His Tyr Thr His Glu Leu Ile Ser Glu Pro Ala Val Arg Asn Phe
            325                 330                 335

Thr Val Thr Glu Lys Gly Trp Glu Phe Val Trp Gly Asn His Pro Pro
            340                 345                 350

Lys Arg Phe Trp Ala Gln Glu Thr Ala Pro Gly Asn Pro His Gly Leu
            355                 360                 365

Pro His Glu Val Ile Thr His Tyr Tyr His Arg Tyr Pro Met Ser Thr
            370                 375                 380

Ile Leu Gly Leu Ser Ile Cys Ala Ala Ile Ala Thr Val Ser Val Ala
385                 390                 395                 400

Ala Ser Thr Trp Leu Phe Cys Arg Ser Arg Val Ala Cys Leu Thr Pro
            405                 410                 415

Tyr Arg Leu Thr Pro Asn Ala Arg Ile Pro Phe Cys Leu Ala Val Leu
            420                 425                 430

Cys Cys Ala Arg Thr Ala Arg Ala
            435                 440

<210> SEQ ID NO 43
<211> LENGTH: 442
<212> TYPE: PRT
<213> ORGANISM: Venezuelan equine encephalitis virus

<400> SEQUENCE: 43

Tyr Glu His Ala Thr Thr Met Pro Ser Gln Ala Gly Ile Ser Tyr Asn
1               5                   10                  15

Thr Ile Val Asn Arg Ala Gly Tyr Ala Pro Leu Pro Ile Ser Ile Thr
            20                  25                  30

Pro Thr Lys Ile Lys Leu Ile Pro Thr Val Asn Leu Glu Tyr Val Thr
        35                  40                  45

Cys His Tyr Lys Thr Gly Met Asp Ser Pro Ala Ile Lys Cys Cys Gly
    50                  55                  60

Ser Gln Glu Cys Thr Pro Thr Tyr Arg Pro Asp Glu Gln Cys Lys Val
65                  70                  75                  80

Phe Thr Gly Val Tyr Pro Phe Met Trp Gly Gly Ala Tyr Cys Phe Cys
                85                  90                  95

Asp Thr Glu Asn Thr Gln Val Ser Lys Ala Tyr Val Met Lys Ser Asp
            100                 105                 110

Asp Cys Leu Ala Asp His Ala Glu Ala Tyr Lys Ala His Thr Ala Ser
        115                 120                 125

Val Gln Ala Phe Leu Asn Ile Thr Val Gly Glu His Ser Ile Val Thr
    130                 135                 140

Thr Val Tyr Val Asn Gly Glu Thr Pro Val Asn Phe Asn Gly Val Lys
145                 150                 155                 160

Ile Thr Ala Gly Pro Leu Ser Thr Ala Trp Thr Pro Phe Asp Arg Lys
                165                 170                 175

Ile Val Gln Tyr Ala Gly Glu Ile Tyr Asn Tyr Asp Phe Pro Glu Tyr
            180                 185                 190

Gly Ala Gly Gln Pro Gly Ala Phe Gly Asp Ile Gln Ser Arg Thr Val
        195                 200                 205
```

Ser Ser Ser Asp Leu Tyr Ala Asn Thr Asn Leu Val Leu Gln Arg Pro
    210                 215                 220

Lys Ala Gly Ala Ile His Val Pro Tyr Thr Gln Ala Pro Ser Gly Phe
225                 230                 235                 240

Glu Gln Trp Lys Lys Asp Lys Ala Pro Ser Leu Lys Phe Thr Ala Pro
                245                 250                 255

Phe Gly Cys Glu Ile Tyr Thr Asn Pro Ile Arg Ala Glu Asn Cys Ala
            260                 265                 270

Val Gly Ser Ile Pro Leu Ala Phe Asp Ile Pro Asp Ala Leu Phe Thr
        275                 280                 285

Arg Val Ser Glu Thr Pro Thr Leu Ser Ala Ala Glu Cys Thr Leu Asn
    290                 295                 300

Glu Cys Val Tyr Ser Ser Asp Phe Gly Gly Ile Ala Thr Val Lys Tyr
305                 310                 315                 320

Ser Ala Ser Lys Ser Gly Lys Cys Ala Val His Val Pro Ser Gly Thr
                325                 330                 335

Ala Thr Leu Lys Glu Ala Ala Val Glu Leu Thr Glu Gln Gly Ser Ala
            340                 345                 350

Thr Ile His Phe Ser Thr Ala Asn Ile His Pro Glu Phe Arg Leu Gln
        355                 360                 365

Ile Cys Thr Ser Tyr Val Thr Cys Lys Gly Asp Cys His Pro Pro Lys
    370                 375                 380

Asp His Ile Val Thr His Pro Gln Tyr His Ala Gln Thr Phe Thr Ala
385                 390                 395                 400

Ala Val Ser Lys Thr Ala Trp Thr Trp Leu Thr Ser Leu Leu Gly Gly
                405                 410                 415

Ser Ala Val Ile Ile Ile Gly Leu Val Leu Ala Thr Ile Val Ala
            420                 425                 430

Met Tyr Val Leu Thr Asn Gln Lys His Asn
        435                 440

<210> SEQ ID NO 44
<211> LENGTH: 275
<212> TYPE: PRT
<213> ORGANISM: Venezuelan equine encephalitis virus

<400> SEQUENCE: 44

Met Phe Pro Phe Gln Pro Met Tyr Pro Met Gln Pro Met Pro Tyr Arg
1               5                   10                  15

Asn Pro Phe Ala Ala Pro Arg Arg Pro Trp Phe Pro Arg Thr Asp Pro
                20                  25                  30

Phe Leu Ala Met Gln Val Gln Glu Leu Thr Arg Ser Met Ala Asn Leu
            35                  40                  45

Thr Phe Lys Gln Arg Arg Asp Ala Pro Pro Glu Gly Pro Ser Ala Asn
    50                  55                  60

Lys Pro Lys Lys Glu Ala Ser Gln Lys Gln Lys Gly Gly Gly Gln Gly
65                  70                  75                  80

Lys Lys Lys Lys Asn Gln Gly Lys Lys Lys Ala Lys Thr Gly Pro Pro
                85                  90                  95

Asn Pro Lys Ala Gln Asn Gly Asn Lys Lys Thr Asn Lys Lys Pro
            100                 105                 110

Gly Lys Arg Gln Arg Met Val Met Lys Leu Glu Ser Asp Lys Thr Phe
        115                 120                 125

Pro Ile Met Leu Glu Gly Lys Ile Asn Gly Tyr Ala Cys Val Val Gly

```
            130                 135                 140
Gly Lys Leu Phe Arg Pro Met His Val Glu Gly Lys Ile Asp Asn Asp
145                 150                 155                 160

Val Leu Ala Ala Leu Lys Thr Lys Lys Ala Ser Lys Tyr Asp Leu Glu
                165                 170                 175

Tyr Ala Asp Val Pro Gln Asn Met Arg Ala Asp Thr Phe Lys Tyr Thr
            180                 185                 190

His Glu Lys Pro Gln Gly Tyr Tyr Ser Trp His His Gly Ala Val Gln
        195                 200                 205

Tyr Glu Asn Gly Arg Phe Thr Val Pro Lys Gly Val Gly Ala Lys Gly
        210                 215                 220

Asp Ser Gly Arg Pro Ile Leu Asp Asn Gln Gly Arg Val Val Ala Ile
225                 230                 235                 240

Val Leu Gly Gly Val Asn Glu Gly Ser Arg Thr Ala Leu Ser Val Val
                245                 250                 255

Met Trp Asn Glu Lys Gly Val Thr Val Lys Tyr Thr Pro Glu Asn Cys
                260                 265                 270

Glu Gln Trp
        275

<210> SEQ ID NO 45
<211> LENGTH: 8467
<212> TYPE: DNA
<213> ORGANISM: Artificial Sequence
<220> FEATURE:
<223> OTHER INFORMATION: Synthetic polynucleotide

<400> SEQUENCE: 45
gaattcccat tgcatacgtt gtatccatat cataatatgt acatttatat tggctcatgt     60
ccaacattac cgccatgttg acattgatta ttgactagtt attaatagta atcaattacg    120
gggtcattag ttcatagccc atatatggag ttccgcgtta cataacttac ggtaaatggc    180
ccgcctggct gaccgcccaa cgacccccgc ccattgacgt caataatgac gtatgttccc    240
atagtaacgc caatagggac tttccattga cgtcaatggg tggagtattt acggtaaact    300
gcccacttgg cagtacatca agtgtatcat atgccaagta cgccccctat tgacgtcaat    360
gacggtaaat ggcccgcctg gcattatgcc cagtacatga ccttatggga ctttcctact    420
tggcagtaca tctacgtatt agtcatcgct attaccatgg tgatgcggtt ttggcagtac    480
atcaatgggc gtggatagcg gtttgactca cggggatttc caagtctcca ccccattgac    540
gtcaatggga gtttgttttg gcaccaaaat caacgggact ttccaaaatg tcgtaacaac    600
tccgccccat tgacgcaaat gggcggtagg cgtgtacggt gggaggtcta taagcaga     660
gctcgtttag tgaaccgtca gatcgcctgg agacgccatc cacgctgttt tgacctccat    720
agaagacacc gggaccgatc cagcctccgt taacggtgga gggcagtgta gtctgagcag    780
tactcgttgc tgccgcgcgc gccaccagac ataatagctg acagactaac agactgttcc    840
tttccatggg tcttttctgc agtcaccgtc gtcgacacgt gtgatcagat atcgcggccg    900
ccaccatgga gttcatcccg acgcaaactt tctataacag aaggtaccaa ccccgaccct    960
gggccccacg ccctacaatt caagtaatta gacctagacc acgtccacag aggcaggctg   1020
ggcaactcgc ccagctgatc tccgcagtca acaaattgac catgcgcgcg gtacctcaac   1080
agaagcctcg cagaaatcgg aaaaacaaga agcaaaggca gaagaagcag gcgccgcaaa   1140
acgacccaaa gcaaaagaag caaccaccac aaaagaagcc ggctcaaaag aagaagaaac   1200
```

```
caggccgtag ggagagaatg tgcatgaaaa ttgaaaatga ttgcatcttc gaagtcaagc    1260
atgaaggcaa agtgatgggc tacgcatgcc tggtggggga taaagtaatg aaaccagcac    1320
atgtgaaggg aactatcgac aatgccgatc tggctaaact ggcctttaag cggtcgtcta    1380
aatacgatct tgaatgtgca cagataccgg tgcacatgaa gtctgatgcc tcgaagttta    1440
cccacgagaa acccgagggg tactataact ggcatcacgg agcagtgcag tattcaggag    1500
gccggttcac tatcccgacg ggtgcaggca agcgggaga cagcggcaga ccgatcttcg    1560
acaacaaagg acgggtggtg gccatcgtcc taggaggggc caacgaaggt gcccgcacgg    1620
ccctctccgt ggtgacgtgg aacaaagaca tcgtcacaaa aattacccct gagggagccg    1680
aagagtggag cctcgccctc ccggtcttgt gcctgttggc aaacactaca ttcccctgct    1740
ctcagccgcc ttgcacaccc tgctgctacg aaaaggaacc ggaaagcacc ttgcgcatgc    1800
ttgaggacaa cgtgatgaga cccggatact accagctact aaaagcatcg ctgacttgct    1860
ctccccaccg ccaaagacgc agtactaagg acaattttaa tgtctataaa gccacaagac    1920
catatctagc tcattgtcct gactgcgag aagggcattc gtgccacagc cctatcgcat     1980
tggagcgcat cagaaatgaa gcaacggacg gaacgctgaa atccaggtc tctttgcaga     2040 tcggataaaa gacagatgac agccacgatt ggaccaagct gcgctatatg gatagccata    2100
cgccagcgga cgcggagcga gccggattgc ttgtaaggac ttcagcaccg tgcacgatca    2160
ccgggaccat gggacacttt attctcgccc gatgcccgaa aggagagacg ctgacagtgg    2220
gatttacgga cagcagaaag atcagccaca catgcacaca cccgttccat catgaaccac    2280
ctgtgatagg tagggagagg ttccactctc gaccacaaca tggtaaagag ttaccttgca    2340
gcacgtacgt gcagagcacc gctgccactg ctgaggagat agaggtgcat atgccccag    2400 atactcctga ccgcacgctg atgacgcagc agtctggcaa cgtgaagatc acagttaatg    2460
ggcagacggt gcggtacaag tgcaactgcg gtggctccgg aggactaaac tggtaccgca    2520
tgagccccag caaccagacg gacaagctgg ccgccttcgg aggatccaac gagggactga    2580
caaccacaga caaagtgatc aataactgca aaattgatca gtgccatgct gcagtcacta    2640
atcacaagaa ttggcaatac aactcccctt tagtcccgcg caacgctgaa ctcgggacc     2700 gtaaaggaaa gatccacatc ccattcccat ggcaaacgt gacttgcaga gtgccaaaag    2760
caagaaaccc tacagtaact tacgaaaaaa accaagtcac catgctgctg tatcctgacc    2820
atccgacact cttgtcttac cgtaacatgg acaggaacc aaattaccac gaggagtggg    2880
tgacacacaa gaaggaggtt accttgaccg tgcctactga gggtctggag gtcacttggg    2940
gcaacaacga accatacaag tactggccgc agatgtctac gaacggtact gctcatggtc    3000
acccacatga gaatctg tactattatg agctgtaccc cactatgact gtagtcattg       3060
tgtcggtggc ctcgttcgtg cttctgtcga tggtgggcac agcagtggga atgtgtgtgt    3120
gcgcacggcg cagatgcatt acaccatatg aattaacacc aggagccact gttcccttcc    3180
tgctcagcct gctatgctgc gtcagaacga ccaaggcggc cacatattac gaggctgcgg    3240
catatctatg gaacgaacag cagcccctgt tctggttgca ggctcttatc ccgctggccg    3300
ccttgatcgt cctgtgcaac tgtctgaac tcttgccatg ctgctgtaag accctggctt     3360
ttttagccgt aatgagcatc ggtgcccaca ctgtgagcgc gtacgaacac gtaacagtga    3420
tcccgaacac ggtgggagta ccgtataaga ctcttgtcaa cagaccgggt tacagcccca    3480
tggtgttgga gatggagcta caatcagtca ccttggaacc aacactgtca cttgactaca    3540
tcacgtgcga gtacaaaact gtcatcccct ccccgtacgt gaagtgctgt ggtacagcag    3600
```

```
agtgcaagga caagagccta ccagactaca gctgcaaggt ctttactgga gtctacccat    3660
ttatgtgggg cggcgcctac tgcttttgcg acgccgaaaa tacgcaattg agcgaggcac    3720
atgtagagaa atctgaatct tgcaaaacag agtttgcatc ggcctacaga gcccacaccg    3780
catcggcgtc ggcgaagctc cgcgtccttt accaaggaaa caacattacc gtagctgcct    3840
acgctaacgg tgaccatgcc gtcacagtaa aggacgccaa gtttgtcgtg ggcccaatgt    3900
cctccgcctg gacacctttt gacaacaaaa tcgtggtgta caaaggcgac gtctacaaca    3960
tggactaccc acctttttggc gcaggaagac caggacaatt tggtgacatt caaagtcgta    4020
caccggaaag taaagacgtt tatgccaaca ctcagttggt actacagagg ccagcagcag    4080
gcacggtaca tgtaccatac tctcaggcac catctggctt caagtattgg ctgaaggaac    4140
gaggagcatc gctacagcac acggcaccgt tcggttgcca gattgcgaca aacccggtaa    4200
gagctgtaaa ttgcgctgtg gggaacatac caatttccat cgacataccg gatgcggcct    4260
ttactagggt tgtcgatgca ccctctgtaa cggacatgtc atgcgaagta ccagcctgca    4320
ctcactcctc cgactttggg ggcgtcgcca tcatcaaata cacagctagc aagaaaggta    4380
aatgtgcagt acattcgatg accaacgccg ttaccattcg agaagccgac gtagaagtag    4440
aggggaactc ccagctgcaa atatccttct caacagccct ggcaagcgcc gagtttcgcg    4500
tgcaagtgtg ctccacacaa gtacactgcg cagccgcatg ccaccctcca aaggaccaca    4560
tagtcaatta cccagcatca cacaccaccc ttggggtcca ggatatatcc acaacggcaa    4620
tgtcttgggt gcagaagatt acgggaggag taggattaat tgttgctgtt gctgccttaa    4680
tttttaattgt ggtgctatgc gtgtcgttta gcaggcacta aggatctaga tctgctgtgc    4740
cttctagttg ccagccatct gttgtttgcc cctccccgt gccttccttg accctggaag    4800
gtgccactcc cactgtcctt tcctaataaa atgaggaaat tgcatcgcat tgtctgagta    4860
ggtgtcattc tattctgggg ggtggggtgg ggcaggacag caaggggag gattgggaag    4920
acaatagcag gcatgctggg gatgcggtgg gctctatggg tacccaggtg ctgaagaatt    4980
gacccggttc ctcctgggcc agaaagaagc aggcacatcc ccttctctgt gacacaccct    5040
gtccacgccc ctggttctta gttccagccc cactcatagg acactcatag ctcaggaggg    5100
ctccgccttc aatcccaccc gctaaagtac ttggagcggt ctctccctcc ctcatcagcc    5160
caccaaacca aacctagcct ccaagagtgg gaagaaatta agcaagata ggctattaag    5220
tgcagaggga gagaaaatgc ctccaacatg tgaggaagta atgagagaaa tcatagaatt    5280
ttaaggccat gatttaaggc catcatggcc taagcttgaa aggagatagg atcaaagctt    5340
ggcgtaatca tggtcatagc tgtttcctgt gtgaaattgt tatccgctca caattccaca    5400
caacatacga gccggaagca taagtgtaa agcctgggt gcctaatgag tgagctaact    5460
cacattaatt gcgttgcgct cactgcccgc tttccagtcg ggaaacctgt cgtgccagct    5520
gcattaatga atcggccaac gcgcggggag aggcggtttg cgtattgggc gctcttccgc    5580
ttcctcgctc actgactcgc tgcgctcggt cgttcggctg cggcgagcgg tatcagctca    5640
ctcaaaggcg gtaatacggt tatccacaga atcaggggat aacgcaggaa agaacatgtg    5700
agcaaaaggc cagcaaaagg ccaggaaccg taaaaaggcc gcgttgctgg cgttttccca    5760
taggctccgc cccctgacg agcatcacaa aaatcgacgc tcaagtcaga ggtggcgaaa    5820
cccgacagga ctataaagat accaggcgtt tccccctgga agctccctcg tgcgctctcc    5880
tgttccgacc ctgccgctta ccggatacct gtccgccttt ctcccttcgg gaagcgtggc    5940
```

```
gctttctcat agctcacgct gtaggtatct cagttcggtg taggtcgttc gctccaagct    6000
gggctgtgtg cacgaacccc ccgttcagcc cgaccgctgc gccttatccg gtaactatcg    6060
tcttgagtcc aacccggtaa gacacgactt atcgccactg gcagcagcca ctggtaacag    6120
gattagcaga gcgaggtatg taggcggtgc tacagagttc ttgaagtggt ggcctaacta    6180
cggctacact agaagaacag tatttggtat ctgcgctctg ctgaagccag ttaccttcgg    6240
aaaaagagtt ggtagctctt gatccggcaa acaaaccacc gctggtagcg gtggtttttt    6300
tgtttgcaag cagcagatta cgcgcagaaa aaaggatct caagaagatc ctttgatctt    6360
ttctacgggg tctgacgctc agtggaacga aaactcacgt taagggattt tggtcatgag    6420
attatcaaaa aggatcttca cctagatcct tttaaattaa aatgaagttt taaatcaat     6480 ctaaagtata tatgagtaaa cttggtctga cagttaccaa tgcttaatca gtgaggcacc    6540
tatctcagcg atctgtctat ttcgttcatc catagttgcc tgactccccg tcgtgtagat    6600
aactacgata cgggagggct taccatctgg ccccagtgct gcaatgatac cgcgagaacc    6660
acgctcaccg gctccagatt tatcagcaat aaaccagcca gccggaaggg ccgagcgcag    6720
aagtggtcct gcaactttat ccgcctccat ccagtctatt aattgttgcc gggaagctag    6780
agtaagtagt tcgccagtta atagtttgcg caacgttgtt gccattgcta caggcatcgt    6840
ggtgtcacgc tcgtcgtttg gtatggcttc attcagctcc ggttcccaac gatcaaggcg    6900
agttacatga tcccccatgt tgtgcaaaaa agcggttagc tccttcggtc ctccgatcgt    6960
tgtcagaagt aagttggccg cagtgttatc actcatggtt atggcagcac tgcataattc    7020
tcttactgtc atgccatccg taagatgctt ttctgtgact ggtgagtact caaccaagtc    7080
attctgagaa tagtgtatgc ggcgaccgag ttgctcttgc ccggcgtcaa tacgggataa    7140
taccgcgcca catagcagaa ctttaaaagt gctcatcatt ggaaaacgtt cttcggggcg    7200
aaaactctca aggatcttac cgctgttgag atccagttcg atgtaaccca ctcgtgcacc    7260
caactgatct tcagcatctt ttactttcac cagcgtttct gggtgagcaa aaacaggaag    7320
gcaaaatgcc gcaaaaaagg aataagggc gacacggaaa tgttgaatac tcatactctt    7380
cctttttcaa tattattgaa gcatttatca gggttattgt ctcatgagcg gatacatatt    7440
tgaatgtatt tagaaaaata acaaataggg gttccgcgc acatttcccc gaaaagtgcc    7500
acctgacgtc taagaaacca ttattatcat gacattaacc tataaaaata ggcgtatcac    7560
gaggcccttt cgggtcgcgc gtttcggtga tgacggtgaa aacctctgac acatgcagct    7620
cccgttgacg gtcacagctt gtctgtaagc ggatgccggg agcagacaag cccgtcaggg    7680
cgcgtcagcg ggtgttggcg ggtgtcgggg ctggcttaac tatgcggcat cagagcagat    7740
tgtactgaga gtgcaccata aaattgtaaa cgttaatatt tgttaaaat tcgcgttaaa     7800 ttttgttaa atcagctcat tttttaacca ataggccgaa atcggcaaaa tcccttataa     7860
atcaaaagaa tagcccgaga tagggttgag tgttgttcca gtttggaaca agagtccact    7920
attaaagaac gtggactcca acgtcaaagg gcgaaaaacc gtctatcagg gcgatggccc    7980
actacgtgaa ccatcaccca aatcaagttt ttggggtcg aggtgccgta aagcactaaa     8040
tcggaaccct aaagggagcc ccgatttag agcttgacgg ggaaagccgg cgaacgtggc    8100
gagaaaggaa gggaagaaag cgaaaggagc gggcgctagg gcgctggcaa gtgtagcggt    8160
cacgctgcgc gtaaccacca cacccgccgc gcttaatgcg ccgctacagg gcgcgtacta    8220
tggttgcttt gacgtatgcg gtgtgaaata ccgcacagat gcgtaaggag aaaataccgc    8280
atcaggcgcc attcgccatt caggctgcgc aactgttggg aagggcgatc ggtgcgggcc    8340
```

-continued

```
tcttcgctat tacgccagct ggcgaaaggg ggatgtgctg caaggcgatt aagttgggta    8400
acgccagggt tttcccagtc acgacgttgt aaaacgacgg ccagtgaatt ccatggtctc    8460
aactttc                                                              8467
```

<210> SEQ ID NO 46
<211> LENGTH: 8452
<212> TYPE: DNA
<213> ORGANISM: Artificial Sequence
<220> FEATURE:
<223> OTHER INFORMATION: Synthetic polynucleotide

<400> SEQUENCE: 46

```
gaattcccat tgcatacgtt gtatccatat cataatatgt acatttatat tggctcatgt      60
ccaacattac cgccatgttg acattgatta ttgactagtt attaatagta atcaattacg     120
gggtcattag ttcatagccc atatatggag ttccgcgtta cataacttac ggtaaatggc     180
ccgcctggct gaccgcccaa cgacccccgc ccattgacgt caataatgac gtatgttccc     240
atagtaacgc caatagggac tttccattga cgtcaatggg tggagtattt acggtaaact     300
gcccacttgg cagtacatca agtgtatcat atgccaagta cgccccctat tgacgtcaat     360
gacggtaaat ggcccgcctg gcattatgcc cagtacatga ccttatggga ctttcctact     420
tggcagtaca tctacgtatt agtcatcgct attaccatgg tgatgcggtt ttggcagtac     480
atcaatgggc gtggatagcg gtttgactca cggggatttc caagtctcca ccccattgac     540
gtcaatggga gtttgttttg gcaccaaaat caacgggact ttccaaaatg tcgtaacaac     600
tccgccccat tgacgcaaat gggcggtagg cgtgtacggt gggaggtcta tataagcaga     660
gctcgtttag tgaaccgtca gatcgcctgg agacgccatc cacgctgttt tgacctccat     720
agaagacacc gggaccgatc cagcctccgt taacggtgga gggcagtgta gtctgagcag     780
tactcgttgc tgccgcgcgc gccaccagac ataatagctg acagactaac agactgttcc     840
tttccatggg tcttttctgc agtcaccgtc gtcgacacgt gtgatcagat atcgcggccg     900
ccaccatgga gttcatcccg acgcaaactt ctataacag aaggtaccaa ccccgaccct     960 gggcccacg ccctacaatt caagtaatta gacctagacc acgtccacag aggcaggctg    1020
ggcaactcgc ccagctgatc tccgcagtca acaaattgac catgcgcgcg gtacctcaac    1080
agaagcctcg cagaaatcgg aaaaacaaga agcaaaggca gaagaagcag gcgccgcaaa    1140
acgacccaaa gcaaaagaag caaccaccac aaaagaagcc ggctcaaaag aagaagaaac    1200
caggccgtag ggagagaatg tgcatgaaaa ttgaaaatga ttgcatcttc gaagtcaagc    1260
atgaaggcaa agtgatgggc tacgcatgcc tggtggggga taaagtaatg aaaccagcac    1320
atgtgaaggg aactatcgac aatgccgatc tggctaaact ggcctttaag cggtcgtcta    1380
aatacgatct tgaatgtgca cagataccgg tgcacatgaa gtctgatgcc tcgaagttta    1440
cccacgagaa acccgagggg tactataact ggcatcacgg agcagtgcag tattcaggag    1500
gccggttcac tatcccgacg ggtgcaggca agccgggaga cagcggcaga ccgatcttcg    1560
acaacaaagg acgggtggtg ccatcgtcc taggaggggc caacgaaggt gcccgcacgg    1620
ccctctccgt ggtgacgtgg aacaaagaca tcgtcacaaa aattacccct gagggagccg    1680
aagagtggag cctcgccctc ccggtcttgt gcctgttggc aaacactaca ttccctgct    1740 ctcagccgcc ttgcacaccc tgctgctacg aaaaggaacc ggaaagcacc ttgcgcatgc    1800
ttgaggacaa cgtgatgaga cccggatact accagcatac aaaaagcatcg ctgacttgct    1860
```

```
ctccccaccg ccaaagacgc agtactaagg acaattttaa tgtctataaa gccacaagac    1920
catatctagc tcattgtcct gactgcggag aagggcattc gtgccacagc cctatcgcat    1980
tggagcgcat cagaaatgaa gcaacggacg gaacgctgaa aatccaggtc tctttgcaga    2040
tcgggataaa gacagatgac agccacgatt ggaccaagct gcgctatatg gatagccata    2100
cgccagcgga cgcggagcga gccggattgc ttgtaaggac ttcagcaccg tgcacgatca    2160
ccgggaccat gggacacttt attctcgccc gatgcccgaa aggagagacg ctgacagtgg    2220
gatttacgga cagcagaaag atcagccaca catgcacaca cccgttccat catgaaccac    2280
ctgtgatagg tagggagagg ttccactctc gaccacaaca tggtaaagag ttaccttgca    2340
gcacgtacgt gcagagcacc gctgccactg ctgaggagat agaggtgcat atgcccccag    2400
atactcctga ccgcacgctg atgacgcagc agtctggcaa cgtgaagatc acagttaatg    2460
ggcagacggt gcggtacaag tgcaactgcg gtggctccgg aggcggcgcc atcagcctgc    2520
accccaaggc caagatcgag gaatctggat ccaacgaggg actgacaacc acagacaaag    2580
tgatcaataa ctgcaaaatt gatcagtgcc atgctgcagt cactaatcac aagaattggc    2640
aatacaactc ccctttagtc ccgcgcaacg ctgaactcgg ggaccgtaaa ggaaagatcc    2700
acatcccatt cccattggca aacgtgactt gcagagtgcc aaaagcaaga aaccctacag    2760
taacttacgg aaaaaaccaa gtcaccatgc tgctgtatcc tgaccatccg acactcttgt    2820
cttaccgtaa catgggacag gaaccaaatt accacgagga gtgggtgaca cacaagaagg    2880
aggttacctt gaccgtgcct actgagggtc tggaggtcac ttggggcaac aacgaaccat    2940
acaagtactg gccgcagatg tctacgaacg gtactgctca tggtcaccca catgagataa    3000
tcttgtacta ttatgagctg taccccacta tgactgtagt cattgtgtcg gtggcctcgt    3060
tcgtgcttct gtcgatggtg ggcacagcag tgggaatgtg tgtgtgcgca cggcgcagat    3120
gcattacacc atatgaatta acaccaggag ccactgttcc cttcctgctc agcctgctat    3180
gctgcgtcag aacgaccaag gcggccacat attacgaggc tgcggcatat ctatggaacg    3240
aacagcagcc cctgttctgg ttgcaggctc ttatcccgct ggccgccttg atcgtcctgt    3300
gcaactgtct gaaactcttg ccatgctgct gtaagaccct ggctttttta gccgtaatga    3360
gcatcggtgc ccacactgtg agcgcgtacg aacacgtaac agtgatcccg aacacggtgg    3420
gagtaccgta taagactctt gtcaacagac cgggttacag ccccatggtg ttggagatgg    3480
agctacaatc agtcaccttg gaaccaacac tgtcacttga ctacatcacg tgcgagtaca    3540
aaactgtcat cccctccccg tacgtgaagt gctgtggtac agcagagtgc aaggacaaga    3600
gcctaccaga ctacagctgc aaggtctttac ctggagtcta cccatttatg tggggcggcg    3660
cctactgctt ttgcgacgcc gaaaatacgc aattgagcga ggcacatgta gagaaatctg    3720
aatcttgcaa aacagagttt gcatcggcct acagagccca caccgcatcg gcgtcggcga    3780
agctccgcgt cctttaccaa ggaaacaaca ttaccgtagc tgcctacgct aacggtgacc    3840
atgccgtcac agtaaaggac gccaagtttg tcgtgggccc aatgtcctcc gcctggacac    3900
cttttgacaa caaatcgtg gtgtacaaag gcgacgtcta acatggac tacccacctt    3960 ttggcgcagg aagaccagga caatttggtg acattcaaag tcgtacaccg gaaagtaaag    4020
acgtttatgc caacactcag ttggtactac agaggccagc agcaggcacg gtacatgtac    4080
catactctca ggcaccatct ggcttcaagt attggctgaa ggaacgagga gcatcgctac    4140
agcacacgga accgttcggt tgccagattg cgacaaaccc ggtaagagct gtaaattgcg    4200
ctgtggggaa cataccaatt tccatcgaca taccggatgc ggccttttact agggttgtcg    4260
```

```
atgcaccctc tgtaacggac atgtcatgcg aagtaccagc ctgcactcac tcctccgact    4320
ttgggggcgt cgccatcatc aaatacacag ctagcaagaa aggtaaatgt gcagtacatt    4380
cgatgaccaa cgccgttacc attcgagaag ccgacgtaga agtagagggg aactcccagc    4440
tgcaaatatc cttctcaaca gccctggcaa gcgccgagtt tcgcgtgcaa gtgtgctcca    4500
cacaagtaca ctgcgcagcc gcatgccacc ctccaaagga ccacatagtc aattacccag    4560
catcacacac caccccttggg gtccaggata tatccacaac ggcaatgtct tgggtgcaga    4620
agattacggg aggagtagga ttaattgttg ctgttgctgc cttaattttta attgtggtgc    4680
tatgcgtgtc gtttagcagg cactaaggat ctagatctgc tgtgccttct agttgccagc    4740
catctgttgt ttgcccctcc cccgtgcctt ccttgaccct ggaaggtgcc actcccactg    4800
tcctttccta ataaaatgag gaaattgcat cgcattgtct gagtaggtgt cattctattc    4860
tggggggtgg ggtggggcag gacagcaagg gggaggattg ggaagacaat agcaggcatg    4920
ctggggatgc ggtgggctct atgggtaccc aggtgctgaa gaattgaccc ggttcctcct    4980
gggccagaaa gaagcaggca catccccttc tctgtgacac accctgtcca cgcccctggt    5040
tcttagttcc agccccactc ataggacact catagctcag gagggctccg ccttcaatcc    5100
cacccgctaa agtacttgga gcggtctctc cctccctcat cagcccacca aaccaaacct    5160
agcctccaag agtgggaaga aattaaagca agataggcta ttaagtgcag agggagagaa    5220
aatgcctcca acatgtgagg aagtaatgag agaaatcata gaattttaag gccatgattt    5280
aaggccatca tggcctaagc ttgaaaggag ataggatcaa agcttggcgt aatcatggtc    5340
atagctgttt cctgtgtgaa attgttatcc gctcacaatt ccacacaaca tacgagccgg    5400
aagcataaag tgtaaagcct ggggtgccta atgagtgagc taactcacat taattgcgtt    5460
gcgctcactg cccgctttcc agtcgggaaa cctgtcgtgc cagctgcatt aatgaatcgg    5520
ccaacgcgcg gggagaggcg gtttgcgtat gggcgctct tccgcttcct cgctcactga    5580
ctcgctgcgc tcggtcgttc ggctgcggcg agcggtatca gctcactcaa aggcggtaat    5640
acggttatcc acagaatcag gggataacgc aggaaagaac atgtgagcaa aaggccagca    5700
aaaggccagg aaccgtaaaa aggccgcgtt gctggcgttt ttccataggc tccgcccccc    5760
tgacgagcat cacaaaaatc gacgctcaag tcagaggtgg cgaaacccga caggactata    5820
aagataccag gcgtttcccc ctggaagctc cctcgtgcgc tctcctgttc cgaccctgcc    5880
gcttaccgga tacctgtccg cctttctccc ttcgggaagc gtggcgcttt ctcatagctc    5940
acgctgtagg tatctcagtt cggtgtaggt cgttcgctcc aagctgggct gtgtgcacga    6000
accccccgtt cagcccgacc gctgcgcctt atccggtaac tatcgtcttg agtccaaccc    6060
ggtaagacac gacttatcgc cactggcagc agccactggt aacaggatta gcagagcgag    6120
gtatgtaggc ggtgctacag agttcttgaa gtggtggcct aactacggct acactagaag    6180
aacagtattt ggtatctgcg ctctgctgaa gccagttacc ttcggaaaaa gagttggtag    6240
ctcttgatcc ggcaaacaaa ccaccgctgg tagcggtggt ttttttgttt gcaagcagca    6300
gattacgcgc agaaaaaaag gatctcaaga agatcctttg atcttttcta cggggtctga    6360
cgctcagtgg aacgaaaact cacgttaagg gattttggtc atgagattat caaaaaggat    6420
cttcacctag atccttttaa attaaaaatg aagttttaaa tcaatctaaa gtatatatga    6480
gtaaacttgg tctgacagtt accaatgctt aatcagtgag gcacctatct cagcgatctg    6540
tctatttcgt tcatccatag ttgcctgact ccccgtcgtg tagataacta cgatacggga    6600
```

```
gggcttacca tctggcccca gtgctgcaat gataccgcga gaaccacgct caccggctcc    6660
agatttatca gcaataaacc agccagccgg aagggccgag cgcagaagtg gtcctgcaac    6720
tttatccgcc tccatccagt ctattaattg ttgccgggaa gctagagtaa gtagttcgcc    6780
agttaatagt ttgcgcaacg ttgttgccat tgctacaggc atcgtggtgt cacgctcgtc    6840
gtttggtatg gcttcattca gctccggttc ccaacgatca aggcgagtta catgatcccc    6900
catgttgtgc aaaaaagcgg ttagctcctt cggtcctccg atcgttgtca gaagtaagtt    6960
ggccgcagtg ttatcactca tggttatggc agcactgcat aattctctta ctgtcatgcc    7020
atccgtaaga tgcttttctg tgactggtga gtactcaacc aagtcattct gagaatagtg    7080
tatgcggcga ccgagttgct cttgcccggc gtcaatacgg gataataccg cgccacatag    7140
cagaacttta aaagtgctca tcattggaaa acgttcttcg gggcgaaaac tctcaaggat    7200
cttaccgctg ttgagatcca gttcgatgta acccactcgt gcacccaact gatcttcagc    7260
atcttttact ttcaccagcg tttctgggtg agcaaaaaca ggaaggcaaa atgccgcaaa    7320
aaagggaata agggcgacac ggaaatgttg aatactcata ctcttccttt ttcaatatta    7380
ttgaagcatt tatcagggtt attgtctcat gagcggatac atatttgaat gtatttagaa    7440
aaataaacaa ataggggttc cgcgcacatt tccccgaaaa gtgccacctg acgtctaaga    7500
aaccattatt atcatgacat taacctataa aaataggcgt atcacgaggc cctttcgggt    7560
cgcgcgtttc ggtgatgacg gtgaaaacct ctgacacatg cagctcccgt tgacggtcac    7620
agcttgtctg taagcggatg ccgggagcag acaagcccgt cagggcgcgt cagcgggtgt    7680
tggcgggtgt cggggctggc ttaactatgc ggcatcagag cagattgtac tgagagtgca    7740
ccataaaatt gtaaacgtta atattttgtt aaaattcgcg ttaaattttt gttaaatcag    7800
ctcattttt aaccaatagg ccgaaatcgg caaaatccct tataaatcaa agaatagcc    7860
cgagataggg ttgagtgttg ttccagtttg gaacaagagt ccactattaa agaacgtgga    7920
ctccaacgtc aaagggcgaa aaaccgtcta tcagggcgat ggcccactac gtgaaccatc    7980
acccaaatca gtttttttgg ggtcgaggtg ccgtaaagca ctaaatcgga accctaaagg    8040
gagcccccga tttagagctt gacggggaaa gccggcgaac gtggcgagaa aggaagggaa    8100
gaaagcgaaa ggagcgggcg ctagggcgct ggcaagtgta gcggtcacgc tgcgcgtaac    8160
caccacaccc gccgcgctta atgcgccgct acagggcgcg tactatggtt gctttgacgt    8220
atgcggtgtg aaataccgca cagatgcgta aggagaaaat accgcatcag gcgccattcg    8280
ccattcaggc tgcgcaactg ttgggaaggg cgatcggtgc gggcctcttc gctattacgc    8340
cagctggcga aggggggatg tgctgcaagg cgattaagtt gggtaacgcc agggttttcc    8400
cagtcacgac gttgtaaaac gacggccagt gaattccatg gtctcaactt tc           8452
```

<210> SEQ ID NO 47
<211> LENGTH: 7290
<212> TYPE: DNA
<213> ORGANISM: Artificial Sequence
<220> FEATURE:
<223> OTHER INFORMATION: Synthetic polynucleotide

<400> SEQUENCE: 47

```
tcgcgcgttt cggtgatgac ggtgaaaacc tctgacacat gcagctcccg gagacggtca     60
cagcttgtct gtaagcggat gccgggagca gacaagcccg tcaggcgcgc tcagcgggtg    120
ttggcgggtg tcggggctgg cttaactatg cggcatcaga gcagattgta ctgagagtgc    180
accatatgcg gtgtgaaata ccgcacagat gcgtaaggag aaaataccgc atcaggcgcc    240
```

```
attcgccatt caggctgcgc aactgttggg aagggcgatc ggtgcgggcc tcttcgctat    300
tacgccagct ggcgaaaggg ggatgtgctg caaggcgatt aagttgggta acgccagggt    360
tttcccagtc acgacgttgt aaaacgacgg ccagtgaatt gacgcgtgtt ggcattgatt    420
attgactagt tattaatagt aatcaattac ggggtcatta gttcatagcc catatatgga    480
gttccgcgtt acataactta cggtaaatgg cccgcctggc tgaccgccca acgacccccg    540
cccattgacg tcaataatga cgtatgttcc catagtaacg ccaataggga ctttccattg    600
acgtcaatgg gtggagtatt tacggtaaac tgcccacttg gcagtacatc aagtgtatca    660
tatgccaagt acgcccccta ttgacgtcaa tgacggtaaa tggcccgcct ggcattatgc    720
ccagtacatg accttatggg actttcctac ttggcagtac atctacgtat tagtcatcgc    780
tattaccatg gtgatgcggt tttggcagta catcaatggg cgtggatagc ggtttgactc    840
acggggattt ccaagtctcc accccattga cgtcaatggg agtttgtttt ggcaccaaaa    900
tcaacgggac tttccaaaat gtcgtaacaa ctccgcccca ttgacgcaaa tgggcggtag    960
gcgtgtacgg tgggaggtct atataagcag agctcgttta gtgaaccgtc agataactgc   1020
aggtcgacga tatcgcggcc gccaccatgt cccgttcca gccaatgtat ccgatgcagc   1080
caatgcccta tcgcaacccg ttcgcggccc cgcgcaggcc ctggttcccc agaaccgacc   1140
cttttctggc gatgcaggtg caggaattaa cccgctcgat ggctaacctg acgttcaagc   1200
aacgccggga cgcgccacct gaggggccat ccgctaataa accgaagaag gaggcctcgc   1260
aaaaacagaa agggggaggc caagggaaga agaagaagaa ccaagggaag aagaaggcta   1320
agacagggcc gcctaatccg aaggcacaga atggaaacaa gaagaagacc aacaagaaac   1380
caggcaagag acagcgcatg gtcatgaaat tggaatctga caagacgttc ccaatcatgt   1440
tggaagggaa gataaacggc tacgcttgtg tggtcggagg gaagttattc aggccgatgc   1500
atgtggaagg caagatcgac aacgacgttc tggccgcgct taagacgaag aaagcatcca   1560
aatacgatct tgagtatgca gatgtgccac agaacatgcg ggccgataca ttcaaataca   1620
cccatgagaa accccaaggc tattacagct ggcatcatgg agcagtccaa tatgaaaatg   1680
ggcgtttcac ggtgccgaaa ggagttgggg ccaagggaga cagcggacga cccattctgg   1740
ataaccaggg acgggtggtc gctattgtgc tgggaggtgt gaatgaagga tctaggacag   1800 cccttttcagt cgtcatgtgg aacgagaagg gagttaccgt gaagtatact ccagagaact   1860
gcgagcaatg gtcactagtg accaccatgt gtctgctcgc caatgtgacg ttcccatgtg   1920
ctcaaccacc aatttgctac gacagaaaac cagcagagac tttggccatg ctcagcgtta   1980
acgttgacaa cccgggctac gatgagctgc tggaagcagc tgttaagtgc cccggaagga   2040 aaagagatc caccgaggag ctgtttaatg agtataagct aacgcgccct acatggcca   2100 gatgcatcag atgtgcagtt gggagctgcc atagtccaat agcaatcgag gcagtaaaga   2160
gcgacgggca cgacggttat gttagacttc agacttcctc gcagtatggc ctggattcct   2220
ccggcaactt aaagggcagg accatgcggt atgacatgca cgggaccatt aaagagatac   2280
cactacatca agtgtcactc tatacatctc gcccgtgtca cattgtggat gggcacggtt   2340
atttcctgct tgccaggtgc ccggcagggg actccatcac catggaattt aagaaagatt   2400
ccgtcagaca ctcctgctcg gtgccgtatg aagtgaaatt taatcctgta ggcagagaac   2460
tctatactca tccccagaa cacggagtag agcaagcgtg ccaagtctac gcacatgatg   2520
cacagaacag aggagcttat gtcgagatgc acctcccggg ctcagaagtg gacagcagtt   2580
```

```
tggtttcctt gagcggcagt tccggaggct gcatcatcag ctacggcgga gccgactact    2640
gcggcggatc ctcagtcacc gtgacacctc ctgatgggac tagcgccctg gtggaatgcg    2700
agtgtggcgg cacaaagatc tccgagacca tcaacaagac aaaacagttc agccagtgca    2760
caaagaagga gcagtgcaga gcatatcggc tgcagaacga taagtgggtg tataattctg    2820
acaaactgcc caaagcagcg ggagccacct aaaaggaaa actgcatgtc ccattcttgc     2880
tggcagacgg caaatgcacc gtgcctctag caccagaacc tatgataacc ttcggtttca    2940
gatcagtgtc actgaaactg caccctaaga atcccacata tctaatcacc cgccaacttg    3000
ctgatgagcc tcactacacg cacgagctca tatctgaacc agctgttagg aattttaccg    3060
tcaccgaaaa agggtgggag tttgtatggg gaaaccaccc gccgaaaagg ttttgggcac    3120
aggaaacagc acccggaaat ccacatgggc taccgcacga ggtgataact cattattacc    3180
acagataccc tatgtccacc atcctgggtt tgtcaatttg tgccgccatt gcaaccgttt    3240
ccgttgcagc gtctacctgg ctgttttgca gatcaagagt tgcgtgccta actccttacc    3300
ggctaacacc taacgctagg ataccatttt gtctggctgt gctttgctgc gcccgcactg    3360
cccgggccga gaccacctgg gagtccttgg atcacctatg gaacaataac caacagatgt    3420
tctggattca attgctgatc cctctggccg ccttgatcgt agtgactcgc tgctcaggt    3480 gcgtgtgctg tgtcgtgcct tttttagtca tggccggcgc cgcaggcgcc ggcgcctacg    3540
agcacgcgac cacgatgccg agccaagcgg gaatctcgta taacactata gtcaacagag    3600
caggctacgc accactccct atcagcataa caccaacaaa gatcaagctg atacctacag    3660
tgaacttgga gtacgtcacc tgccactaca aaacaggaat ggattcacca gccatcaaat    3720
gctgcggatc tcaggaatgc actccaactt acaggcctga tgaacagtgc aaagtcttca    3780
caggggttta cccgttcatg tggggtggtg catattgctt ttgcgacact gagaacaccc    3840
aagtcagcaa ggcctacgta atgaaatctg acgactgcct tgcggatcat gctgaagcat    3900
ataaagcgca cacagcctca gtgcaggcgt tcctcaacat cacagtggga gaacactcta    3960
ttgtgactac cgtgtatgtg aatggagaaa ctcctgtgaa tttcaatggg gtcaaaataa    4020
ctgcaggtcc gctttccaca gcttggacac ccttttgatcg caaaatcgtg cagtatgccg    4080
gggagatata taattatgat tttcctgagt atggggcagg acaaccagga gcatttggag    4140
atatacaatc cagaacagtc tcaagctctg atctgtatgc caataccaac ctagtgctgc    4200
agagacccaa agcaggagcg atccacgtgc catacactca ggcaccttcg ggttttgagc    4260
aatggaagaa agataaagct ccatcattga aatttaccgc ccctttcgga tgcgaaatat    4320
atacaaaccc cattcgcgcc gaaaactgtg ctgtagggtc aattccatta gcctttgaca    4380
ttcccgacgc cttgttcacc agggtgtcag aaacaccgac actttcagcg gccgaatgca    4440
ctcttaacga gtgcgtgtat tcttccgact ttggtgggat cgccacggtc aagtactcgg    4500
ccagcaagtc aggcaagtgc gcagtccatg tgccatcagg gactgctacc ctaaaagaag    4560
cagcagtcga gctaaccgag caagggtcgg cgactatcca tttctcgacc gcaaatatcc    4620
acccggagtt caggctccaa atatgcacat catatgttac gtgcaaaggt gattgtcacc    4680
ccccgaaaga ccatattgtg acacaccctc agtatacgc ccaaacattt acagccgcgg     4740
tgtcaaaaac cgcgtggacg tggttaacat ccctgctggg aggatcagcc gtaattatta    4800
taattggctt ggtgctggct actattgtgg ccatgtacgt gctgaccaac cagaaacata    4860
attaaggatc tagatctgct gtgccttcta gttgccagcc atctgttgtt tgcccctccc    4920
ccgtgccttc cttgaccctg gaaggtgcca ctcccactgt cctttcctaa taaaatgagg    4980
```

```
aaattgcatc gcattgtctg agtaggtgtc attctattct gggggggtggg gtggggcagg    5040 acagcaaggg ggaggattgg gaagacaata gcaggcatgc tggggatgcg gtgggctcta    5100
tggctcgagc atggtcatag ctgtttcctg tgtgaaattg ttatccgctc acaattccac    5160
acaacatacg agccggaagc ataaagtgta agcctgggg tgcctaatga gtgagctaac     5220
tcacattaat tgcgttgcgc tcactgcccg ctttccagtc gggaaacctg tcgtgccagc    5280
tgcattaatg aatcggccaa cgcgcgggga gaggcggttt gcgtattggg cgctcttccg    5340
cttcctcgct cactgactcg ctgcgctcgg tcgttcggct gcggcgagcg gtatcagctc    5400
actcaaaggc ggtaatacgg ttatccacag aatcaggga taacgcagga aagaacatgt     5460
gagcaaaagg ccagcaaaag gccaggaacc gtaaaaaggc cgcgttgctg gcgttttttcc    5520 ataggctccg ccccctgac gagcatcaca aaaatcgacg ctcaagtcag aggtggcgaa     5580
acccgacagg actataaaga taccaggcgt ttccccctgg aagctccctc gtgcgctctc    5640
ctgttccgac cctgccgctt accggatacc tgtccgcctt tctcccttcg ggaagcgtgg    5700
cgctttctca tagctcacgc tgtaggtatc tcagttcggt gtaggtcgtt cgctccaagc    5760
tgggctgtgt gcacgaaccc cccgttcagc ccgaccgctg cgccttatcc ggtaactatc    5820
gtcttgagtc caacccggta agacacgact tatcgccact ggcagcagcc actggtaaca    5880
ggattagcag agcgaggtat gtaggcggtg ctacagagtt cttgaagtgg tggcctaact    5940
acggctacac tagaagaaca gtatttggta tctgcgctct gctgaagcca gttaccttcg    6000
gaaaaagagt tggtagctct tgatccggca aacaaaccac cgctggtagc ggtggttttt    6060
ttgtttgcaa gcagcagatt acgcgcagaa aaaaaggatc tcaagaagat cctttgatct    6120
tttctacggg gtctgacgct cagtggaacg aaaaactcacg ttaagggatt ttggtcatga   6180
gattatcaaa aaggatcttc acctagatcc ttttaaatta aaaatgaagt tttaaatcaa    6240
tctaaagtat atatgagtaa acttggtctg acagttagaa aaactcatcg agcatcaaat    6300
gaaactgcaa tttattcata tcaggattat caataccata ttttgaaaa agccgtttct     6360 gtaatgaagg agaaaactca ccgaggcagt tccataggat ggcaagatcc tggtatcggt    6420
ctgcgattcc gactcgtcca acatcaatac aacctattaa tttcccctcg tcaaaaataa    6480
ggttatcaag tgagaaatca ccatgagtga cgactgaatc cggtgagaat ggcaaaagtt    6540
tatgcatttc tttccagact tgttcaacag gccagccatt acgctcgtca tcaaaatcac    6600
tcgcatcaac caaaccgtta ttcattcgtg attgcgcctg agcgagacga atacgcgat    6660 cgctgttaaa aggacaatta caaacaggaa tcgaatgcaa ccggcgcagg aacactgcca    6720
gcgcatcaac aatatttca cctgaatcag gatattcttc taatacctgg aatgctgttt    6780
tcccagggat cgcagtggtg agtaaccatg catcatcagg agtacggata aaatgcttga    6840
tggtcggaag aggcataaat tccgtcagcc agtttagtct gaccatctca tctgtaacat    6900
cattggcaac gctaccttg ccatgtttca gaaacaactc tggcgcatcg gcttcccat     6960 acaatcgata gattgtcgca cctgattgcc cgacattatc gcgagcccat ttataccat     7020 ataaatcagc atccatgttg gaatttaatc gcggcctaga gcaagacgtt tcccgttgaa    7080
tatggctcat actcttcctt tttcaatatt attgaagcat ttatcagggt tattgtctca    7140
tgagcggata catatttgaa tgtatttaga aaataaaca aatagggggtt ccgcgcacat    7200 ttccccgaaa agtgccacct gacgtctaag aaaccattat tatcatgaca ttaacctata   7260
aaaataggcg tatcacgagg ccctttcgtc                                     7290
```

<210> SEQ ID NO 48
<211> LENGTH: 8491
<212> TYPE: DNA
<213> ORGANISM: Artificial Sequence
<220> FEATURE:
<223> OTHER INFORMATION: Synthetic polynucleotide

<400> SEQUENCE: 48

```
gaattcccat tgcatacgtt gtatccatat cataatatgt acatttatat tggctcatgt      60
ccaacattac cgccatgttg acattgatta ttgactagtt attaatagta atcaattacg     120
gggtcattag ttcatagccc atatatggag ttccgcgtta cataacttac ggtaaatggc     180
ccgcctggct gaccgcccaa cgacccccgc ccattgacgt caataatgac gtatgttccc     240
atagtaacgc caatagggac tttccattga cgtcaatggg tggagtattt acggtaaact     300
gcccacttgg cagtacatca agtgtatcat atgccaagta cgccccctat tgacgtcaat     360
gacggtaaat ggcccgcctg gcattatgcc cagtacatga ccttatggga ctttcctact     420
tggcagtaca tctacgtatt agtcatcgct attaccatgg tgatgcggtt ttggcagtac     480
atcaatgggc gtggatagcg gtttgactca cggggatttc caagtctcca ccccattgac     540
gtcaatggga gtttgttttg gcaccaaaat caacgggact ttccaaaatg tcgtaacaac     600
tccgccccat tgacgcaaat gggcggtagg cgtgtacggt gggaggtcta tataagcaga     660
gctcgtttag tgaaccgtca gatcgcctgg agacgccatc cacgctgttt tgacctccat     720
agaagacacc gggaccgatc cagcctccgt taacgtggga gggcagtgta gtctgagcag     780
tactcgttgc tgccgcgcgc gccaccagac ataatagctg acagactaac agactgttcc     840
tttccatggg tcttttctgc agtcaccgtc gtcgacacgt gtgatcagat atcgcggccg     900
ccaccatgtt cccgttccag ccaatgtatc cgatgcagcc aatgcctat cgcaacccgt     960
cgcggccccg cgcaggccc tggttcccca gaaccgaccc ttttctggcg atgcaggtgc    1020
aggaattaac ccgctcgatg gctaacctga cgttcaagca acgccgggac gcgccacctg    1080
aggggccatc cgctaataaa ccgaagaagg aggcctcgca aaaacagaaa gggggaggcc    1140
aagggaagaa gaagaagaac caagggaaga agaaggctaa gacagggccg cctaatccga    1200
aggcacagaa tggaaacaag aagaagacca caagaaacc aggcaagaga cagcgcatgg    1260
tcatgaaatt ggaatctgac aagacgttcc caatcatgtt ggaagggaag ataaacggct    1320
acgcttgtgt ggtcggaggg aagttattca ggccgatgca tgtggaaggc aagatcgaca    1380
acgacgttct ggccgcgctt aagacgaaga aagcatccaa atacgatctt gagtatgcag    1440
atgtgccaca gaacatgcgg gccgatacat tcaaatacac ccatgagaaa ccccaaggct    1500
attacagctg gcatcatgga gcagtccaat atgaaaatgg cgtttcacg gtgccgaaag    1560
gagttggggc caagggagac agcggacgac ccattctgga taaccaggga cgggtggtcg    1620
ctattgtgct gggaggtgtg aatgaaggat ctaggacagc cctttcagtc gtcatgtgga    1680
acgagaaggg agttaccgtg aagtatactc agagaactg cgagcaatgg tcactagtga    1740
ccaccatgtg tctgctcgcc aatgtgacgt tcccatgtgc tcaaccacca atttgctacg    1800
acagaaaacc agcagagact ttggccatgc tcagcgttaa cgttgacaac ccgggctacg    1860
atgagctgct ggaagcagct gttaagtgcc ccggaaggaa aaggagatcc accgaggagc    1920
tgtttaatga gtataagcta acgcgcccctt acatggccag atgcatcaga gtgtgcagttg    1980
ggagctgcca tagtccaata gcaatcgagg cagtaaagag cgacgggcac gacgttatg    2040
ttagacttca gacttcctcg cagtatggcc tggattcctc cggcaactta aagggcagga    2100
```

```
ccatgcggta tgacatgcac gggaccatta aagagatacc actacatcaa gtgtcactct  2160
atacatctcg cccgtgtcac attgtggatg ggcacggtta tttcctgctt gccaggtgcc  2220
cggcagggga ctccatcacc atggaattta agaaagattc cgtcagacac tcctgctcgg  2280
tgccgtatga agtgaaattt aatcctgtag gcagagaact ctatactcat cccccagaac  2340
acggagtaga gcaagcgtgc caagtctacg cacatgatgc acagaacaga ggagcttatg  2400
tcgagatgca cctcccgggc tcagaagtgg acagcagttt ggtttccttg agcggcagtt  2460
ccggaggact aaactggtac cgcatgagcc ccagcaacca gacggacaag ctggccgcct  2520
tcggaggatc ctcagtcacc gtgacacctc ctgatgggac tagcgccctg gtggaatgcg  2580
agtgtggcgg cacaaagatc tccgagacca tcaacaagac aaaacagttc agccagtgca  2640
caaagaagga gcagtgcaga gcatatcggc tgcagaacga taagtgggtg tataattctg  2700
acaaactgcc caaagcagcg ggagccacct aaaaggaaa actgcatgtc ccattcttgc  2760
tggcagacgg caaatgcacc gtgcctctag caccagaacc tatgataacc ttcggtttca  2820
gatcagtgtc actgaaactg caccctaaga atcccacata tctaatcacc cgccaacttg  2880
ctgatgagcc tcactacacg cacgagctca tatctgaacc agctgttagg aattttaccg  2940
tcaccgaaaa agggtgggag tttgtatggg gaaaccaccc gccgaaaagg ttttgggcac  3000
aggaaacagc acccggaaat ccacatgggc taccgcacga ggtgataact cattattacc  3060
acagataccc tatgtccacc atcctgggtt tgtcaatttg tgccgccatt gcaaccgttt  3120
ccgttgcagc gtctacctgg ctgttttgca gatcaagagt tgcgtgccta actccttacc  3180
ggctaacacc taacgctagg ataccatttt gtctggctgt gctttgctgc gcccgcactg  3240
cccgggccga gaccacctgg gagtccttgg atcacctatg gaacaataac caacagatgt  3300
tctggattca attgctgatc cctctggccg ccttgatcgt agtgactcgc ctgctcaggt  3360
gcgtgtgctg tgtcgtgcct ttttagtca tggccggcgc cgcaggcgcc ggcgcctacg  3420
agcacgcgac cacgatgccg agccaagcgg gaatctcgta taacactata gtcaacagag  3480
caggctacgc accactccct atcagcataa caccaacaaa gatcaagctg atacctacag  3540
tgaacttgga gtacgtcacc tgccactaca aaacaggaat ggattcacca gccatcaaat  3600
gctgcggatc tcaggaatgc actccaactt acaggcctga tgaacagtgc aaagtcttca  3660
caggggttta cccgttcatg tggggtggtg catattgctt ttgcgacact gagaacaccc  3720
aagtcagcaa ggcctacgta atgaaatctg acgactgcct tgcggatcat gctgaagcat  3780
ataaagcgca cacagcctca gtgcaggcgt tcctcaacat cacagtggga gaacactcta  3840
ttgtgactac cgtgtatgtg aatggagaaa ctcctgtgaa tttcaatggg gtcaaaataa  3900
ctgcaggtcc gctttccaca gcttggacac cctttgatcg caaaatcgtg cagtatgccg  3960
gggagatcta taattatgat tttcctgagt atggggcagg acaaccagga gcatttggag  4020
atatacaatc cagaacagtc tcaagctctg atctgtatgc caataccaac ctagtgctgc  4080
agagacccaa agcaggagcg atccacgtgc catacactca ggcaccttcg ggttttgagc  4140
aatggaagaa agataaagct ccatcattga aatttaccgc ccctttcgga tgcgaaatat  4200
atacaaaccc cattcgcgcc gaaaactgtg ctgtagggtc aattccatta gcctttgaca  4260
ttccccgacgc cttgttcacc agggtgtcag aaacaccgac actttcagcg ccgaatgca  4320
ctcttaacga gtgcgtgtat tcttccgact ttggtgggat cgccacggtc aagtactcgg  4380
ccagcaagtc aggcaagtgc gcagtccatg tgccatcagg gactgctacc ctaaaagaag  4440
```

```
cagcagtcga gctaaccgag caagggtcgg cgactatcca tttctcgacc gcaaatatcc    4500
acccggagtt caggctccaa atatgcacat catatgttac gtgcaaaggt gattgtcacc    4560
ccccgaaaga ccatattgtg acacaccctc agtatcacgc ccaaacattt acagccgcgg    4620
tgtcaaaaac cgcgtggacg tggttaacat ccctgctggg aggatcagcc gtaattatta    4680
taattggctt ggtgctggct actattgtgg ccatgtacgt gctgaccaac cagaaacata    4740
attaaggatc tagatctgct gtgccttcta gttgccagcc atctgttgtt tgcccctccc    4800
ccgtgccttc cttgaccctg gaaggtgcca ctcccactgt cctttcctaa taaaatgagg    4860
aaattgcatc gcattgtctg agtaggtgtc attctattct ggggggtggg gtggggcagg    4920
acagcaaggg ggaggattgg gaagacaata gcaggcatgc tggggatgcg gtgggctcta    4980
tgggtaccca ggtgctgaag aattgacccg gttcctcctg ggccagaaag aagcaggcac    5040
atccccttct ctgtgacaca ccctgtccac gcccctggtt cttagttcca gccccactca    5100
taggacactc atagctcagg agggctccgc cttcaatccc acccgctaaa gtacttggag    5160
cggtctctcc ctccctcatc agcccaccaa accaaaccta gcctcaagagtgggaagaa      5220
attaaagcaa gataggctat taagtgcaga gggagagaaa atgcctccaa catgtgagga    5280
agtaatgaga gaaatcatag aattttaagg ccatgattta aggccatcat ggcctaagct    5340
tgaaaggaga taggatcaaa gcttggcgta atcatggtca tagctgtttc ctgtgtgaaa    5400
ttgttatccg ctcacaattc cacacaacat acgagccgga agcataaagt gtaaagcctg    5460
gggtgcctaa tgagtgagct aactcacatt aattgcgttg cgctcactgc ccgctttcca    5520
gtcgggaaac ctgtcgtgcc agctgcatta atgaatcggc caacgcgcgg ggagaggcgg    5580
tttgcgtatt gggcgctctt ccgcttcctc gctcactgac tcgctgcgct cggtcgttcg    5640
gctgcggcga gcggtatcag ctcactcaaa ggcggtaata cggttatcca cagaatcagg    5700
ggataacgca ggaaagaaca tgtgagcaaa aggccagcaa aaggccagga accgtaaaaa    5760
ggccgcgttg ctggcgtttt tccataggct ccgcccccct gacgagcatc acaaaaatcg    5820
acgctcaagt cagaggtggc gaaacccgac aggactataa agataccagg cgtttccccc    5880
tggaagctcc ctcgtgcgct ctcctgttcc gaccctgccg cttaccggat acctgtccgc    5940
ctttctccct tcgggaagcg tggcgctttc tcatagctca cgctgtaggt atctcagttc    6000
ggtgtaggtc gttcgctcca agctgggctg tgtgcacgaa ccccccgttc agcccgaccg    6060
ctgcgcctta tccggtaact atcgtcttga gtccaacccg gtaagacacg acttatcgcc    6120
actggcagca gccactggta acaggattag cagagcgagg tatgtaggcg gtgctacaga    6180
gttcttgaag tggtggccta actacggcta cactagaaga acagtatttg gtatctgcgc    6240
tctgctgaag ccagttacct tcggaaaaag agttggtagc tcttgatccg gcaaacaaac    6300
caccgctggt agcggtggtt tttttgtttg caagcagcag attacgcgca gaaaaaaagg    6360
atctcaagaa gatcctttga tcttttctac ggggtctgac gctcagtgga acgaaaactc    6420
acgttaaggg attttggtca tgagattatc aaaaaggatc ttcacctaga tccttttaaa    6480
ttaaaaatga agttttaaat caatctaaag tatatatgag taaacttggt ctgacagtta    6540
ccaatgctta atcagtgagg cacctatctc agcgatctgt ctatttcgtt catccatagt    6600
tgcctgactc ccgtcgtgt agataactac gatacgggag ggcttaccat ctggccccag    6660
tgctgcaatg ataccgcgag aaccacgctc accggctcca gatttatcag caataaacca    6720
gccagccgga agggccgagc gcagaagtgg tcctgcaact ttatccgcct ccatccagtc    6780
tattaattgt tgccgggaag ctagagtaag tagttcgcca gttaatagtt tgcgcaacgt    6840
```

| | |
|---|---|
| tgttgccatt gctacaggca tcgtggtgtc acgctcgtcg tttggtatgg cttcattcag | 6900 |
| ctccggttcc caacgatcaa ggcgagttac atgatccccc atgttgtgca aaaaagcggt | 6960 |
| tagctccttc ggtcctccga tcgttgtcag aagtaagttg gccgcagtgt tatcactcat | 7020 |
| ggttatggca gcactgcata attctcttac tgtcatgcca tccgtaagat gcttttctgt | 7080 |
| gactggtgag tactcaacca agtcattctg agaatagtgt atgcggcgac cgagttgctc | 7140 |
| ttgcccggcg tcaatacggg ataataccgc gccacatagc agaactttaa aagtgctcat | 7200 |
| cattggaaaa cgttcttcgg ggcgaaaact ctcaaggatc ttaccgctgt tgagatccag | 7260 |
| ttcgatgtaa cccactcgtg cacccaactg atcttcagca tcttttactt tcaccagcgt | 7320 |
| ttctgggtga gcaaaaacag gaaggcaaaa tgccgcaaaa aagggaataa gggcgacacg | 7380 |
| gaaatgttga atactcatac tcttcctttt tcaatattat tgaagcattt atcagggtta | 7440 |
| ttgtctcatg agcggataca tatttgaatg tatttagaaa aataaacaaa tagggggttcc | 7500 |
| gcgcacattt ccccgaaaag tgccacctga cgtctaagaa accattatta tcatgacatt | 7560 |
| aacctataaa aataggcgta tcacgaggcc ctttcgggtc gcgcgtttcg gtgatgacgg | 7620 |
| tgaaaacctc tgacacatgc agctcccgtt gacggtcaca gcttgtctgt aagcggatgc | 7680 |
| cgggagcaga caagcccgtc agggcgcgtc agcgggtgtt ggcgggtgtc ggggctggct | 7740 |
| taactatgcg gcatcagagc agattgtact gagagtgcac cataaaattg taaacgttaa | 7800 |
| tattttgtta aaattcgcgt taaattttg ttaaatcagc tcattttta accaataggc | 7860 |
| cgaaatcggc aaaatccctt ataaatcaaa agaatagccc gagataggt tgagtgttgt | 7920 |
| tccagtttgg aacaagagtc cactattaaa gaacgtggac tccaacgtca agggcgaaa | 7980 |
| aaccgtctat cagggcgatg gcccactacg tgaaccatca cccaaatcaa gttttttggg | 8040 |
| gtcgaggtgc cgtaaagcac taaatcggaa ccctaaaggg agcccccgat ttagagcttg | 8100 |
| acggggaaag ccggcgaacg tggcgagaaa ggaagggaag aaagcgaaag gagcgggcgc | 8160 |
| tagggcgctg gcaagtgtag cggtcacgct gcgcgtaacc accacacccg ccgcgcttaa | 8220 |
| tgcgccgcta cagggcgcgt actatggttg ctttgacgta tgcggtgtga aataccgcac | 8280 |
| agatgcgtaa ggagaaaata ccgcatcagg cgccattcgc cattcaggct gcgcaactgt | 8340 |
| tgggaagggc gatcggtgcg ggcctcttcg ctattacgcc agctggcgaa aggggggatgt | 8400 |
| gctgcaaggc gattaagttg ggtaacgcca gggttttccc agtcacgacg ttgtaaaacg | 8460 |
| acggccagtg aattccatgg tctcaacttt c | 8491 |

<210> SEQ ID NO 49
<211> LENGTH: 8476
<212> TYPE: DNA
<213> ORGANISM: Artificial Sequence
<220> FEATURE:
<223> OTHER INFORMATION: Synthetic polynucleotide

<400> SEQUENCE: 49

| | |
|---|---|
| gaattcccat tgcatacgtt gtatccatat cataatatgt acatttatat tggctcatgt | 60 |
| ccaacattac cgccatgttg acattgatta ttgactagtt attaatagta atcaattacg | 120 |
| gggtcattag ttcatagccc atatatggag ttccgcgtta cataacttac ggtaaatggc | 180 |
| ccgcctggct gaccgcccaa cgaccccgc ccattgacgt caataatgac gtatgttccc | 240 |
| atagtaacgc caatagggac tttccattga cgtcaatggg tggagtattt acggtaaact | 300 |
| gcccacttgg cagtacatca agtgtatcat atgccaagta cgccccctat tgacgtcaat | 360 |

-continued

```
gacggtaaat ggcccgcctg gcattatgcc cagtacatga ccttatggga ctttcctact      420
tggcagtaca tctacgtatt agtcatcgct attaccatgg tgatgcggtt ttggcagtac      480
atcaatgggc gtggatagcg gtttgactca cggggatttc caagtctcca ccccattgac      540
gtcaatggga gtttgttttg gcaccaaaat caacgggact ttccaaaatg tcgtaacaac      600
tccgccccat tgacgcaaat gggcggtagg cgtgtacggt gggaggtcta tataagcaga      660
gctcgtttag tgaaccgtca gatcgcctgg agacgccatc cacgctgttt tgacctccat      720
agaagacacc gggaccgatc cagcctccgt taacggtgga gggcagtgta gtctgagcag      780
tactcgttgc tgccgcgcgc gccaccagac ataatagctg acagactaac agactgttcc      840
tttccatggg tcttttctgc agtcaccgtc gtcgacacgt gtgatcagat atcgcggccg      900
ccaccatgtt cccgttccag ccaatgtatc cgatgcagcc aatgccctat cgcaacccgt      960
tcgcggcccc gcgcaggccc tggttcccca gaaccgaccc ttttctggcg atgcaggtgc     1020
aggaattaac ccgctcgatg gctaacctga cgttcaagca acgccgggac gcgccacctg     1080
aggggccatc cgctaataaa ccgaagaagg aggcctcgca aaaacagaaa gggggaggcc     1140
aagggaagaa gaagaagaac caagggaaga agaaggctaa gacagggccg cctaatccga     1200
aggcacagaa tggaaacaag aagaagacca acaagaaacc aggcaagaga cagcgcatgg     1260
tcatgaaatt ggaatctgac aagacgttcc caatcatgtt ggaagggaag ataaacggct     1320
acgcttgtgt ggtcgagggg aagttattca ggccgatgca tgtggaaggc aagatcgaca     1380
acgacgttct ggccgcgctt aagacgaaga aagcatccaa atacgatctt gagtatgcag     1440
atgtgccaca gaacatgcgg gccgatacat tcaaatacac ccatgagaaa ccccaaggct     1500
attacagctg gcatcatgga gcagtccaat atgaaaatgg gcgtttcacg gtgccgaaag     1560
gagttggggc caagggagac agcggacgac ccattctgga taaccaggga cgggtggtcg     1620
ctattgtgct gggaggtgtg aatgaaggat ctaggacagc cctttcagtc gtcatgtgga     1680
acgagaaggg agttaccgtg aagtatactc cagagaactg cgagcaatgg tcactagtga     1740
ccaccatgtg tctgctcgcc aatgtgacgt tcccatgtgc tcaaccacca atttgctacg     1800
acagaaaacc agcagagact ttggccatgc tcagcgttaa cgttgacaac ccgggctacg     1860
atgagctgct ggaagcagct gttaagtgcc ccggaaggaa aaggagatcc accgaggagc     1920
tgtttaatga gtataagcta acgcgcccctt acatggccag atgcatcaga gtgcagttg      1980 ggagctgcca tagtccaata gcaatcgagg cagtaaagag cgacgggcac gacggttatg     2040
ttagacttca gacttcctcg cagtatgcc tggattcctc cggcaactta aagggcagga     2100
ccatgcggta tgacatgcac gggaccatta agagatacc actacatcaa gtgtcactct     2160
atacatctcg cccgtgtcac attgtggatg ggcacggtta tttcctgctt gccaggtgcc     2220
cggcagggga ctccatcacc atggaattta agaaagattc cgtcagacac tcctgctcgg     2280
tgccgtatga agtgaaattt aatcctgtag gcagagaact ctatactcat cccccagaac     2340
acggagtaga gcaagcgtgc caagtctacg cacatgatga acagaacaga ggagcttatg     2400
tcgagatgca cctcccgggc tcagaagtgg acagcagttt ggtttccttg agcggcagtt     2460
ccggaggcgg cgccatcagc ctgcacccca aggccaagat cgaggaatct ggatcctcag     2520
tcaccgtgac acctcctgat gggactagcg ccctggtgga atgcgagtgt ggcggcacaa     2580
agatctccga gaccatcaac aagacaaaac agttcagcca gtgcacaaag aaggagcagt     2640
gcagagcata tcggctgcag aacgataagt gggtgtataa ttctgacaaa ctgcccaaag     2700
cagcgggagc caccttaaaa ggaaaactgc atgtcccatt cttgctggca gacggcaaat     2760
```

```
gcaccgtgcc tctagcacca gaacctatga taaccttcgg tttcagatca gtgtcactga   2820
aactgcaccc taagaatccc acatatctaa tcacccgcca acttgctgat gagcctcact   2880
acacgcacga gctcatatct gaaccagctg ttaggaattt taccgtcacc gaaaaagggt   2940
gggagtttgt atgggaaac  cacccgccga aaaggttttg gcacaggaa  acagcacccg   3000 gaaatccaca tgggctaccg cacgaggtga taactcatta ttaccacaga taccctatgt   3060
ccaccatcct gggtttgtca atttgtgccg ccattgcaac cgtttccgtt gcagcgtcta   3120
cctggctgtt ttgcagatca agagttgcgt gcctaactcc ttaccggcta cacctaacg    3180 ctaggatacc attttgtctg gctgtgcttt gctgcgcccg cactgcccgg gccgagacca   3240
cctgggagtc cttggatcac ctatggaaca ataaccaaca gatgttctgg attcaattgc   3300
tgatccctct ggccgccttg atcgtagtga ctcgcctgct caggtgcgtg tgctgtgtcg   3360
tgcctttttt agtcatggcc ggcgccgcag gcgccggcgc ctacgagcac gcgaccacga   3420
tgccgagcca agcgggaatc tcgtataaca ctatagtcaa cagagcaggc tacgcaccac   3480
tccctatcag cataacacca acaaagatca agctgatacc tacagtgaac ttggagtacg   3540
tcacctgcca ctacaaaaca ggaatggatt caccagccat caaatgctgc ggatctcagg   3600
aatgcactcc aacttacagg cctgatgaac agtgcaaagt cttcacaggg gtttacccgt   3660
tcatgtgggg tggtgcatat tgcttttgcg cactgagaa  cacccaagtc agcaaggcct   3720
acgtaatgaa atctgacgac tgccttgcgg atcatgctga agcatataaa gcgcacacag   3780
cctcagtgca ggcgttcctc aacatcacag tgggagaaca ctctattgtg actaccgtgt   3840
atgtgaatgg agaaactcct gtgaatttca atggggtcaa ataactgca  ggtccgcttt   3900 ccacagcttg dacacccttt gatcgcaaaa tcgtgcagta tgccggggag atctataatt   3960
atgattttcc tgagtatggg gcaggacaac caggagcatt tggagatata caatccagaa   4020
cagtctcaag ctctgatctg tatgccaata ccaacctagt gctgcagaga cccaaagcag   4080
gagcgatcca cgtgccatac actcaggcac cttcgggttt tgagcaatgg aagaaagata   4140
aagctccatc attgaaattt accgcccctt tcggatgcga aatatataca aaccccattc   4200
gcgccgaaaa ctgtgctgta gggtcaattc cattagcctt tgacattccc gacgccttgt   4260
tcaccagggt gtcagaaaca ccgacacttt cagcggccga atgcactctt aacgagtgcg   4320
tgtattcttc cgactttggt gggatcgcca cggtcaagta ctcggccagc aagtcaggca   4380
agtgcgcagt ccatgtgcca tcagggactg ctaccctaaa agaagcagca gtcgagctaa   4440
ccgagcaagg gtcggcgact atccatttct cgaccgcaaa tatccacccg gagttcaggc   4500
tccaaatatg cacatcatat gttacgtgca aggtgattg  tcacccccg  aaagaccata   4560 ttgtgacaca ccctcagtat cacgcccaaa catttacagc cgcggtgtca aaaaccgcgt   4620
ggacgtggtt aacatccctg ctgggaggat cagccgtaat tattataatt ggcttggtgc   4680
tggctactat tgtggccatg tacgtgctga ccaaccagaa acataattaa ggatctagat   4740
ctgctgtgcc ttctagttgc cagccatctg ttgtttgccc ctcccccgtg ccttccttga   4800
ccctggaagg tgccactccc actgtccttt cctaataaaa tgaggaaatt gcatcgcatt   4860
gtctgagtag gtgtcattct attctggggg gtggggtggg gcaggacagc aagggggagg   4920
attgggaaga caatagcagg catgctgggg atgcggtggg ctctatgggt acccaggtgc   4980
tgaagaattg acccggttcc tcctgggcca gaaagaagca ggcacatccc cttctctgtg   5040
acacaccctg tccacgcccc tggttcttag ttccagcccc actcatagga cactcatagc   5100
```

```
tcaggagggc tccgccttca atcccacccg ctaaagtact tggagcggtc tctccctccc    5160
tcatcagccc accaaaccaa acctagcctc caagagtggg aagaaattaa agcaagatag    5220
gctattaagt gcagagggag agaaaatgcc tccaacatgt gaggaagtaa tgagagaaat    5280
catagaattt taaggccatg atttaaggcc atcatggcct aagcttgaaa ggagatagga    5340
tcaaagcttg gcgtaatcat ggtcatagct gtttcctgtg tgaaattgtt atccgctcac    5400
aattccacac aacatacgag ccggaagcat aaagtgtaaa gcctggggtg cctaatgagt    5460
gagctaactc acattaattg cgttgcgctc actgcccgct ttccagtcgg gaaacctgtc    5520
gtgccagctg cattaatgaa tcggccaacg cgcggggaga ggcggtttgc gtattgggcg    5580
ctcttccgct tcctcgctca ctgactcgct gcgctcggtc gttcggctgc ggcgagcggt    5640
atcagctcac tcaaaggcgg taatacggtt atccacagaa tcaggggata acgcaggaaa    5700
gaacatgtga gcaaaaggcc agcaaaaggc caggaaccgt aaaaaggccg cgttgctggc    5760
gtttttccat aggctccgcc ccctgacga gcatcacaaa aatcgacgct caagtcagag     5820
gtggcgaaac ccgacaggac tataaagata ccaggcgttt ccccctggaa gctccctcgt    5880
gcgctctcct gttccgaccc tgccgcttac cggatacctg tccgcctttc tcccttcggg    5940
aagcgtggcg ctttctcata gctcacgctg taggtatctc agttcggtgt aggtcgttcg    6000
ctccaagctg ggctgtgtgc acgaaccccc cgttcagccc gaccgctgcg ccttatccgg    6060
taactatcgt cttgagtcca acccggtaag acacgactta tcgccactgg cagcagccac    6120
tggtaacagg attagcagag cgaggtatgt aggcggtgct acagagttct tgaagtggtg    6180
gcctaactac ggctacacta agaacagt atttggtatc tgcgctctgc tgaagccagt     6240
taccttcgga aaagagttg gtagctcttg atccggcaaa caaaccaccg ctggtagcgg     6300
tggttttttt gtttgcaagc agcagattac gcgcagaaaa aaggatctc aagaagatcc     6360
tttgatcttt tctacggggt ctgacgctca gtggaacgaa aactcacgtt aagggatttt    6420
ggtcatgaga ttatcaaaaa ggatcttcac ctagatcctt ttaaattaaa aatgaagttt    6480
taaatcaatc taaagtatat atgagtaaac ttggtctgac agttaccaat gcttaatcag    6540
tgaggcacct atctcagcga tctgtctatt tcgttcatcc atagttgcct gactccccgt    6600
cgtgtagata actacgatac gggagggctt accatctggc cccagtgctg caatgatacc    6660
gcgagaacca cgctcaccgg ctccagattt atcagcaata aaccagccag ccggaagggc    6720
cgagcgcaga agtggtcctg caactttatc cgcctccatc cagtctatta attgttgccg    6780
ggaagctaga gtaagtagtt cgccagttaa tagtttgcgc aacgttgttg ccattgctac    6840
aggcatcgtg gtgtcacgct cgtcgtttgg tatggcttca ttcagctccg gttcccaacg    6900
atcaaggcga gttacatgat cccccatgtt gtgcaaaaaa gcggttagct ccttcggtcc    6960
tccgatcgtt gtcagaagta agttggccgc agtgttatca ctcatggtta tggcagcact    7020
gcataattct cttactgtca tgccatccgt aagatgcttt tctgtgactg gtgagtactc    7080
aaccaagtca ttctgagaat agtgtatgcg gcgaccgagt tgctcttgcc cggcgtcaat    7140
acgggataat accgcgccac atagcagaac tttaaaagtg ctcatcattg gaaaacgttc    7200
ttcggggcga aaactctcaa ggatcttacc gctgttgaga tccagttcga tgtaacccac    7260
tcgtgcaccc aactgatctt cagcatcttt tactttcacc agcgtttctg ggtgagcaaa    7320
aacaggaagg caaaatgccg caaaaaaggg aataagggcg acacggaaat gttgaatact    7380
catactcttc ctttttcaat attattgaag catttatcag ggttattgtc tcatgagcgg    7440
atacatattt gaatgtattt agaaaaataa acaaataggg gttccgcgca catttccccg    7500
```

```
aaaagtgcca cctgacgtct aagaaaccat tattatcatg acattaacct ataaaaatag    7560
gcgtatcacg aggcccttc gggtcgcgcg tttcggtgat gacggtgaaa acctctgaca    7620
catgcagctc ccgttgacgg tcacagcttg tctgtaagcg gatgccggga gcagacaagc    7680
ccgtcagggc gcgtcagcgg gtgttggcgg gtgtcggggc tggcttaact atgcggcatc    7740
agagcagatt gtactgagag tgcaccataa aattgtaaac gttaatattt tgttaaaatt    7800
cgcgttaaat ttttgttaaa tcagctcatt ttttaaccaa taggccgaaa tcggcaaaat    7860
cccttataaa tcaaaagaat agcccgagat agggttgagt gttgttccag tttggaacaa    7920
gagtccacta ttaaagaacg tggactccaa cgtcaaaggg cgaaaaaccg tctatcaggg    7980
cgatggccca ctacgtgaac catcacccaa atcaagtttt tggggtcga ggtgccgtaa    8040 agcactaaat cggaaccta aagggagccc ccgatttaga gcttgacggg gaaagccggc    8100
gaacgtggcg agaaaggaag ggaagaaagc gaaaggagcg ggcgctaggg cgctggcaag    8160
tgtagcggtc acgctgcgcg taaccaccac acccgccgcg cttaatgcgc cgctacaggg    8220
cgcgtactat ggttgctttg acgtatgcgg tgtgaaatac cgcacagatg cgtaaggaga    8280
aaataccgca tcaggcgcca ttcgccattc aggctgcgca actgttggga agggcgatcg    8340
gtgcgggcct cttcgctatt acgccagctg gcgaaagggg gatgtgctgc aaggcgatta    8400
agttgggtaa cgccagggtt ttcccagtca cgacgttgta aaacgacggc cagtgaattc    8460
catggtctca actttc                                                   8476

<210> SEQ ID NO 50
<211> LENGTH: 7290
<212> TYPE: DNA
<213> ORGANISM: Artificial Sequence
<220> FEATURE:
<223> OTHER INFORMATION: Synthetic polynucleotide

<400> SEQUENCE: 50
tcgcgcgttt cggtgatgac ggtgaaaacc tctgacacat gcagctcccg agacggtca      60 cagcttgtct gtaagcggat gccgggagca gacaagcccg tcaggcgcg tcagcgggtg    120 ttggcgggtg tcgggctgg cttaactatg cggcatcaga gcagattgta ctgagagtgc    180
accatatgcg gtgtgaaata ccgcacagat gcgtaaggag aaaataccgc atcaggcgcc    240
attcgccatt caggctgcgc aactgttggg aagggcgatc ggtgcgggcc tcttcgctat    300
tacgccagct ggcgaaaggg ggatgtgctg caaggcgatt aagttgggta acgccagggt    360
tttcccagtc acgacgttgt aaaacgacgg ccagtgaatt gacgcgtgtt ggcattgatt    420
attgactagt tattaatagt aatcaattac ggggtcatta gttcatagcc catatatgga    480
gttccgcgtt acataactta cggtaaatgg cccgcctggc tgaccgccca acgacccccg    540
cccattgacg tcaataatga cgtatgttcc catagtaacg ccaatagga cttttccattg    600 acgtcaatgg gtggagtatt tacgtaaac tgcccacttg gcagtacatc aagtgtatca    660
tatgccaagt acgccccta ttgacgtcaa tgacggtaaa tggcccgcct ggcattatgc    720
ccagtacatg accttatggg actttcctac ttggcagtac atctacgtat tagtcatcgc    780
tattaccatg gtgatgcggt tttggcagta catcaatggg cgtggatagc ggtttgactc    840
acggggattt ccaagtctcc accccattga cgtcaatggg agtttgtttt ggcaccaaaa    900
tcaacgggac tttccaaaat gtcgtaacaa ctccgcccca ttgacgcaaa tgggcggtag    960
gcgtgtacgg tgggaggtct atataagcag agctcgttta gtgaaccgtc agataactgc   1020
```

```
aggtcgacga tatcgcggcc gccaccatgt tcccgttcca gccaatgtat ccgatgcagc    1080
caatgcccta tcgcaacccg ttcgcggccc cgcgcaggcc ctggttcccc agaaccgacc    1140
cttttctggc gatgcaggtg caggaattaa cccgctcgat ggctaacctg acgttcaagc    1200
aacgccggga cgcgccacct gaggggccat ccgctaataa accgaagaag gaggcctcgc    1260
aaaaacagaa aggggaggc caagggaaga agaagaagaa ccaagggaag aagaaggcta    1320
agacagggcc gcctaatccg aaggcacaga atggaaacaa gaagaagacc aacaagaaac    1380
caggcaagag acagcgcatg gtcatgaaat tggaatctga caagacgttc ccaatcatgt    1440
tggaagggaa gataaacggc tacgcttgtg tggtcggagg gaagttattc aggccgatgc    1500
atgtggaagg caagatcgac aacgacgttc tggccgcgct taagacgaag aaagcatcca    1560
aatacgatct tgagtatgca gatgtgccac agaacatgcg ggccgataca ttcaaataca    1620
cccatgagaa accccaaggc tattacagct ggcatcatgg agcagtccaa tatgaaaatg    1680
ggcgtttcac ggtgccgaaa ggagttgggg ccaagggaga cagcggacga cccattctgg    1740
ataaccaggg acgggtggtc gctattgtgc tgggaggtgt gaatgaagga tctaggacag    1800
cccttttcag tcgtcatgtgg aacgagaagg gagttaccgt gaagtatact ccagagaact    1860
gcgagcaatg gtcactagtg accaccatgt gtctgctcgc caatgtgacg ttcccatgtg    1920
ctcaaccacc aatttgctac gacagaaaac cagcagagac tttggccatg ctcagcgtta    1980
acgttgacaa cccgggctac gatgagctgc tggaagcagc tgttaagtgc cccggaagga    2040
aaaggagatc caccgaggag ctgtttaatg agtataagct aacgcgccct tacatggcca    2100
gatgcatcag atgtgcagtt gggagctgcc atagtccaat agcaatcgag gcagtaaaga    2160
gcgacgggca cgacggttat gttagacttc agacttcctc gcagtatggc ctggattcct    2220
ccggcaactt aaagggcagg accatgcggt atgacatgca cggaccatt aaagagatac    2280 cactacatca agtgtcactc tatacatctc gcccgtgtca cattgtggat gggcacggtt    2340
atttcctgct tgccaggtgc ccggcagggg actccatcac catggaattt aagaaagatt    2400
ccgtcagaca ctcctgctcg gtgccgtatg aagtgaaatt taatcctgta ggcagagaac    2460
tctatactca tcccccagaa cacggagtag agcaagcgtg ccaagtctac gcacatgatg    2520
cacagaacag aggagcttat gtcgagatgc acctcccggg ctcagaagtg gacagcagtt    2580
tggtttcctt gagcggcagt tccggaggct gcatcatcag ctacggcgga gccgactact    2640
gcggcggatc ctcagtcacc gtgacacctc ctgatgggac tagcgccctg gtggaatgcg    2700
agtgtggcgg cacaaagatc tccgagacca tcaacaagac aaaacagttc agccagtgca    2760
caaagaagga gcagtgcaga gcatatcggc tgcagaacga taagtgggtg tataattctg    2820
acaaactgcc caaagcagcg ggagccacct taaaaggaaa actgcatgtc ccattcttgc    2880
tggcagacgg caaatgcacc gtgcctctag caccagaacc tatgataacc ttcggtttca    2940
gatcagtgtc actgaaactg caccctaaga atcccacata tctaatcacc cgccaacttg    3000
ctgatgagcc tcactacacg cacgagctca tatctgaacc agctgttagg aattttaccg    3060
tcaccgaaaa agggtgggag tttgtatggg gaaaccaccc gccgaaaagg ttttgggcac    3120
aggaaacagc acccggaaat ccacatggcc taccgcacga ggtgataact cattattacc    3180
acagataccc tatgtccacc atcctggggt tgtcaatttg tgccgccatt gcaaccgttt    3240
ccgttgcagc gtctacctgg ctgttttgca gatcaagagt tgcgtgccta actccttacc    3300
ggctaacacc taacgctagg ataccatttt gtctggctgt gctttgctgc gcccgcactg    3360
cccgggccga gaccacctgg gagtccttgg atcacctatg gaacaataac caacagatgt    3420
```

-continued

```
tctggattca attgctgatc cctctggccg ccttgatcgt agtgactcgc ctgctcaggt    3480
gcgtgtgctg tgtcgtgcct tttttagtca tggccggcgc cgcaggcgcc ggcgcctacg    3540
agcacgcgac cacgatgccg agccaagcgg gaatctcgta taacactata gtcaacagag    3600
caggctacgc accactccct atcagcataa caccaacaaa gatcaagctg atacctacag    3660
tgaacttgga gtacgtcacc tgccactaca aaacaggaat ggattcacca gccatcaaat    3720
gctgcggatc tcaggaatgc actccaactt acaggcctga tgaacagtgc aaagtcttca    3780
caggggttta cccgttcatg tggggtggtg catattgctt ttgcgacact gagaacaccc    3840
aagtcagcaa ggcctacgta atgaaatctg acgactgcct tgcggatcat gctgaagcat    3900
ataaagcgca cacagcctca gtgcaggcgt tcctcaacat cacagtggga gaacactcta    3960
ttgtgactac cgtgtatgtg aatggagaaa ctcctgtgaa tttcaatggg gtcaaaataa    4020
ctgcaggtcc gctttccaca gcttggacac cctttgatcg caaaatcgtg cagtatgccg    4080
gggagatata taattatgat tttcctgagt atggggcagg acaaccagga gcatttggag    4140
atatacaatc cagaacagtc tcaagctctg atctgtatgc caataccaac ctagtgctgc    4200
agagacccaa agcaggagcg atccacgtgc catacactca ggcaccttcg ggttttgagc    4260
aatggaagaa agataaagct ccatcattga aatttaccgc cccctttcgga tgcgaaatat    4320 atacaaaccc cattcgcgcc gaaaactgtg ctgtagggtc aattccatta gcctttgaca    4380
ttcccgacgc cttgttcacc agggtgtcag aaacaccgac actttcagcg gccgaatgca    4440
ctcttaacga gtgcgtgtat tcttccgact ttggtgggat cgccacggtc aagtactcgg    4500
ccagcaagtc aggcaagtgc gcagtccatg tgccatcagg gactgctacc ctaaaagaag    4560
cagcagtcga gctaaccgag caagggtcgg cgactatcca tttctcgacc gcaaatatcc    4620
acccggagtt caggctccaa atatgcacat catatgttac gtgcaaaggt gattgtcacc    4680
ccccgaaaga ccatattgtg acacaccctc agtatcacgc ccaaacattt acagccgcgg    4740
tgtcaaaaac cgcgtggacg tggttaacat ccctgctggg aggatcagcc gtaattatta    4800
taattggctt ggtgctggct actattgtgg ccatgtacgt gctgaccaac cagaaacata    4860
attaaggatc tagatctgct gtgccttcta gttgccagcc atctgttgtt tgcccctccc    4920
ccgtgccttc cttgaccctg gaaggtgcca ctcccactgt cctttcctaa taaaatgagg    4980
aaattgcatc gcattgtctg agtaggtgtc attctattct ggggggtggg gtggggcagg    5040
acagcaaggg ggaggattgg gaagacaata gcaggcatgc tggggatgcg gtgggctcta    5100
tggctcgagc atggtcatag ctgtttcctg tgtgaaattg ttatccgctc acaattccac    5160
acaacatacg agccggaagc ataaagtgta aagcctgggg tgcctaatga gtgagctaac    5220
tcacattaat tgcgttgcgc tcactgcccg ctttccagtc gggaaacctg tcgtgccagc    5280
tgcattaatg aatcggccaa cgcgcgggga gaggcggttt gcgtattggg cgctcttccg    5340
cttcctcgct cactgactcg ctgcgctcgg tcgttcggct gcggcgagcg gtatcagctc    5400
actcaaaggc ggtaatacgg ttatccacag aatcagggga taacgcagga aagaacatgt    5460
gagcaaaagg ccagcaaaag gccaggaacc gtaaaaaggc cgcgttgctg gcgttttttcc    5520 ataggctccg cccccctgac gagcatcaca aaaatcgacg ctcaagtcag aggtggcgaa    5580
acccgacagg actataaaga taccaggcgt ttccccctgg aagctccctc gtgcgctctc    5640
ctgttccgac cctgccgctt accggatacc tgtccgcctt ctcccttcg ggaagcgtgg    5700 cgctttctca tagctcacgc tgtaggtatc tcagttcggt gtaggtcgtt cgctccaagc    5760
```

```
tgggctgtgt gcacgaaccc cccgttcagc ccgaccgctg cgccttatcc ggtaactatc      5820
gtcttgagtc caacccggta agacacgact tatcgccact ggcagcagcc actggtaaca      5880
ggattagcag agcgaggtat gtaggcggtg ctacagagtt cttgaagtgg tggcctaact      5940
acggctacac tagaagaaca gtatttggta tctgcgctct gctgaagcca gttaccttcg      6000
gaaaaagagt tggtagctct tgatccggca acaaaccac cgctggtagc ggtggttttt       6060
ttgtttgcaa gcagcagatt acgcgcagaa aaaaggatc tcaagaagat cctttgatct       6120
tttctacggg gtctgacgct cagtggaacg aaaactcacg ttaagggatt ttggtcatga      6180
gattatcaaa aaggatcttc acctagatcc ttttaaatta aaaatgaagt tttaaatcaa      6240
tctaaagtat atatgagtaa acttggtctg acagttagaa aaactcatcg agcatcaaat      6300
gaaactgcaa tttattcata tcaggattat caataccata tttttgaaaa agccgtttct      6360
gtaatgaagg agaaaactca ccgaggcagt tccataggat ggcaagatcc tggtatcggt      6420
ctgcgattcc gactcgtcca acatcaatac aacctattaa tttcccctcg tcaaaaataa      6480
ggttatcaag tgagaaatca ccatgagtga cgactgaatc cggtgagaat ggcaaaagtt      6540
tatgcatttc tttccagact tgttcaacag gccagccatt acgctcgtca tcaaaatcac      6600
tcgcatcaac caaaccgtta ttcattcgtg attgcgcctg agcgagacga atacgcgat       6660 cgctgttaaa aggacaatta caaacaggaa tcgaatgcaa ccggcgcagg aacactgcca      6720
gcgcatcaac aatattttca cctgaatcag gatattcttc taatacctgg aatgctgttt      6780
tcccagggat cgcagtggtg agtaaccatg catcatcagg agtacggata aaatgcttga      6840
tggtcggaag aggcataaat tccgtcagcc agtttagtct gaccatctca tctgtaacat      6900
cattggcaac gctacctttg ccatgtttca gaaacaactc tggcgcatcg gcttcccat       6960 acaatcgata gattgtcgca cctgattgcc cgacattatc gcgagcccat ttataccat       7020 ataaatcagc atccatgttg gaatttaatc gcggcctaga gcaagacgtt tcccgttgaa      7080
tatggctcat actcttcctt tttcaatatt attgaagcat ttatcagggt tattgtctca      7140
tgagcggata catatttgaa tgtatttaga aaaataaaca aataggggtt ccgcgcacat      7200
ttccccgaaa agtgccacct gacgtctaag aaaccattat tatcatgaca ttaacctata      7260
aaaataggcg tatcacgagg ccctttcgtc                                       7290

<210> SEQ ID NO 51
<211> LENGTH: 72
<212> TYPE: DNA
<213> ORGANISM: Artificial Sequence
<220> FEATURE:
<223> OTHER INFORMATION: Synthetic polynucleotide

<400> SEQUENCE: 51
tccggaggac taaactggta ccgcatgagc cccagcaacc agacggacaa gctggccgcc      60
ttcggaggat cc                                                          72

<210> SEQ ID NO 52
<211> LENGTH: 24
<212> TYPE: PRT
<213> ORGANISM: Artificial Sequence
<220> FEATURE:
<223> OTHER INFORMATION: Synthetic peptide

<400> SEQUENCE: 52

Ser Gly Gly Leu Asn Trp Tyr Arg Met Ser Pro Ser Asn Gln Thr Asp
1               5                   10                  15
```

Lys Leu Ala Ala Phe Gly Gly Ser
            20

<210> SEQ ID NO 53
<211> LENGTH: 78
<212> TYPE: DNA
<213> ORGANISM: Artificial Sequence
<220> FEATURE:
<223> OTHER INFORMATION: Synthetic polynucleotide

<400> SEQUENCE: 53
tccggaggaa tgctaaactg gtaccgcatg agccccagca accagacgga caagctggcc    60
gccttctcag gaggatcc                                                 78

<210> SEQ ID NO 54
<211> LENGTH: 26
<212> TYPE: PRT
<213> ORGANISM: Artificial Sequence
<220> FEATURE:
<223> OTHER INFORMATION: Synthetic peptide

<400> SEQUENCE: 54

Ser Gly Gly Met Leu Asn Trp Tyr Arg Met Ser Pro Ser Asn Gln Thr
1               5                   10                  15

Asp Lys Leu Ala Ala Phe Ser Gly Gly Ser
            20                  25

<210> SEQ ID NO 55
<211> LENGTH: 78
<212> TYPE: DNA
<213> ORGANISM: Artificial Sequence
<220> FEATURE:
<223> OTHER INFORMATION: Synthetic polynucleotide

<400> SEQUENCE: 55
tccggaggag tgctaaactg gtaccgcatg agccccagca accagacgga caagctggcc    60
gccttccccg gaggatcc                                                 78

<210> SEQ ID NO 56
<211> LENGTH: 26
<212> TYPE: PRT
<213> ORGANISM: Artificial Sequence
<220> FEATURE:
<223> OTHER INFORMATION: Synthetic peptide

<400> SEQUENCE: 56

Ser Gly Gly Val Leu Asn Trp Tyr Arg Met Ser Pro Ser Asn Gln Thr
1               5                   10                  15

Asp Lys Leu Ala Ala Phe Pro Gly Gly Ser
            20                  25

<210> SEQ ID NO 57
<211> LENGTH: 48
<212> TYPE: DNA
<213> ORGANISM: Artificial Sequence
<220> FEATURE:
<223> OTHER INFORMATION: Synthetic polynucleotide

<400> SEQUENCE: 57
tccggaggat gcatcatcag ctacggcgga gccgactacg gaggatcc                48

<210> SEQ ID NO 58
<211> LENGTH: 17
<212> TYPE: PRT

```
<213> ORGANISM: Artificial Sequence
<220> FEATURE:
<223> OTHER INFORMATION: Synthetic peptide

<400> SEQUENCE: 58

Ser Gly Gly Cys Ile Ile Ser Tyr Gly Gly Ala Asp Tyr Cys Gly Gly
1               5                   10                  15

Ser

<210> SEQ ID NO 59
<211> LENGTH: 60
<212> TYPE: DNA
<213> ORGANISM: Artificial Sequence
<220> FEATURE:
<223> OTHER INFORMATION: Synthetic polynucleotide

<400> SEQUENCE: 59
tccggaggag gcgccatcag cctgcacccc aaggccaaga tcgaggaatc tggaggatcc      60

<210> SEQ ID NO 60
<211> LENGTH: 19
<212> TYPE: PRT
<213> ORGANISM: Artificial Sequence
<220> FEATURE:
<223> OTHER INFORMATION: Synthetic peptide

<400> SEQUENCE: 60

Ser Gly Gly Gly Ala Ile Ser Leu His Pro Lys Ala Lys Ile Glu Glu
1               5                   10                  15

Ser Gly Ser

<210> SEQ ID NO 61
<211> LENGTH: 60
<212> TYPE: DNA
<213> ORGANISM: Artificial Sequence
<220> FEATURE:
<223> OTHER INFORMATION: Synthetic polynucleotide

<400> SEQUENCE: 61
tccggaggat gtggcgccat cagcctgcac cccaaggcca agatcgagga aggaggatcc      60

<210> SEQ ID NO 62
<211> LENGTH: 21
<212> TYPE: PRT
<213> ORGANISM: Artificial Sequence
<220> FEATURE:
<223> OTHER INFORMATION: Synthetic peptide

<400> SEQUENCE: 62

Ser Gly Gly Cys Gly Ala Ile Ser Leu His Pro Lys Ala Lys Ile Glu
1               5                   10                  15

Glu Cys Gly Gly Ser
            20

<210> SEQ ID NO 63
<211> LENGTH: 3747
<212> TYPE: DNA
<213> ORGANISM: Chikungunya virus

<400> SEQUENCE: 63
atggagttca tcccaaccca aactttttac aataggaggt accagcctcg accctggact      60
ccgcgcccta ctatccaagt catcaggccc agaccgcgcc tcagaggca agctgggcaa      120 cttgcccagc tgatctcagc agttaataaa ctgacaatgc gcgcggtacc acaacagaag     180
```

```
ccacgcagga atcggaagaa taagaagcaa agcaaaaac aacaggcgcc acaaaacaac      240
acaaatcaaa agaagcagcc acctaaaaag aaaccggctc aaaagaaaaa gaagccgggc      300
cgcagagaga ggatgtgcat gaaaatcgaa aatgattgta ttttcgaagt caagcacgaa      360
ggtaaggtaa caggttacgc gtgcctggtg ggggacaaag taatgaaacc agcacacgta      420
aaggggacca tcgataacgc ggacctggcc aaactggcct ttaagcggtc atctaagtat      480
gaccttgaat gcgcgcagat acccgtgcac atgaagtccg acgcttcgaa gttcacccat      540
gagaaaccgg aggggtacta caactggcac cacggagcag tacagtactc aggaggccgg      600
ttcaccatcc ctacaggtgc tggcaaacca ggggacagcg gcagaccgat cttcgacaac      660
aagggacgcg tggtggccat agtcttagga ggagctaatg aaggagcccg tacagccctc      720
tcggtggtga cctggaataa agacattgtc actaaaatca cccccgaggg ggccgaagag      780
tggagtcttg ccatcccagt tatgtgcctg ttggcaaaca ccacgttccc ctgctcccag      840 ccccctttgca cgccctgctg ctacgaaaag gaaccggagg aaaccctacg catgcttgag      900
gacaacgtca tgagacctgg gtactatcag ctgctacaag catccttaac atgttctccc      960
caccgccagc gacgcagcac caaggacaac ttcaatgtct ataaagccac aagaccatac     1020
ttagctcact gtcccgactg tggagaaggg cactcgtgcc atagtcccgt agcactagaa     1080
cgcatcagaa atgaagcgac agacgggacg ctgaaaatcc aggtctcctt gcaaatcgga     1140
ataaagacgg atgacagcca cgattggacc aagctgcgtt atatggacaa ccacatgcca     1200
gcagacgcag agagggcggg gctatttgta agaacatcag caccgtgtac gattactgga     1260
acaatgggac acttcatcct ggcccgatgt ccaaaagggg aaactctgac ggtgggattc     1320
actgacagta ggaagattag tcactcatgt acgcacccat ttcaccacga ccctcctgtg     1380
ataggtcggg aaaaattcca ttcccgaccg cagcacggta aagagctacc ttgcagcacg     1440
tacgtgcaga gcaccgccgc aactaccgag gagatagagg tacacatgcc cccagacacc     1500
cctgatcgca cattaatgtc acaacagtcc ggcaacgtaa agatcacagt caatggccag     1560
acggtgcggt acaagtgtaa ttgcggtggc tcaaatgaag gactaacaac tacagacaaa     1620
gtgattaata actgcaaggt tgatcaatgt catgccgcgg tcaccaatca caaaaagtgg     1680
cagtataact cccctctggt cccgcgtaat gctgaacttg gggaccgaaa aggaaaaatt     1740
cacatcccgt ttccgctggc aaatgtaaca tgcagggtgc ctaaagcaag gaaccccacc     1800
gtgacgtacg ggaaaaacca agtcatcatg ctactgtatc ctgaccaccc aacactcctg     1860
tcctaccgga atatgggaga agaaccaaac tatcaagaag agtgggtgat gcataagaag     1920
gaagtcgtgc taaccgtgcc gactgaaggg ctcgaggtca cgtggggcaa caacgagccg     1980
tataagtatt ggccgcagtt atctacaaac ggtacagccc atggccaccc gcatgagata     2040
attctgtatt attatgagct gtaccccact atgactgtag tagttgtgtc agtggccacg     2100
ttcatactcc tgtcgatggt gggtatggca gcggggatgt gcatgtgtgc acgacgcaga     2160
tgcatcacac cgtatgaact gacaccagga gctaccgtcc ctttcctgct tagcctaata     2220
tgctgcatca gaacagctaa agcggccaca taccaagagg ctgcgatata cctgtggaac     2280
gagcagcaac cttgtttttg gctacaagcc cttattccgc tggcagccct gattgttcta     2340
tgcaactgtc tgagactctt accatgctgc tgtaaaacgt tggcttttttt agccgtaatg     2400 agcgtcggtg cccacactgt gagcgcgtac gaacacgtaa cagtgatccc gaacacggtg     2460
ggagtaccgt ataagactct agtcaataga cctggctaca gccccatggt attggagatg     2520
```

```
gaactactgt cagtcacttt ggagccaaca ctatcgcttg attacatcac gtgcgagtac    2580
aaaaccgtca tcccgtctcc gtacgtgaag tgctgcggta cagcagagtg caaggacaaa    2640
aacctacctg actacagctg taaggtcttc accggcgtct acccatttat gtggggcggc    2700
gcctactgct tctgcgacgc tgaaaacacg cagttgagcg aagcacacgt ggagaagtcc    2760
gaatcatgca aaacagaatt tgcatcagca tacagggctc ataccgcatc tgcatcagct    2820
aagctccgcg tcctttacca aggaaataac atcactgtaa ctgccatgc aaacggcgac    2880 catgccgtca cagttaagga cgccaaattc attgtggggc caatgtcttc agcctggaca    2940
cctttcgaca caaaattgt ggtgtacaaa ggtgacgtct ataacatgga ctacccgccc    3000
tttggcgcag gaagaccagg acaatttggc gatatccaaa gtcgcacacc tgagagtaaa    3060
gacgtctatg ctaatacaca actggtactg cagagaccgg ctgtgggtac ggtacacgtg    3120
ccatactctc aggcaccatc tggctttaag tattggctaa agaacgcgg ggcgtcgctg     3180 cagcacacag caccatttgg ctgccaaata gcaacaaacc cggtaagagc ggtgaactgc    3240
gccgtaggga acatgcccat ctccatcgac ataccggaag cggccttcac tagggtcgtc    3300
gacgcgccct ctttaacgga catgtcgtgc gaggtaccag cctgcaccca ttcctcagac    3360
tttgggggcg tcgccattat taaatatgca gccagcaaga aggcaagtg tgcggtgcat    3420 tcgatgacta acgccgtcac tattcgggaa gctgagatag aagttgaagg gaattctcag    3480
ctgcaaatct ctttctcgac ggccttagcc agcgccgaat ccgcgtaca gtctgttct     3540 acacaagtac actgtgcagc cgagtgccac cccccgaagg accacatagt caactacccg    3600
gcgtcacata ccaccctcgg ggtccaggac atctccgcta cggcgatgtc atgggtgcag    3660
aagatcacgg gaggtgtggg actggttgtt gctgttgccg cactgattct aatcgtggtg    3720
ctatgcgtgt cgttcagcag gcactaa                                        3747
```

<210> SEQ ID NO 64
<211> LENGTH: 3765
<212> TYPE: DNA
<213> ORGANISM: Venezuelan equine encephalitis virus

<400> SEQUENCE: 64

```
atgttcccgt ccagccaat gtatccgatg cagccaatgc cctatcgcaa cccgttcgcg     60
gccccgcgca ggccctggtt ccccagaacc gacccttttc tggcgatgca ggtgcaggaa    120
ttaacccgct cgatggctaa cctgacgttc aagcaacgcc gggacgcgcc acctgagggg    180
ccatccgcta taaaccgaa gaaggaggcc tcgcaaaaac agaaaggggg aggccaaggg    240
aagaagaaga agaaccaagg gaagaagaag gctaagacag ggccgcctaa tccgaaggca    300
cagaatggaa acaagaagaa gaccaacaag aaaccaggca agacagcg catggtcatg    360 aaattggaat ctgacaagac gttcccaatc atgttggaag ggaagataaa cggctacgct    420
tgtgtggtcg gagggaagtt attcaggccg atgcatgtgg aaggcaagat cgacaacgac    480
gttctggccg cgcttaagac gaagaaagca tccaaatacg atcttgagta tgcagatgtg    540
ccacagaaca tgcgggccga tacattcaaa tacacccatg agaaccccca ggctattac    600 agctggcatc atgagcagt ccaatatgaa aatgggcgtt tcacggtgcc gaaaggagtt    660
ggggccaagg gagacagcgg acgacccatt ctggataacc agggacgggt ggtcgctatt    720
gtgctgggag gtgtgaatga aggatctagg acagcccttt cagtcgtcat gtggaacgag    780
aagggagtta ccgtgaagta tactccggag aactgcgagc aatggtcact agtgaccacc    840
atgtgtctgc tcgccaatgt gacgttccca tgtgctcaac accaatttg ctacgacaga    900
```

```
aaaccagcag agactttggc catgctcagc gttaacgttg acaacccggg ctacgatgag      960
ctgctggaag cagctgttaa gtgccccgga aggaaaagga gatccaccga ggagctgttt     1020
aatgagtata agctaacgcg cccttacatg gccagatgca tcagatgtgc agttgggagc     1080
tgccatagtc caatagcaat cgaggcagta aagagcgacg ggcacgacgg ttatgttaga     1140
cttcagactt cctcgcagta tggcctggat tcctccggca acttaaaggg caggaccatg     1200
cggtatgaca tgcacgggac cattaaagag ataccactac atcaagtgtc actctataca     1260
tctcgcccgt gtcacattgt ggatgggcac ggttatttcc tgcttgccag gtgcccggca     1320
ggggactcca tcaccatgga atttaagaaa gattccgtca gacactcctg ctcggtgccg     1380
tatgaagtga aatttaatcc tgtaggcaga gaactctata ctcatccccc agaacacgga     1440
gtagagcaag cgtgccaagt ctacgcacat gatgcacaga acagaggagc ttatgtcgag     1500
atgcacctcc cgggctcaga agtggacagc agtttggttt ccttgagcgg cagttcagtc     1560
accgtgacac tcctgatggg gactagcgcc ctggtggaat gcgagtgtgg cggcacaaag     1620
atctccgaga ccatcaacaa gacaaaacag ttcagccagt gcacaaagaa ggagcagtgc     1680
agagcatatc ggctgcagaa cgataagtgg gtgtataatt ctgacaaact gcccaaagca     1740
gcgggagcca ccttaaaagg aaaactgcat gtcccattct tgctggcaga cggcaaatgc     1800
accgtgcctc tagcaccaga acctatgata accttcggtt tcagatcagt gtcactgaaa     1860
ctgcacccta gaatcccac atatctaatc acccgccaac ttgctgatga gcctcactac     1920
acgcacgagc tcatatctga accagctgtt aggaatttta ccgtcaccga aaaagggtgg     1980
gagtttgtat ggggaaacca cccgccgaaa aggttttggg cacaggaaac agcacccgga     2040
aatccacatg ggctaccgca cgaggtgata actcattatt accacagata ccctatgtcc     2100
accatcctgg gtttgtcaat ttgtgccgcc attgcaaccg tttccgttgc agcgtctacc     2160
tggctgtttt gcagatctag agttgcgtgc ctaactcctt accggctaac acctaacgct     2220
aggataccat tttgtctggc tgtgctttgc tgcgcccgca ctgcccgggc cgagaccacc     2280
tgggagtcct tggatcacct atggaacaat aaccaacaga tgttctggat tcaattgctg     2340
atccctctgg ccgccttgat cgtagtgact cgcctgctca ggtgcgtgtg ctgtgtcgtg     2400
ccttttttag tcatggccgg cgccgcaggc gccggcgcct acgagcacgc gaccacgatg     2460
ccgagccaag cgggaatctc gtataacact atagtcaaca gagcaggcta cgcaccactc     2520
cctatcagca taacaccaac aaagatcaag ctgataccta cagtgaactt ggagtacgtc     2580
acctgccact acaaaacagg aatggattca ccagccatca aatgctgcgg atctcaggaa     2640
tgcactccaa cttacaggcc tgatgaacag tgcaaagtct tcacagggat ttacccgttc     2700
atgtggggtg gtgcatattg cttttgcgac actgagaaca cccaagtcag caaggcctac     2760
gtaatgaaat ctgacgactg ccttgcggat catgctgaag catataaagc gcacacagcc     2820
tcagtgcagg cgttcctcaa catcacagtg ggagaacact ctattgtgac taccgtgtat     2880
gtgaatggag aaactcctgt gaatttcaat ggggtcaaaa taactgcagg tccgctttcc     2940
acagcttgga cacccttga tcgcaaaatc gtgcagtatg ccggggagat ctataattat     3000
gattttcctg agtatgggc aggacaacca ggagcatttg gagatataca atccagaaca     3060
gtctcaagct ctgatctgta tgccaatacc aacctagtgc tgcagagacc caaagcagga     3120
gcgatccacg tgccatacac tcaggcacct tcgggttttg agcaatggaa gaaagataaa     3180
gctccatcat tgaaatttac cgccccttc ggatgcgaaa tatatacaaa ccccattcgc     3240
```

```
gccgaaaact gtgctgtagg gtcaattcca ttagcctttg acattcccga cgccttgttc    3300
accagggtgt cagaaacacc gacactttca gcggccgaat gcactcttaa cgagtgcgtg    3360
tattcttccg actttggtgg gatcgccacg gtcaagtact cggccagcaa gtcaggcaag    3420
tgcgcagtcc atgtgccatc agggactgct accctaaaag aagcagcagt cgagctaacc    3480
gagcaagggt cggcgactat ccatttctcg accgcaaata tccacccgga gttcaggctc    3540
caaatatgca catcatatgt tacgtgcaaa ggtgattgtc acccccgaa agaccatatt     3600 gtgacacacc ctcagtatca cgcccaaaca tttacagccg cggtgtcaaa aaccgcgtgg    3660
acgtggttaa catccctgct gggaggatca gccgtaatta ttataattgg cttggtgctg    3720
gctactattg tggccatgta cgtgctgacc aaccagaaac ataat                    3765
```

VIRUS LIKE PARTICLE COMPRISING PD-1 ANTIGEN OR PD-1 LIGAND ANTIGEN

CROSS REFERENCE TO RELATED APPLICATIONS

This application is a Continuation of U.S. application Ser. No. 14/328,268 (now allowed); which claims the benefit of U.S. Provisional Patent Application No. 61/845,712 filed on Jul. 12, 2013, the entire contents of each of which are incorporated by reference herein.

TECHNICAL FIELD

The present invention relates to a virus like particle comprising a virus structural protein and an antigen derived from PD-1 or a ligand of PD-1, and a composition or a kit comprising thereof, its use in immune response etc.

BACKGROUND ART

Programmed Cell Death 1 or PD-1 (also referred to as PDCD1) is a 50 to 55 kDa type I transmembrane receptor of the CD28 superfamily that negatively regulates T cell antigen receptor signaling by interacting with the specific ligands and is suggested to play a role in the maintenance of self-tolerance.

PD-1 antigen relates to almost every aspect of immune responses including autoimmunity, tumor immunity, infectious immunity, transplantation immunity, allergy and immunological privilege.

PD-1 is expressed on the surface of activated T cells, B cells, and macrophages, (Y. Agata et al., International Immunology vol. 8, No. 5 p 765-772, 1996) suggesting that compared to CTLA-4 that also plays an important regulatory role in the immune system, PD-1 more broadly negatively regulates immune responses.

In general, a need exists to provide safe and effective therapeutic methods for immune disorders such as, for example, autoimmune diseases, inflammatory disorders, allergies, transplant rejection, cancer, immune deficiency, and other immune system-related disorders. Modulation of the immune responses involved in these disorders can be accomplished by manipulation of the PD-1 pathway.

PD-1 has two ligands, PD-L1 (Programmed Death Ligand 1 or PDCD1 L1 or B7-H1) and PD-L2 (Programmed Death Ligand 2 or PDCD1 L2 or B7-DC), which are members of the B7 family ligands.

In one approach, blocking the interaction of PD-1 as well as its ligand (PD-L1, PD-L2 or both) may provide an effective way for tumor and viral immunotherapy.

U.S. Pat. Nos. 5,629,204 and 5,698,520 relate to a membrane protein related to human PD-1 and DNA encoding the said protein, and indicates that PD-1 protein may be useful for the treatment of various infections, immunological depression or acceleration, or tumors etc.

U.S. Pat. No. 7,595,048 and US 2011/0081341 relate to immunopotentiation characterized by inhibiting immunosuppressive signals induced by PD-1, PD-L1 or PD-L2, compositions for cancer or infection treatment, and therapies that use them.

Several big pharmaceutical companies are pitting their PD-1 antibodies against each other in a race to be first to market. Here are 3 monoclonal antibodies such as Merck's Lambrolizumab (MK-3475) which is a humanized monoclonal IgG4 antibody that acts against PD-1, Bristol-Myers Squibb's Nivolumab (BMS-936558) which is fully anti human PD-1 antibody and Roche Genentech's MPDL3280A which doesn't block PD-1, but rather blocks PD-L1.

However, more potent and safe compound targeting PD-1 is strongly desired.

Virus-like particles (VLPs) are multiprotein structures that mimic the organization and conformation of authentic native viruses but lack the viral genome, potentially yielding safer and cheaper vaccine candidates. A handful of prophylactic VLP-based vaccines is currently commercialized worldwide: Glaxo SmithKline's Engerix® (hepatitis B virus) and Cervarix® (human papillomavirus), and Merck and Co., Inc.'s Recombivax HB® (hepatitis B virus) and Gardasil® (human papillomavirus) are some examples. Other VLP-based vaccine candidates are in clinical trials or undergoing preclinical evaluation, such as, influenza virus, parvovirus, Norwalk and various chimeric VLPs. Many others are still restricted to small-scale fundamental research, despite their success in preclinical tests. The implications of large-scale VLP production are discussed in the context of process control, monitorization and optimization. The main up- and down-stream technical challenges are identified and discussed accordingly. Successful VLP-based vaccine blockbusters are briefly presented concomitantly with the latest results from clinical trials and the recent developments in chimeric VLP-based technology for either therapeutic or prophylactic vaccination (Expert Rev. Vaccines 9(10), 1149-1176, 2010).

Chikungunya virus (CHIKV) has infected millions of people in Africa, Europe and Asia since this alphavirus reemerged from Kenya in 2004. The severity of the disease and the spread of this epidemic virus present a serious public health threat in the absence of vaccines or antiviral therapies. It is reported that a VLP vaccine for epidemic Chikungunya virus protects non-human primates against infection (Nat Med. 2010 March; 16(3): 334-338). US patent publication No. 2012/0003266 discloses a virus-like particle (VLP) comprising one or more Chikungunya virus structural proteins which is useful for formulating a vaccine or antigenic composition for Chikungunya that induces immunity to an infection or at least one symptom thereof. WO2012/106356 discloses modified alphavirus or flavivirus virus-like particles (VLPs) and methods for enhancing production of modified VLPs for use in the prevention or treatment of alphavirus and flavivirus-mediated diseases. (these cited references are herein incorporated by reference).

SUMMARY OF INVENTION

In a first aspect, the present invention provides a particle comprising a virus structural protein and an antigen selected from the group consisting of an antigen derived from PD-1 and an antigen derived from a ligand of PD-1.

In a second aspect, the present invention provides a nucleic acid molecule comprising a nucleotide sequence for expressing a particle which comprises a virus structural protein and an antigen selected from the group consisting of an antigen derived from PD-1 and an antigen derived from a ligand of PD-1.

In a third aspect, the present invention provides a pharmaceutical composition and a kit comprising a pharmaceutical composition, wherein the pharmaceutical composition comprises a particle comprising a virus structural protein and an antigen selected from the group consisting of an antigen derived from PD-1 and an antigen derived from a ligand of PD-1; or a nucleic acid molecule comprising a nucleotide sequence for expressing a particle which comprises a virus structural protein and an antigen selected from the group consisting of an antigen derived from PD-1 and an antigen derived from a ligand of PD-1; and a pharmaceutically acceptable carrier.

In a forth aspect, the present invention provides a use of a particle comprising a virus structural protein and an antigen selected from the group consisting of an antigen derived from PD-1 and an antigen derived from a ligand of PD-1; or a nucleic acid molecule comprising a nucleotide sequence for expressing a particle which comprises a virus structural protein and an antigen selected from the group consisting of an antigen derived from PD-1 and an antigen derived from a ligand of PD-1 for the manufacture of a pharmaceutical composition or a kit for modulating an immuno response, treating cancer or treating an infectious disease in a subject.

Figure 1:
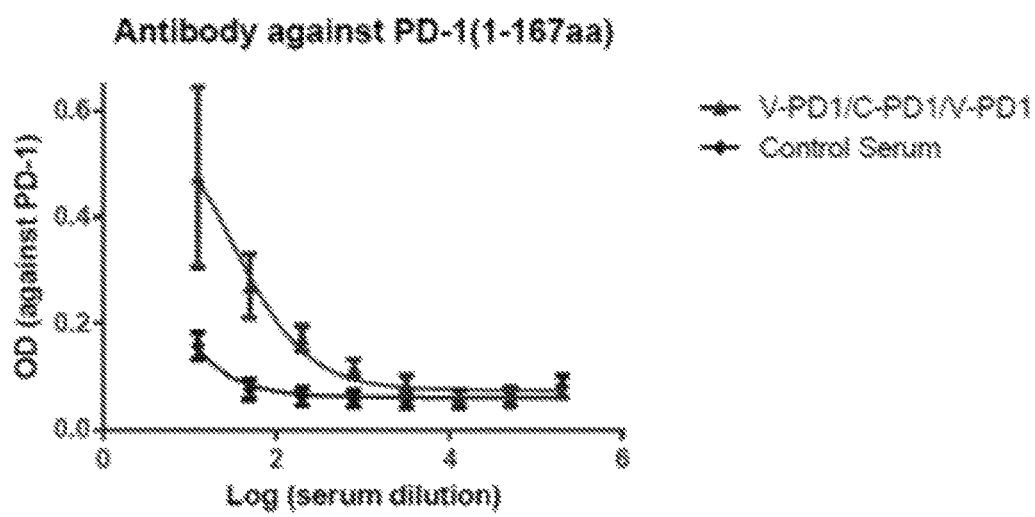
FIG. 1 shows results of ELISA where an antibody which binds to N-terminal PD-1 (1-167aa) was detected.

DESCRIPTION OF EMBODIMENT (1) Particle Comprising a Virus Structural Protein and an Antigen Selected from the Group Consisting of an Antigen Derived from PD-1 and an Antigen Derived from a Ligand of PD-1

In a first aspect, the present invention provides a particle comprising a virus structural protein and an antigen selected from the group consisting of an antigen derived from PD-1 and an antigen derived from a ligand of PD-1.

A derivative of the above-described particle which can be prepared by modifying the above-described particle is also provided by the present invention. Examples of the modification include, but are not limited to, addition, deletion or replacement of one or more amino acid residues.

The particle provided by the present invention may be a particle which consists of or comprises i) at least one virus structural protein and ii) at least one antigen derived from PD-1 or at least one antigen derived from a ligand of PD-1. The at least one virus structural protein may consist of one or more kinds of protein or peptide and spontaneously assembled to form the particle provided by the present invention. In one embodiment, the particle provided by the present invention has a diameter of at least 10 nm, for example, at least 20 nm, preferably at least 50 nm. In one embodiment, molecular weight of the particle is from 100 kDa to 100,000 kDa, preferably from 400 kDa to 30,000 kDa.

Preferably, a virus structural protein used for the present invention may be a virus structural protein derived from Alphavirus or Flavivirus. Thus, the particle provided by the present invention may be a virus like particle including a virus like particle derived from Alphavirus or Flavivirus.

Examples of Alphavirus and Flavivirus include, but not limited to, Aura virus, Babanki virus, Barmah Forest virus (BFV), Bebaru virus, Cabassou virus, Chikungunya virus (CHIKV), Eastern equine encephalitis virus (EEEV), Eilat virus, Everglades virus, Fort Morgan virus, Getah virus, Highlands J virus, Kyzylagach virus, Mayaro virus, Me Tri virus, Middelburg virus, Mosso das Pedras virus, Mucambo virus, Ndumu virus, O'nyong-nyong virus, Pixuna virus, Rio Negro virus, Ross River virus (RRV), Salmon pancreas disease virus, Semliki Forest virus, Sindbis virus, Southern elephant seal virus, Tonate virus, Trocara virus, Una virus, Venezuelan equine encephalitis virus (VEEV), Western equine encephalitis virus (WEEV), Whataroa virus, West Nile virus, dengue virus, tick-borne encephalitis virus and yellow fever virus.

Virus structural protein may be a capsid protein, an envelope protein, a fragment thereof or a complex thereof. Thus, virus structural protein used for the present invention may consist of or comprise a capsid protein and/or an envelope protein and/or a fragment thereof. In one embodiment, the virus like particle provided by the present invention consists of or comprises capsid, E2 and E1. An antigen may be inserted into E2. For example, the virus like particle provided by the present invention may be formed by assembling 240 capsids, 240 E1 proteins and 240 E2 proteins where a PD-1 antigen is inserted into each of E2 proteins.

As used herein, the term "PD-1 antigen" refers to an antigen derived from PD-1. Preferably, PD-1 is a human PD-1. An antigen derived from PD-1 may be a fragment of PD-1 or a derivative of a fragment of PD-1.

As used herein, the term "PD-1 ligand antigen" refers to an antigen derived from a ligand of PD-1. Examples of a ligand of PD-1 include, but are not limited to, PD-L1 and PD-L2. Preferably, a ligand of PD-1 is human PD-L1 or human PD-L2. An antigen derived from PD-L1 or PD-L2 may be a fragment of PD-L1 or PD-L2; or a derivative of a fragment of PD-L1 or PD-L2.

A fragment of PD-1, PD-L1 or PD-L2 for use in an antigen contained in the particle provided by the present invention may be selected based on the amino acid sequence of PD-1, PD-L1 or PD-L2 and/or tertiary structure thereof.

For example, a fragment for use in the antigen may consist of or comprise a fragment located in the surface of PD-1, PD-L1 or PD-L2. Preferably, an antibody against an antigen contained in the particle provided by the present invention blocks an interaction between PD-1 and PD-L1 or PD-1 and PD-L2. A fragment of PD-1, PD-L1 or PD-L2 for use in the antigen may be 10-300 amino acid residues (e.g. 10-120, 10-30 or 15-30 amino acid residues) in length.

In one embodiment, a fragment for use in the antigen may be selected so that spatial distance between the N-terminal residue and C-terminal residue of the antigen is 30 Å or less when the distance is determined in a crystal of the antigen or a naturally occurring protein containing the antigen or modified protein therefrom. For example, an antigen used for the particle provided by the present invention can be designed using a free software including PyMOL (e.g. PyMOL v0.99: http:/www.pymol.org). In one embodiment, a spatial distance between N-terminal residue and C-terminal residue of the antigen is 30 Å (angstrom) or less, 20 Å or less, or 10 Å or less (e.g. from 5 Å to 15 Å, from 5 Å to 12 Å, from 5 Å to 11 Å, from 5 Å to 10 Å, from 5 Å to 8 Å, from 8 Å to 15 Å, from 8 Å to 13 Å, from 8 Å to 12 Å, from 8 Å to 11 Å, from 9 Å to 12 Å, from 9 Å to 11 Å, from 9 Å to 10 Å or from 10 Å to 11 Å).

Examples of a fragment of PD-1 for use in the antigen include, but are not limited to, lnwyrmspsnqtdklaaf (SEQ ID NO: 4), mlnwyrmspsnqtdklaafs (SEQ ID NO: 5), vinwyrmspsnqtdklaafp (SEQ ID NO: 6), gaislhpkakiees (SEQ ID NO: 7), cgaislhpkakieec (SEQ ID NO: 8), VLNWYRMSPSNQTDKLAAF (SEQ ID NO: 9), GAISLAPKAQIKES (SEQ ID NO: 10), RNDSGTYLCGAISLAPKAQIKESLRAELRVT (SEQ ID NO: 11) and RNDSGIYLCGAISLHPKAKIEESPGAELVVT (SEQ ID NO: 12). Examples of a fragment of PD-L1 for use in the antigen include, but are not limited to, ciisyggadyc (SEQ ID NO: 13), CMISYGGADYC (SEQ ID NO: 14), LQDAGVYRCMISYG- GADYKRITVKVN (SEQ ID NO: 15), LQDAGVYRAMI-SYGGADYKRITVKVN (SEQ ID NO: 16), DLAALIVYWEMEDKNIIQFVH (SEQ ID NO: 17), DLAALIVYWEMEDKNIIQFVHGG (SEQ ID NO: 18), FTVTVPKDLYVVEYGSNMTIECKFPVE (SEQ ID NO: 19), Lqdagvycciisyggadykritlkvn (SEQ ID NO: 20), lqdagvyaaiisyggadykritlkvn (SEQ ID NO: 21), dllalvvywekedeqviqfva (SEQ ID NO: 22), dllalvvywekedeqviqfvagg (SEQ ID NO: 23) and ftitapkdlyvveygsnvtmecrfpve (SEQ ID NO: 24).

A derivative of a fragment of PD-1, PD-L1 or PD-L2 may be prepared by addition, deletion or replacement of one or several amino acid residues in the fragment of PD-1, PD-L1 or PD-L2. In one embodiment, a derivative of a fragment of PD-1, PD-L1 or PD-L2 has at least 70%, 75%, 80%, 85%, 90%, 95% or 98% amino acid sequence identity to the corresponding fragment of a naturally occurring PD-1, PD-L1 or PD-L2. In one embodiment, a derivative of a fragment of PD-1, PD-L1 or PD-L2 is a mutant where at most 10% of the amino acids are deleted, substituted, and/or added based on the corresponding fragment of naturally occurring PD-1, PD-L1 or PD-L2.

In the particle as provided by the present invention, a virus structural protein and an antigen may be linked through at least one first attachment site which is present in the virus structural protein and at least one second attachment site which is present in the antigen.

As used herein, each of "a first attachment site" and "a second attachment site" refers to a site where more than one substance is linked each other.

In one embodiment, a virus structural protein and an antigen are directly fused. In one embodiment, one or two linkers may intervene between N-terminal residue of an antigen and a virus structural protein and/or between C-terminal residue of an antigen and a virus structural protein.

An antigen or a virus structural protein can be truncated and replaced by short linkers. In some embodiments, an antigen or a virus structural protein include one or more peptide linkers. Typically, a linker consists of from 2 to 25 amino acids. Usually, it is from 2 to 15 amino acids in length, although in certain circumstances, it can be only one, such as a single glycine residue.

In one embodiment, a nucleic acid molecule, in which polynucleotide encoding the virus structural protein is genetically fused with polynucleotide encoding the antigen, is expressed in a host cell so that the first attachment site and the second attachment site are linked through a peptide bond. In this case, the virus structural protein and the antigen are linked through a peptide bond. Relating to this embodiment, the first attachment site and/or the second attachment site may be genetically modified from the original protein or antigen. For example, the first attachment site is modified from the virus structural protein so that through a linker peptide including SG, GS, SGG, GGS and SGSG, the protein is conjugated with the antigen.

When the virus structural protein are chemically conjugated with the antigen, the first attachment site and the second attachment site may be linked through a chemical cross-linker which is a chemical compound.

Examples of the cross-linker include, but are not limited to, SMPH, Sulfo-MBS, Sulfo-EMCS, Sulfo-GMBS, Sulfo-SIAB, Sulfo-SMPB, Sulfo-SMCC, SVSB, SIA and other cross-linkers available from the Pierce Chemical Company.

Preferably, an antigen may be linked to the Chikungunya virus structural protein or Venezuelan equine encephalitis virus structural protein as a fusion protein produced by way of genetic engineering.

A Chikungunya virus structural protein or Venezuelan equine encephalitis virus structural protein used in the present invention may be a Chikungunya or Venezuelan equine encephalitis virus envelope protein or a capsid or a complex of one or more envelope proteins and/or a capsid protein.

Examples of Chikungunya virus include, but are not limited to, strains of 37997 and LR2006 OPY-1. Examples of Venezuelan equine encephalitis virus include, but are not limited to, TC-83.

Chikungunya virus structural protein or Venezuelan equine encephalitis virus structural protein used in the present invention may naturally occurring virus structural protein or modified protein thereof. The modified protein may be a fragment of the naturally occurring virus structural protein. In one embodiment, the modified protein has at least 70%, 75%, 80%, 85%, 90%, 95% or 98% amino acid sequence identity to a naturally occurring viral capsid and/or envelope protein. In one embodiment, the modified protein is a mutant where at most 10% of the amino acids are deleted, substituted, and/or added based on a naturally occurring viral capsid and/or envelope protein. For example, K64A or K64N mutation may be introduced into a capsid of Venezuelan equine encephalitis virus structural protein used in the present invention.

Chikungunya or Venezuelan equine encephalitis virus structural protein may consist of or comprise a capsid, E2 and E1.

Examples of Chikungunya virus structural protein include, but are not limited to, Capsid-E2-E1 of Chikungunya virus Strain 37997, and Capsid-E2-E1 of Chikungunya virus LR2006 OPY-1.

Examples of Venezuelan equine encephalitis virus structural protein include, but are not limited to, Capsid-E2-E1 of Venezuelan equine encephalitis virus Strain TC-83.

An exemplary Chikungunya virus structural protein sequence is provided at Genbank Accession No. ABX40006.1, which is described below (SEQ ID NO: 1):

mefiptqtfynrryqprwtprptiqvirprprpqrqagqlaqlisavnkl tmravpqqkprrnrknkkqkqkqqapqnntnqkkqppkkkpaqkkkkpgr rermcmkiendcifevkhegkvtgyaclvgdknmkpahvkgtidnadlak lafkrsskydlecaqipvhmksdaskfthekpegyynwhhgavqysggrf tiptgagkpgdsgrpifdnkgrvvaivlgganegartalsvvtwnkdivt kitpegaeewslaipvmcllanttfpcsqppctpccyekepeetlrmled nvmrpgyyqllqasltcsphrqrrstkdnfnvykatrpylahcpdcgegh schspvalerirneatdgtlkiqvslqigiktddshdwtklrymdnhmpa daeraglfvrtsapctitgtmghfilarcpkgetltvgftdsrkishsct hpfhhdppvigrekfhsrpqhgkelpcstyvqstaatteeievhmppdtp pdrtlmsqqsgnvkitvngqtvrykcncggsnegltttdkvinnckvdqc haavtnhkkwqynsplvprnaelgdrkgkihipfplanvtcrvpkarnpt vtygknqvimllypdhptllsyrnmgeepnyqeewvmhkkevvltvpteg levtwgnnepykywpqlstngtahghpheiilyyyelyptmtvvvvsvat fillsmvgmaagmcmcarrrcitpyeltpgatvpfllsliccirtakaat yqeaaiylwneqqplfwlqaliplaalivlcnclrllpccktlaflavm

```
svgahtvsayehvtvipntvgvpyktlvnrpgyspmvlemellsvtlept lsldyitceyktvipspyvkccgtaeckdknlpdysckvftgvypfmwgg aycfcdaentqlseahveksescktefasayrahtasasaklrvlyqgnn itvtayangdhavtvkdakfivgpmssawtpfdnkivvykgdvynmdypp fgagrpgqfgdiqsrtpeskdvyantqlvlqrpavgtvhvpysqapsgfk ywlkergaslqhtapfgcqiatnpvravncavgnmpisidipeaaftrvv dapsltdmscevpacthssdfggvaiikyaaskkgkcavhsmtnavtire aeievegnsqlqisfstalasaefrvqvcstqvhcaaechppkdihivny pashttlgvqdisatamswvqkitggvglvvavaalilivvlcvsfsrh
```

Another exemplary Chikungunya virus structural protein sequence is provided at Genbank Accession No. ABX40011.1, which is described below (SEQ ID NO: 2):

```
mefiptqtfynrryqprwaprptiqvirprprpqrqagqlaqlisavnkl tmravpqqkprrnrknkkqrqkqaapqnntnqkkqppkkkpaqkkkkpgr rermcmkiendcifevkhegkvtgyaclvgdknmkpahvkgtidnadlak lafkrsskydlecaqipvhmksdaskfthekpegyynwhhgavqysggrf tiptgagkpgdsgrpifdnkgrvvaivlgganegartalsvvtwnkdivt kitpegaeewslaipvmcllanttfpcsqppctpccyekepeetlrmled nvmrpgyyqllqasltcsphrqrrstkdnfnvykatrpylahcpdcgegh schspvalerirrneatdgtlkiqvslqigiktddshdwtklrymdnhmpa daeraglfvrtsapctitgtmghfilarcpkgetltvgftdsrkishsct hpfhhdppvigrekfhsrpqhgkelpcstyvqstaatteeievhmppdtp pdrtlmsqqsgnvkitvngqtvrykcncggsnegltttdkvinnckvdqc haavtnhkkwqynsplvprnaelgdrkgkihipfplanvtcrvpkarnpt vtygknqvimllypdhptllsyrnmgeepnyqeewvmhkkevvltvpteg levtwgnnepykywpqlstngtahghpheiilyyyelyptmtvvvvsvat fillsmvgmaagmcmcarrrcitpyeltpgatvpfllslicccirtakaat yqeaaiylwneqqplfwlqaliplaalivlcnclrllpccckctlaflavm svgahtvsayehvtvipntvgvpyktlvnrpgyspmvlemellsvtlept lsldyitceyktvipspyvkccgtaeckdknlpdysckvftgvypfmwgg aycfcdaentqlseahveksescktefasayrahtasasaklrvlyqgnn itvtayangdhavtvkdakfivgpmssawtpfdnkivvykgdvynmdypp fgagrpgqfgdiqsrtpeskdvyantqlvlqrpavgtvhvpysqapsgfk ywlkergaslqhtapfgcqiatnpvravncavgnmpisidipeaaftrvv dapsltdmscevpacthssdfggvaiikyaaskkgkcavhsmtnavtire aeievegnsqlqisfstalasaefrvqvcstqvhcaaechppkdihivny pashttlgvqdisatamswvqkitggvglvvavaalilivvlcvsfsrh
```

An exemplary Venezuelan equine encephalitis virus structural protein is described below (SEQ ID NO: 3):

```
mfpfqpmypmqpmpyrnpfaaprrpwfprtdpflamqveqeltrsmanlt fkqrrdappegpsaakpkkeasqkqkgggqgkkknqgkkkaktgppnpka qngnkkktnkkpgkrqrmvmkledsktfpimlegkingyacvvggklfrp mhvegkidndvlaalktkkaskydleyadvpqnmradtfkythekpqgyy swhhgavqyengrftvpkgvgakgdsgrpildnqgrvvaivlggvnegsr talsvvmwnekgvtvkytpenceqwslvttmsllanvtfpcaqppicydr kpaetlamlsvnvdnpgydelleaavkcpgrkrrsteelfneykltrpym arcircavgschspiaieavksdghdgyvrlqtssqygldssgnlkgrtm rydmhgtikeiplhqvslytsrpchivdghgyfllarcpagdsitmefkk dsvrhscsvpyevkfnpvgrelythppehgveqscqvyahdaqnragyve mhlpgsevdsslvslsgssvtvtppdgtsalvececggtkisetinktkq fsqctkkeqcrayrlqndkwvynsdklpkaagatlkgklhvpflladgkc tvplapepmitfgfrsvslklhpknptylitrqladephythelisepav rnftvtekgwefvwgnhppkrfwaqetapgnphglphevithyyhrypms tilglsicaaiatvsvaastwlfcrsrvacltpyrltpnaripfclavlc cartaraettwesldhlwnnnqqmfwiqlliplaalivvtrllrcvccvv pflmagaagagayehattmpsqagisyntivnragyaplpisitptkikl iptvnleyvtchyktgmdspaikccgsqectptyrpdeqckvftgvpyfm wggaycfcdtentqvskayvmksddcladhaeaykahtasvqaflnitvg ehsivttvyvngetpvnfngvkitagplstawtpfdrkivqyaeiynydf peygagqpgafgdiqsrtvsssdlyantnlvlqrpkagaihvpytqapsg feqwkkdkapslkftapfgceiytnpiraencavgsiplafdipdalftr vsetptlsaaectlnecvyssdfggiatvkysasksgkcavhvpsgtatl keaavelteqgsatihfstanihpefrlqictsyvtckgdchppkdhivt hpqyhaqtftaavsktawtwltsllggsaviiiiglvlativamyvltnq khn
```

In one embodiment, a first attachment site comprises an amino group, preferably an amino group of a lysine residue. In one embodiment, the second attachment site comprises sulfhydryl group, preferably, a sulfhydryl group of a cysteine.

According to the present invention, a Chikungunya virus like particle or Venezuelan equine encephalitis virus like particle comprising a Chikungunya or Venezuelan equine encephalitis virus structural protein and an antigen selected from the group consisting of an antigen derived from PD-1 and an antigen derived from a ligand of PD-1 (e.g. PD-L1, PD-L2), wherein the Chikungunya virus structural protein or Venezuelan equine encephalitis virus structural protein and the antigen are expressed as a fusion protein can be provided.

An antigen selected from the group consisting of an antigen derived from PD-1 and an antigen derived from a ligand of PD-1 (e.g. PD-L1, PD-L2) can be fused with any site of the Chikungunya virus structural protein or Venezuelan equine encephalitis virus structural protein. For example, an antigen selected from the group consisting of an antigen derived from PD-1 and an antigen derived from a ligand of PD-1 (e.g. PD-L1, PD-L2) may be directly or indirectly linked to N- or C-terminal of a Chikungunya virus structural protein or Venezuelan equine encephalitis virus structural protein, or an antigen selected from the group consisting of an antigen derived from PD-1 and an antigen derived from a ligand of PD-1 (e.g. PD-L1, PD-L2) may be inserted into Chikungunya virus structural protein or Venezuelan equine encephalitis virus structural protein.

In one embodiment, at least one antigen selected from the group consisting of an antigen derived from PD-1 and an antigen derived from a ligand of PD-1 (e.g. PD-L1, PD-L2) is inserted into E2 of Chikungunya virus structural protein or Venezuelan equine encephalitis virus structural protein. For example, regarding Chikungunya virus structural protein, at least one antigen selected from the group consisting of an antigen derived from PD-1 and an antigen derived from a ligand of PD-1 (e.g. PD-L1, PD-L2) is inserted between residues 519 and 520 of SEQ ID NOs: 1 or 2 (i.e. between G at 519-position and Q at 520-position of SEQ ID NOs: 1 or 2); between residues 530 and 531 of SEQ ID NOs: 1 or 2 (i.e. between G at 530-position and S at 531-position of SEQ ID NOs: 1 or 2); between residues 531 and 532 of SEQ ID NOs: 1 or 2 (i.e. between S at 531-position and N at 532-position of SEQ ID NOs: 1 or 2); between residues 529 and 530 of SEQ ID NOs: 1 or 2 (i.e. between G at 529-position and G at 530-position of SEQ ID NOs: 1 or 2); or between residues 510 and 511 of SEQ ID NOs: 1 or 2 (i.e. between S at 510-position and G at 511-position of SEQ ID NOs: 1 or 2); or between residues 511 and 512 of SEQ ID NOs: 1 or 2 (i.e. between G at 511-position and N at 512-position of SEQ ID NOs: 1 or 2); or between residues 509 and 510 of SEQ ID NOs: 1 or 2 (i.e. between Q at 509-position and S at 510-position of SEQ ID NOs: 1 or 2). VLP_CHI 532 vector (SEQ ID NO: 25) may be used for preparing Chikungunya virus like particle where the antigen is inserted between residues 531 and 532 of SEQ ID NOs: 1 or 2.

For example, regarding Venezuelan equine encephalitis virus structural protein, at least one antigen selected from the group consisting of an antigen derived from PD-1 and an antigen derived from a ligand of PD-1 (e.g. PD-L1, PD-L2) is inserted between residues 517 and 518 of SEQ ID NO: 3 (i.e. between G at 517-position and S at 518-position of SEQ ID NO: 3); between residues 518 and 519 of SEQ ID NO: 3 (i.e. between S at 518-position and S at 519-position of SEQ ID NO: 3); between residues 519 and 520 of SEQ ID NO: 3 (i.e. between S at 519-position and V at 520-position of SEQ ID NO: 3); between residues 515 and 516 of SEQ ID NO: 3 (i.e. between L at 515-position and S at 516-position of SEQ ID NO: 3); between residues 516 and 517 of SEQ ID NO: 3 (i.e. between S at 516-position and G at 517-position of SEQ ID NO: 3); between residues 536 and 537 of SEQ ID NO: 3 (i.e. between C at 536-position and G at 537-position of SEQ ID NO: 3); between residues 537 and 538 of SEQ ID NO: 3 (i.e. between G at 537-position and G at 538-position of SEQ ID NO: 3); between residues 538 and 539 of SEQ ID NO: 3 (i.e. between G at 538-position and T at 539-position of SEQ ID NO: 3). VLP_VEEV VLP 518 vector (SEQ ID NO:26) may be used for preparing Venezuelan equine encephalitis virus like particle where the antigen is inserted between residues 517 and 518 of SEQ ID NO: 3.

The fusion protein may be expressed using a conventional technique in the art. A variety of expression systems can be used for the expression of the fusion protein. For example, the fusion protein can be expressed in 293 cells, Sf9 cells or E. coli.

A protein derived from Chikungunya virus (CHIKV) or Venezuelan equine encephalitis virus (VEEV) may be a naturally occurring viral protein or modified protein thereof.

When a protein derived from a virus is conjugated with a protein derived from an antigen, a linker peptide including SG, GS, SGG, GGS SGSG and TRGGS may be used.

Examples of conjugation of the protein derived from a virus (referred to as "PFV" below) with the protein derived from the antigen (referred to as "PFA" below) include, but not limited to: PFV-SG-PFA-GS-PFV; PFV-SG-PFA-GGS-PFV; PFV-SSG-PFA-GS-PFV; PFV-SGG-PFA-GGS-PFV; PFV-SGSG-PFA-GS-PFV; and PFA-SGG-PFA-TRGGS-PFV.

In one embodiment, the present invention provides a virus like particle comprising a fusion protein of a protein derived from Chikungunya virus (CHIKV) or Venezuelan equine encephalitis virus (VEEV) and a protein derived from PD-1 or PD-L1, wherein the virus like particle is prepared by transfecting an expression vector comprising a nucleic acid molecule comprising a nucleotide sequence represented by SEQ ID NOs: 27-32 into a mammalian cell (e.g. 293F cell). Regarding this embodiment, modified fusion protein can be also used for a virus like particle provided by the present invention, which can be prepared by transfecting an expression vector comprising a nucleic acid molecule comprising a nucleotide sequence having at least 70%, 75%, 80%, 85%, 90%, 95% or 98% nucleotide sequence identity to SEQ ID NOs: 27-32 into a mammalian cell (e.g. 293F cell).

In one embodiment, the present invention provides a virus like particle comprising or consisting of:
one or more capsid of Chikungunya virus (CHIKV) or Venezuelan equine encephalitis virus (VEEV);
one or more E1 of Chikungunya virus (CHIKV) or Venezuelan equine encephalitis virus (VEEV); and
one or more E2 of Chikungunya virus (CHIKV) or Venezuelan equine encephalitis virus (VEEV), wherein an antigen selected from the group consisting of an antigen derived from PD-1 and an antigen derived from a ligand of PD-1 (e.g. PD-L1, PD-L2) is inserted into E2 of Chikungunya virus (CHIKV) or Venezuelan equine encephalitis virus (VEEV). For example, present invention provides a virus like particle comprising or consisting of:
240 capsids of Chikungunya virus (CHIKV) or Venezuelan equine encephalitis virus (VEEV);
240 E1s of Chikungunya virus (CHIKV) or Venezuelan equine encephalitis virus (VEEV); and
240 E2s of Chikungunya virus (CHIKV) or Venezuelan equine encephalitis virus (VEEV), wherein an antigen selected from the group consisting of an antigen derived from PD-1 and an antigen derived from a ligand of PD-1 (e.g. PD-L1, PD-L2) is inserted into each of E2s of Chikungunya virus (CHIKV) or Venezuelan equine encephalitis virus (VEEV).

In this embodiment, the E2 into which the antigen is inserted may consist of an amino acid sequence represented by SEQ ID NOs: 33-36; the E1 may consist of an amino acid sequence represented by SEQ ID NO: 37; and the capsid may consist of an amino acid sequence represented by SEQ ID NO: 38; or
the E2 into which the antigen is inserted may consist of an amino acid sequence represented by SEQ ID NOs: 39-42; the E1 may consist of an amino acid sequence represented by SEQ ID NO: 43; and the capsid may consist of an amino acid sequence represented by SEQ ID NO: 44.

Further, regarding this embodiment, modified capsid of Chikungunya virus (CHIKV) or Venezuelan equine encephalitis virus (VEEV), modified E1 of Chikungunya virus (CHIKV) or Venezuelan equine encephalitis virus (VEEV) and modified E2 of Chikungunya virus (CHIKV) or Venezuelan equine encephalitis virus (VEEV) may be used for the virus like particle. For example, the modified capsid of Chikungunya virus (CHIKV) or Venezuelan equine encephalitis virus (VEEV) may have at least 70%, 75%, 80%, 85%, 90%, 95% or 98% amino acid sequence identity to the amino acid sequence represented by SEQ ID NO: 38 or SEQ ID NO: 44; the modified E1 of Chikungunya virus (CHIKV) or Venezuelan equine encephalitis virus (VEEV) may have at least 70%, 75%, 80%, 85%, 90%, 95% or 98% amino acid sequence identity to the amino acid sequence represented by SEQ ID NO: 37 or SEQ ID NO: 43; and/or the modified E2 of Chikungunya virus (CHIKV) or Venezuelan equine encephalitis virus (VEEV) may have at least 70%, 75%, 80%, 85%, 90%, 95% or 98% amino acid sequence identity to the amino acid sequence represented by SEQ ID NOs: 33-36 or SEQ ID NOs: 39-42. Also, the modified capsid, E1 or E2 may be a mutant where at most 10% of the amino acids are deleted, substituted, and/or added based on the capsid consisting of an amino acid sequence represented by SEQ ID NO: 38 or SEQ ID NO: 44; E1 consisting of an amino acid sequence represented by SEQ ID NO: 37 or SEQ ID NO: 43; and/or E2 consisting of an amino acid sequence represented by SEQ ID NOs: 33-36 or SEQ ID NOs: 39-42.

Virus like particle may be prepared by introducing an expression vector comprising a DNA molecule having a nucleotide sequence encoding the virus like particle into a cell (e.g. 293 cell) and recovering the virus like particle from the conditioned medium using ultracentrifugal method.

(2) Nucleotide, Vector, Host Cell

In a second aspect, the present invention provides a nucleic acid molecule comprising a nucleotide sequence for expressing the disclosed particle which comprises a virus structural protein and an antigen selected from the group consisting of an antigen derived from PD-1 and an antigen derived from a ligand of PD-1.

The nucleic acid molecule provided by the present invention may be an isolated nucleic acid molecule for expressing a Chikungunya virus like particle or Venezuelan equine encephalitis virus like particle which comprises a virus structural protein and an antigen selected from the group consisting of an antigen derived from PD-1 and an antigen derived from a ligand of PD-1.

One skilled in the art may prepare the nucleic acid molecule provided by the present invention described above based on an exemplary nucleotide sequences that encode capsid and/or envelope represented by SEQ ID NOs: 63-64.

For example, one skilled in the art may introduce a nucleotide sequence encoding an antigen derived from PD-1 or PD-L1 into nucleotide sequence encoding E2 of Chikungunya or Venezuelan equine virus structural protein for preparing a nucleic acid molecule which is introduced into a vector to express Chikungunya virus like particle or Venezuelan equine virus like particle which comprises a virus structural protein and an antigen selected from the group consisting of an antigen derived from PD-1 and an antigen derived from a ligand of PD-1. Examples of the nucleotide sequence where antigen-derived sequence is introduced into E2 as described above include, but are not limited to, nucleotide sequence represented by SEQ ID NOs: 27 or 29 (for expressing Chikungunya virus like particle comprising PD-1 antigen); nucleotide sequence represented by SEQ ID NO: 31 (for expressing Chikungunya virus like particle comprising PD-L1 antigen); nucleotide sequence represented by SEQ ID NOs: 28 or 30 (for expressing Venezuelan equine encephalitis virus like particle comprising PD-1 antigen); and nucleotide sequence represented by SEQ ID NO: 32 (for expressing Venezuelan equine encephalitis virus like particle comprising PD-L1 antigen).

In one embodiment, the present invention provides a vector comprising the nucleic acid molecule as described above, wherein the vector optionally comprises an expression control sequence operably linked to the nucleic acid molecule.

Examples of an expression control sequence include, but are not limited to, promoter such as CMV promoter, phage lambda PL promoter, the E. coli lac, phoA and tac promoters, the SV40 early and late promoters, and promoters of retroviral LTRs.

In this embodiment, the vector comprising an expression control sequence operably linked to the nucleic acid molecule as described above can be used as an expression vector for preparing the particle provided by the present invention.

The expression vectors can be prepared by a person skilled in the art based on WO/2012/006180, the entire contents of which are incorporated by reference herein.

Examples of vectors which can be used for expressing a virus like particle comprising a fusion protein of a protein derived from Chikungunya virus (CHIKV) and an antigen derived from PD-1 include a vector shown in VLP31.11 vector (SEQ ID NO: 45) and VLP274.11 vector (SEQ ID NO: 46).

Examples of vectors which can be used for expressing a virus like particle comprising a fusion protein of a protein derived from Chikungunya virus (CHIKV) and an antigen derived from PD-L1 include a vector shown in VLP299.15 vector (SEQ ID NO: 47).

Examples of vectors which can be used for expressing a virus like particle comprising a fusion protein of a protein derived from Venezuelan equine encephalitis virus (VEEV) and an antigen derived from PD-1 include a vector shown in VLP31.21 vector (SEQ ID NO: 48) and VLP274.21 vector (SEQ ID NO: 49).

Examples of vectors which can be used for expressing a virus like particle comprising a fusion protein of a protein derived from Venezuelan equine encephalitis virus (VEEV) and an antigen derived from PD-L1 include a vector shown in VLP299.25 vector (SEQ ID NO: 50).

A nucleic acid molecule having at least 70%, 75%, 80%, 85%, 90%, 95% or 98% nucleotide sequence identity to the nucleic acid molecule having a nucleotide sequence represented by any one of SEQ ID NOs: 45-50 and a nucleic acid molecule which may be a mutant where at most 10% of the nucleotides are deleted, substituted, and/or added based on the nucleic acid molecule having a nucleotide sequence represented by any one of SEQ ID NOs: 45-50 are also provided by the present invention.

In addition, a recombinant cell prepared by introducing the above-described vector into a host cell is provided by the present invention. For example, CHO cells or 293 cells are used as host cells.

(3) Pharmaceutical Composition, Kit

In a third aspect, the present invention provides a pharmaceutical composition and a kit comprising a pharmaceutical composition, wherein the pharmaceutical composition comprises a particle comprising a virus structural protein and an antigen selected from the group consisting of an antigen derived from PD-1 and an antigen derived from a ligand of PD-1; or a nucleic acid molecule comprising a nucleotide sequence for expressing a particle which comprises a virus structural protein and an antigen selected from the group consisting of an antigen derived from PD-1 and an antigen derived from a ligand of PD-1; and a pharmaceutically acceptable carrier.

In one embodiment, the present invention provides a pharmaceutical composition or a kit comprising a pharmaceutical composition, wherein the pharmaceutical composition comprises the Alphavirus or Flavivirus virus like particle (e.g. Chikungunya virus like particle or Venezuelan equine encephalitis virus like particle) as described above or the nucleic acid molecule as described above; and a pharmaceutically acceptable carrier. The content of the Alphavirus or Flavivirus virus like particle and the content of the nucleic acid molecule may be 0.00001-1 w/w % of the pharmaceutical composition.

Dosage amount of the particle provided by the present invention (e.g. CHIKV VLP or VEEV VLP) may be 1-500 µg/day.

One or more PD-1 antigens or PD-1 ligand antigens may be used for one pharmaceutical composition provided by the present invention.

The pharmaceutical composition may further comprise adjuvant. Examples of adjuvant include, but are not limited to, Ribi solution (Sigma Adjuvant system, Sigma-Aldrich). The pharmaceutical composition provided by the present invention may contain buffering agent such as dibasic sodium phosphate hydrate, sodium dihydrogen phosphate and sodium chloride; and preserving agent such as thimerosal. In one embodiment, the pharmaceutical composition is an aqueous solution containing 0.001-1 w/w % of a particle (e.g. CHIKV VLP or VEEV VLP) comprising a virus structural protein and an antigen selected from the group consisting of an antigen derived from PD-1 or an antigen derived from a ligand of PD-1, 1-10 w/w % of buffering agent, 0.01-1 w/w % of adjuvant and 0.00001-0.001 w/w % of preserving agent.

A skilled person can prepare the pharmaceutical composition using conventional technique. For example, a particle (e.g. CHIKV VLP or VEEV VLP) comprising a virus structural protein and an antigen selected from the group consisting of an antigen derived from PD-1 or an antigen derived from a ligand of PD-1 is mixed with buffer solution having physiological pH (e.g. pH 5-9, pH7) to prepare the pharmaceutical composition provided by the present invention.

In one embodiment, the pharmaceutical composition is a vaccine or an immunostimulant comprising a particle comprising a virus structural protein and an antigen selected from the group consisting of an antigen derived from PD-1 and an antigen derived from a ligand of PD-1. For example, the vaccine composition provided by the present invention can be used for immunotherapy (e.g. treating cancer).

In one embodiment, the pharmaceutical composition is a DNA vaccine comprising a nucleic acid molecule comprising a nucleotide sequence for expressing a particle which comprises a virus structural protein and an antigen selected from the group consisting of an antigen derived from PD-1 and an antigen derived from a ligand of PD-1. In one embodiment, the DNA vaccine provided by the present invention comprises CpG containing oligonucleotide.

The pharmaceutical composition provided in the third aspect of the present invention can be administered one or more times. When the pharmaceutical composition provided in the third aspect of the present invention is administered more than one time, different particle provided in the first aspect of the present invention (e.g. CHIKV VLP or VEEV VLP) may be used for each of the administration. In one embodiment, combination of immunization using CHIKV VLP provided in the first aspect of the invention and immunization using VEEV VLP provided in the first aspect of the invention is employed. For example, CHIKV VLP provided in the first aspect of the present invention may be used for the 1st immunization and VEEV VLP provided in the first aspect of the present invention may be used for the 2nd immunization, or VEEV VLP provided in the first aspect of the present invention may be used for the 1st immunization and CHIKV VLP provided in the first aspect of the present invention may be used for the 2nd immunization.

A skilled person can determine timing of immunization using the composition or vaccine provided by the present invention. For example, 2nd immunization is performed 1, 2, 3, 4, 5, 6, 7, 8, 9 or 10 weeks after 1st immunization.

In one embodiment, the present invention provides a kit comprising
(a) a pharmaceutical composition comprising the particle provided in the first aspect of the present invention; and
(b) another pharmaceutical composition comprising the particle provided in the first aspect of the present invention, wherein the particle contained in (a) is a virus like particle which is different from the particle contained in (b). In this embodiment, the particle contained in (a) may be Chikungunya virus like particle and the particle contained in (b) may be Venezuelan equine encephalitis virus like particle.

In one embodiment, the present invention provides a kit comprising
(a) a pharmaceutical composition comprising the particle provided in the first aspect of the present invention; and
(b) another pharmaceutical composition comprising the particle provided in the first aspect of the present invention,
(c) one or more pharmaceutical composition, each of which comprises the particle provided in the first aspect of the present invention,
wherein (a) is used for priming immunization and (b) and (c) are used for boosting immunization; and the particle contained in (a) is a virus like particle which is different from the particle contained in (b); and the particle contained in (c) is different from the particle contained in (a) and (b), or the same as the particle contained in (a) or (b).

The respective pharmaceutical compositions contained in the above-described kit may be administered simultaneously, separately or sequentially.

The Alphavirus or Flavivirus virus like particle (e.g. Chikungunya virus or Venezuelan equine encephalitis virus) provided in the first aspect of the present invention or the nucleic acid molecule provided by the second aspect of the invention can be used for the pharmaceutical composition provided in the third aspect of the present invention.

For example, Chikungunya or Venezuelan equine encephalitis virus like particle comprising or consisting of: one or more (e.g. 240) capsid of Chikungunya virus (CHIKV) or Venezuelan equine encephalitis virus (VEEV); one or more (e.g. 240) E1 of Chikungunya virus (CHIKV) or Venezuelan equine encephalitis virus (VEEV); and one or more (e.g. 240) E2 of Chikungunya virus (CHIKV) or Venezuelan equine encephalitis virus (VEEV), wherein PD-1 antigen is inserted into E2 of Chikungunya virus (CHIKV) or Venezuelan equine encephalitis virus (VEEV) may be used for preparing the composition or vaccine provided in the third aspect of the present invention. The E2 into which the antigen is inserted may consist of an amino acid sequence represented by SEQ ID NOs: 33-36; the E1 may consist of an amino acid sequence represented by SEQ ID NO: 37; and the capsid may consist of an amino acid sequence represented by SEQ ID NO: 38; or
the E2 into which the antigen is inserted may consist of an amino acid sequence represented by SEQ ID NOs: 39-42; the E1 may consist of an amino acid sequence represented by SEQ ID NO: 43; and the capsid may consist of an amino acid sequence represented by SEQ ID NO: 44.

(4) Use of the Disclosed Particle Etc.

In a forth aspect, the present invention provides a use of a particle comprising a virus structural protein and an antigen selected from the group consisting of an antigen derived from PD-1 and an antigen derived from a ligand of PD-1; or a nucleic acid molecule comprising a nucleotide sequence for expressing a particle which comprises a virus structural protein and an antigen selected from the group consisting of an antigen derived from PD-1 and an antigen derived from a ligand of PD-1 for the manufacture of a pharmaceutical composition or a kit for treating or preventing cancer or infectious disease; producing an antibody against PD-1 or a ligand of PD-1 in a mammal (e.g. human); modulating an immune response; immunostimulation; inhibiting an interaction between PD-1 and a ligand of PD-1; or inhibiting a PD-1 activity. A method of treating or preventing cancer or infectious disease; producing an antibody against PD-1 or a ligand of PD-1 in a mammal (e.g. human); modulating an immune response; immunostimulation; inhibiting an interaction between PD-1 and a ligand of PD-1; or inhibiting a PD-1 activity comprising administering an effective amount of the particle or the pharmaceutical composition disclosed herein to a subject in need thereof is also provided.

The pharmaceutical composition may be administered to a mammal (e.g. human) intramuscularly (i.m.), intracutaneously (i.c.), subcutaneously (s.c.), intradermally (i.d.) or intraperitoneally (i.p.).

In one embodiment, the pharmaceutical composition is a vaccine, which can be applied to immunotherapy (e.g. treating cancer).

Examples of the cancer which may be treated include, but are not limited to, melanoma, renal cancer, prostate cancer, breast cancer, colon cancer and non-small cell lung cancer. Other examples of the cancer include, but are not limited to, include bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and combinations thereof.

Examples of infectious disease which may be treated include, but are not limited to, HIV, Influenza, Herpes, Güardia, Malaria, *Leishmania*, the pathogenic infection by the virus Hepatitis (A, B and C), herpes virus (e.g., VZV, HSV-I, HAV-6, HSV-II, and CMV, Epstein Barr virus), adenovirus, influenza virus, flaviviruses, echovirus, rhinovirus, coxsackie virus, cornovirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus and arboviral encephalitis virus, pathogenic infection by the bacteria chlamydia, rickettsial bacteria, mycobacteria, staphylococci, streptococci, pneumonococci, meningococci and conococci, *klebsiella, proteus, serratia, pseudomonas, legionella, diphtheria, salmonella, bacilli*, cholera, tetanus, botulism, anthrax, plague, leptospirosis, and Lymes disease bacteria, pathogenic infection by the fungi *Candida* (*albicans, krusei, glabrata, tropicalis*, etc.), *Cryptococcus neoformans, Aspergillus* (*fumigatus, niger*, etc.), Genus *Mucorales* (*mucor, absidia, rhizophus*), *Sporothrix schenkii, Blastomyces dermatitidis, Paracoccidioides brasiliensis, Coccidioides immitis* and *Histoplasma capsulatum*, and pathogenic infection by the parasites *Entamoeba histolytica, Balantidium coli, Naegleriafowleri, Acanthamoeba* sp., *Giardia lambia, Cryptosporidium* sp., *Pneumocystis carinii, Plasmodium vivax, Babesia microti, Trypanosoma brucei, Trypanosoma cruzi, Leishmania donovani, Toxoplasma gondi*, and *Nippostrongylus brasiliensis*.

When a pharmaceutical composition comprising a virus structural protein and an antigen selected from the group consisting of an antigen derived from PD-1 or a ligand of PD-1 is administered to a mammal (e.g. human), an antibody against PD-1 or a ligand of PD-1 is produced in blood of the mammal. The produced antibody may modulate an immune response; show immunostimulating effects; inhibit an interaction between PD-1 and a ligand of PD-1 (e.g. PD-L1, PD-L2); or inhibit a PD-1 activity.

The produced antibody may be humanized using a conventional technique. Using the particle provided in a first aspect of the present invention, monoclonal antibody or polyclonal antibody can be prepared. In one embodiment, the present invention provides a method for producing an antibody against PD-1 or a ligand of PD-1 comprising administering the particle provided in a first aspect of the present invention to a non-human mammal and humanizing non-human mammal produced antibody.

As used herein, the term "antibody" refers to molecules which are capable of binding an epitope or antigenic determinant. The term is meant to include whole antibodies and antigen-binding fragments thereof, including single-chain antibodies. Such antibodies include human antigen binding antibody fragments and include, but are not limited to, Fab, Fab' and F(ab')2, Fd, single-chain Fvs (scFv), single-chain antibodies, disulfide-linked Fvs (sdFv) and fragments comprising either a VL or VH domain. The antibodies can be from any animal origin including birds and mammals. Preferably, the antibodies are mammalian e.g. human, murine, rabbit, goat, guinea pig, camel, horse and the like, or other suitable animals e.g. chicken. As used herein, "human" antibodies include antibodies having the amino acid sequence of a human immunoglobulin and include antibodies isolated from human immunoglobulin libraries or from animals transgenic for one or more human immunoglobulins and that do not express endogenous immunoglobulins, as described, for example, in U.S. Pat. No. 5,939,598, the disclosure of which is incorporated herein by reference in its entirety.

The term "PD-1 activity" refers to one or more immunoregulatory activities associated with PD-1. For example, PD-1 is a negative regulator of the TcR/CD28-mediated immune response. Thus, examples of modulation of immune response include, but are not limited to, enhancing the TcR/CD28-mediated immune response.

In one embodiment, the present invention provides a method for producing Chikungunya or Venezuelan equine encephalitis virus like particle provided in a first aspect of the present invention, comprising preparing a vector designed for expression of the particle; culturing a cell which is transfected with the vector to express the particle; and recovering the particle. In this embodiment, transfection can be conducted using a conventional method. Cells using for the transfection may be 293 cells. Recovering VLP may include collecting a conditioned medium after cells are transfected with a vector, and may further include purify VLP from the conditioned medium using ultracentrifugation.

The following exemplary embodiments (1)-(35) are further provided by the present invention:

(1) A particle comprising a virus structural protein and at least one antigen selected from the group consisting of an antigen derived from PD-1 and an antigen derived from a ligand of PD-1;
(2) A particle, which is a derivative of the particle according to (1);
(3) The particle according to (1) or (2), wherein the antigen is an antigen derived from PD-1, PD-L1 or PD-L2;
(4) The particle according to any one of (1)-(3), wherein administration of the particle to animals induces an antibody against the antigen and the antibody blocks PD-1 and PD-L1 interaction or PD-1 and PD-L2 interaction;
(5) The particle according to any one of (1)-(4), wherein said particle is virus like particle;
(6) The particle according to any one of (1)-(5), wherein said particle is a virus like particle derived from alphavirus or flavivirus;
(7) The particle according to any one of (1)-(6), wherein said particle is a virus like particle derived from Chikungunya virus or Venezuelan equine encephalitis virus;
(8) The particle according to any one of (1)-(7), wherein the virus structural protein comprises at least one first attachment site and the at least one antigen comprises at least one second attachment site, and wherein the virus structural protein and the antigen are linked through the at least one first and the at least one second attachment site, and wherein the particle is virus like particle;
(9) The particle according to any one of (1)-(8), wherein the virus structural protein comprises the capsid and/or the envelope proteins E1 and E2;
(10) The particle according to (9), wherein at least one antigen derived from PD-1 or at least one antigen derived from PD-L1 is inserted into E2 of the envelope protein;
(11) The particle according to any one of (1)-(10), wherein the virus structural protein is a protein derived from Chikungunya virus (CHIKV) or Venezuelan equine encephalitis virus (VEEV);

(12) The particle according to any one of (1)-(11), wherein the particle is Chikungunya virus like particle consisting of one or more envelope protein E2 into which the antigen derived from PD-1 is inserted, one or more envelope protein E1 and one or more capsid, and wherein the envelope protein E2 into which the antigen derived from PD-1 is inserted consists of an amino acid sequence represented by SEQ ID NOs: 33-35; the envelope protein E1 consists of an amino acid sequence represented by SEQ ID NO: 37; and the capsid consists of an amino acid sequence represented by SEQ ID NO: 38;

(13) The particle according to any one of (1)-(11), wherein the particle is Venezuelan equine virus like particle consisting of one or more envelope protein E2 into which the antigen derived from PD-1 is inserted, one or more envelope protein E1 and one or more capsid, and wherein the envelope protein E2 into which the antigen derived from PD-1 is inserted consists of an amino acid sequence represented by SEQ ID NOs: 39-41; the envelope protein E1 consists of an amino acid sequence represented by SEQ ID NO: 43; and the capsid consists of an amino acid sequence represented by SEQ ID NO: 44;

(14) The particle according to any one of (1)-(11), wherein the particle is Chikungunya virus like particle consisting of one or more envelope protein E2 into which the antigen derived from PD-L1 is inserted, one or more envelope protein E1 and one or more capsid, and wherein the envelope protein E2 into which the antigen derived from PD-L1 is inserted consists of an amino acid sequence represented by SEQ ID NO: 36; the envelope protein E1 consists of an amino acid sequence represented by SEQ ID NO: 37; and the capsid consists of an amino acid sequence represented by SEQ ID NO: 38;

(15) The particle according to any one of (1)-(11), wherein the particle is Venezuelan equine virus like particle consisting of one or more envelope protein E2 into which the antigen derived from PD-L1 is inserted, one or more envelope protein E1 and one or more capsid, and wherein the envelope protein E2 into which the antigen derived from PD-L1 is inserted consists of an amino acid sequence represented by SEQ ID NO: 42; the envelope protein E1 consists of an amino acid sequence represented by SEQ ID NO: 43; and the capsid consists of an amino acid sequence represented by SEQ ID NO: 44;

(16) A particle consisting of an amino acid sequence which has a sequence identity of 90% or more (or 95% or more) with an amino acid sequence of the particle according to any one of (1)-(15).

(17) An isolated nucleic acid molecule comprising a nucleotide sequence for expressing the particle according to any one of (1)-(16);

(18) An isolated nucleic acid molecule consisting of a nucleotide sequence which has a sequence identity of 90% or more with a nucleotide sequence represented by any one of SEQ ID NOs: 27-32;

(19) The nucleic acid molecule according to (18), wherein the nucleic acid molecule consists of a nucleotide sequence represented by any one of SEQ ID NOs: 27-32;

(20) A vector comprising the nucleic acid molecule according to any one of (17)-(19), wherein the vector optionally comprises an expression control sequence operably linked to the nucleic acid molecule (e.g. a vector consisting of a nucleotide sequence represented by SEQ ID NOs: 45, 46, 47, 48, 49 or 50);

(21) A pharmaceutical composition comprising:

(a) the particle according to any one of (1)-(16), the nucleic acid molecule according to any one of (17)-(19) and/or the vector according to (20); and (b) a pharmaceutically acceptable carrier;

(22) The pharmaceutical composition (e.g. vaccine) according to (21), wherein the pharmaceutical composition comprises the particle according to any one of (1)-(16) and a pharmaceutically acceptable carrier,

(23) Use of the particle according to any one of (1)-(16), the nucleic acid molecule according to any one of (17)-(19) and/or the vector according to (20) for the manufacture of a pharmaceutical composition or a kit for treating or preventing cancer or infectious disease; producing an antibody against PD-1 or a ligand of PD-1 in a mammal; modulating an immune response; immunostimulation; inhibiting an interaction between PD-1 and a ligand of PD-1; or inhibiting a PD-1 activity;

(24) The use according to (23), wherein the pharmaceutical composition is administered to inhibit binding of PD-L1 and/or PD-L2 to PD-1;

(25) The use according to (23) or (24), wherein the cancer is melanoma, renal cancer, prostate cancer, breast cancer, colon cancer or non-small cell lung cancer;
(26) The use according to (23) or (24), wherein the cancer is selected from the group consisting of bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and combinations thereof;
(27) The use according to (23) or (24), wherein the infectious disease is selected from the group consisting of HIV, Influenza, Herpes, Güardia, Malaria, *Leishmania*, the pathogenic infection by the virus Hepatitis (A, B and C), herpes virus (e.g., VZV, HSV-I, HAV-6, HSV-II, and CMV, Epstein Barr virus), adenovirus, influenza virus, flaviviruses, echovirus, rhinovirus, coxsackie virus, cornovirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus and arboviral encephalitis virus, pathogenic infection by the bacteria chlamydia, rickettsial bacteria, mycobacteria, staphylococci, streptococci, pneumonococci, meningococci and conococci, *klebsiella, proteus, serratia, pseudomonas, legionella, diphtheria, salmonella, bacilli*, cholera, tetanus, botulism, anthrax, plague, leptospirosis, and Lymes disease bacteria, pathogenic infection by the fungi *Candida* (*albicans, krusei, glabrata, tropicalis*, etc.), *Cryptococcus neoformans, Aspergillus* (*fumigatus, niger*, etc.), Genus *Mucorales* (*mucor, absidia, rhizophus*), *Sporothrix schenkii, Blastomyces dermatitidis, Paracoccidioides brasiliensis, Coccidioides immitis* and *Histoplasma capsulatum*, and pathogenic infection by the parasites *Entamoeba histolytica, Balantidium coli, Naegleriafowleri, Acanthamoeba* sp., *Giardia lambia, Cryptosporidium* sp., *Pneumocystis carinii, Plasmodium vivax, Babesia microti, Trypanosoma brucei, Trypanosoma cruzi, Leishmania donovani, Toxoplasma gondi*, and *Nippostrongylus brasiliensis*;
(28) A kit comprising
(a) a pharmaceutical composition comprising the particle according to any one of (1)-(16); and
(b) another pharmaceutical composition comprising the particle according to any one of (1)-(16),
wherein the particle contained in (a) is a virus like particle which is different from the particle contained in (b);
(29) The kit according to (28), wherein the particle contained in (a) is Chikungunya virus like particle and the particle contained in (b) is Venezuelan equine encephalitis virus like particle, or the particle contained in (a) is Venezuelan equine encephalitis virus like particle and the particle contained in (b) is Chikungunya virus like particle;
(30) The kit according to (28) or (29), further comprising (c) one or more pharmaceutical compositions, each of which comprises the particle according to any one of (1)-(16), wherein (a) is used for priming immunization and (b) and (c) are used for boosting immunization, and the particle contained in (c) is different from the particle contained in (a) and (b), or the same as the particle contained in (a) or (b);
(31) The kit according to any one of (28)-(30), wherein the respective pharmaceutical compositions are administered simultaneously, separately or sequentially;
(32) A method of treating or preventing cancer or infectious disease; producing an antibody against PD-1 or a ligand of PD-1 in a mammal; modulating an immune response; immunostimulation; inhibiting an interaction between PD-1 and a ligand of PD-1; or inhibiting a PD-1 activity, comprising administering an effective amount of the particle according to any one of (1)-(16), the nucleic acid molecule according to any one of (17)-(20), the vector according to (20) or the pharmaceutical composition according to (21) or (22) to a subject in need thereof;
(33) The method according to (32), wherein the cancer is selected from the cancers described in (25) or (26);
(34) The method according to (32), wherein the infectious disease is selected from the infectious disease described in (27);
(35) A method for producing Chikungunya virus like particle or Venezuelan equine encephalitis virus like particle, comprising culturing a cell which is transfected with the vector according to (20) to express the particle; and purifying the particle using ultracentrifugation.

The present invention will be described in detail with reference to the following examples, which, however, are not intended to limit the scope of the present invention.

EXAMPLES

Example 1: Preparation of Chikungunya Virus (CHIKV) Like Particle Comprising a Virus Structural Protein and a Fragment of PD-1 Antigen The following polynucleotides of PD-1 were used to be inserted into VLP_CHI 532 vector (SEQ ID NO: 25). N terminal linker is SGG in amino acid sequence (TCCGGAGGA in nucleotide sequence) and C terminal linker is GGS in amino acid sequence (GGAGGATCC in nucleotide sequence).
1. VLP31 (PD-1 No. 1 sequence): A sequence of a PD-1 fragment attaching linker, which was used for an antigen:
Nucleotide Sequence (SEQ ID NO: 51)
Tccggaggactaaactggtaccgcatgagcccagcaaccagacggacaa
gctggccgccttcggaggatcc Amino Acid Sequence (SEQ ID NO: 52)
sgglnwyrmspsnqtdklaafggs 2. VLP32 (PD-1 No. 2 sequence): Another sequence of a PD-1 fragment attaching linker, which was used for an antigen:
Nucleotide Sequence (SEQ ID NO: 53)
Tcggcaggaatgctaaactggtaccgcatgagcccagcaaccagacgg
acaagctggccgccttctcaggaggatcc

Amino Acid Sequence (SEQ ID NO: 54)
sggmlnwyrmspsnqtdklaafsggs

3. VLP33 (PD-1 No. 3 sequence): Another sequence of a PD-1 fragment attaching linker, which was used for an antigen:
Nucleotide Sequence (SEQ ID NO: 55)
Tccggaggagtgctaaactggtaccgcatgagccccagcaaccagacgga
caagctggccgccttccccggaggatcc Amino Acid Sequence (SEQ ID NO: 56)
sggvlnwyrmspsnqtdklaafggs The respective polynucleotides was inserted between the codons encoding Ser at 531-position and Asn at 532-position of SEQ ID NO: 2 to construct a plasmid (hereinafter referred to as VLP31_11, VLP32_11 or VLP33_11) for expressing Chikungunya virus like particle where the modified PD-1-derived peptide is inserted into E2 of Chikungunya virus structural protein.

293F cells (Lifetechnology) were transfected with the plasmid using PEI (GE Healthcare) or GeneX (ATCC). 4 days after the transfection, the conditioned medium was collected and centrifuged at 3000 rpm for 15 minutes to separate it from cells. The supernatant was filtrated using 0.45 μm filter to obtain virus like particles. The virus like particles were concentrated using TFF column and purified using QXL column (GE Healthcare) to obtain purified virus like particles.

The expression of VLP comprising VLP31, 32 or 33 conjugated with Chikungunya virus structural protein was confirmed by Western Blot using an antibody specific for CHIKV (ATCC: VR-1241AF).

Example 2: Preparation of Venezuelan Equine Encephalitis Virus (VEEV) Like Particle Comprising a Virus Structural Protein and a Fragment of PD-1 Antigen The same polynucleotides of PD-1 used in EXAMPLE 1 were used to be inserted into VLP_VEEV VLP 518 vector (SEQ ID NO: 26). N terminal linker and C terminal linker are same in EXAMPLE 1.

The respective polynucleotides was inserted between the codons encoding Ser at 518-position and Ser at 519-position of SEQ ID NO: 3 to construct a plasmid (hereinafter referred to as VLP31_21, VLP32_21 or VLP33_21) for expressing Venezuelan equine encephalitis virus like particle where the modified PD-1-derived peptide is inserted into E2 of Venezuelan equine encephalitis structural protein.

293F cells were transfected with the plasmid like EXAMPLE 1. The expression of VLP comprising VLP 31, 32 or 33 conjugated with Venezuelan equine encephalitis virus structural protein was confirmed by Western Blot using an antibody specific for VEEV.

Example 3: Preparation of Chikungunya Virus (CHIKV) Like Particle and Venezuelan Equine Encephalitis Virus (VEEV) Like Particle Comprising a Virus Structural Protein and a Fragment of PD-1 Antigen or PD-L1 Antigen The following polynucleotides of mouse PD-1 and mouse PD-L1 were used to be inserted into VLP_CHI 532 vector (SEQ ID NO: 25) or to be inserted into VLP_VEEV VLP 518 vector (SEQ ID NO: 26). N terminal linker is SGG in amino acid sequence (TCCGGAGGA in nucleotide sequence) and C terminal linker is GGS in amino acid sequence (GGAGGATCC in nucleotide sequence).

1. VLP299 (mousePD-L1 sequence): A sequence of a fragment of mouse PD-L1 Domain3S attaching linker, which was used for an antigen:
Nucleotide Sequence (SEQ ID NO: 57)
Tccggaggatgcatcatcagctacggcggagccgactacggaggatcc Amino Acid Sequence (SEQ ID NO: 58)
SGG-ciisyggadyC-GGS 2. VLP274 (mousePD-1 sequence): A sequence of a fragment of mouse PD-1 domain2short attaching linker, which was used for an antigen:
Nucleotide Sequence (SEQ ID NO: 59)
Tccggaggaggcgccatcagcctgcaccccaaggccaagatcgaggaatc
tggaggatcc Amino Acid Sequence (SEQ ID NO: 60)
SGG-gaislhpkakiees-GS 3. VLP275 (mousePD-1 sequence): A sequence of a fragment of mouse PD-1 domain2short_v2 attaching linker, which was used for an antigen:
Nucleotide Sequence (SEQ ID NO: 61)
Tccggaggatgtggcgccatcagcctgcaccccaaggccaagatcgagga
aggaggatcc Amino Acid Sequence (SEQ ID NO: 62)
SGG-cgaislhpkakieeC-GGS The respective polynucleotides was inserted between the codons encoding Ser at 531-position and Asn at 532-position of SEQ ID NO: 2 to construct a plasmid (hereinafter referred to as VLP299_15, VLP299_25 for VLP299-inserted vector; VLP274_11, VLP274_15 for VLP274-inserted vector; VLP275_11, VLP275_15 for VLP275-inserted vector) for expressing Chikungunya virus like particle where the modified PD-1-derived peptide or the modified PD-L1-derived peptide is inserted into E2 of Chikungunya virus structural protein.

293F cells were transfected with the plasmid like EXAMPLE 1. The expression of VLP comprising VLP299, 274 or 275 conjugated with Chikungunya virus structural protein was confirmed by Western Blot using an antibody specific for CHIKV or VEEV.

Example 4: Immunogenicity of PD-1

The following polynucleotides of human PD-1, which is also found in the mouse PD-1 gene, was used to be inserted into VLP_CHI 532 vector (SEQ ID NO: 25) or to be inserted into VLP_VEEV VLP 518 vector (SEQ ID NO: 26). N terminal linker is SGG in amino acid sequence (TCCGGAGGA in nucleotide sequence) and C terminal linker is GGS in amino acid sequence (GGAGGATCC in nucleotide sequence).

Nucleotide Sequence (SEQ ID NO: 51)
Tccggaggactaaactggtaccgcatgagccccagcaaccagacggaca
agctggccgccttcggaggatcc Amino Acid Sequence (SEQ ID NO: 52)
SGGLNWYRMSPSNQTDKLAAFGGS The polynucleotides was inserted between the codons encoding Ser at 531-position and Asn at 532-position of SEQ ID NO: 2 to construct a plasmid (hereinafter referred to pCHIKV-hPD-1) for expressing Chikungunya virus like particle where the modified PD-1-derived peptide is inserted into E2 of Chikungunya virus structural protein. Also, the polynucleotides was inserted between the codons encoding Ser at 518-position and Ser at 519-position of SEQ ID NO: 3 to construct a plasmid (hereinafter referred to as pVEEV-hPD-1) for expressing Venezuelan equine encephalitis virus like particle where the modified PD-1-derived peptide is inserted into E2 of Venezuelan equine encephalitis structural protein.

293F cells (Lifetechnology) were transfected with the plasmid using PEI (GE Healthcare) or GeneX (ATCC). 4 days after the transfection, the conditioned medium was collected and centrifuged at 3000 rpm for 15 minutes to separate it from cells. The supernatant was filtrated using 0.45 μm filter to obtain virus like particles. The virus like particles were concentrated using TFF column and purified using QXL column (GE Healthcare) to obtain purified virus like particles. The purified virus like particles were further concentrated using spin column (Molecular Weight-cutoff: 100 kDa) to prepare the virus like particles for the immunization (CHIKV-hPD-1 and VEEV-hPD-1).

The mice (4 week old male) were immunized with the VEEV-hPD-1 2 times at 0 and 8 week (20 ug VLP per mouse) by intramuscle injection with Adjuvant Ribi, and immunized with CHIKV-hPD-1 once at 4 week (20 ug VLP per mouse) by intramuscle injection with Adjuvant Ribi (Sigma Adjuvant system, Sigma-Aldrich). The blood was taken at 10 weeks after the first immunization.

96 well ELISA plate were coated with 50 ng of Recombinant N-terminal fragment of PD-1 (1-167aa) or PD-1-Fc conjugate in 100 ul PBS buffer per well. The Plates after 2 hours incubation were washed three times TBS buffer containing 0.05% Tween-20 and blocked with TBS buffer containing 0.05% Tween-20 and 5% dry milk. The heat inactivated diluted serum from mice were added in the blocking buffer and incubated for 1 h at room temperature. After washing three times, peroxidase labeled goat anti-mouse IgG was added at 1:4000 dilution and incubated for 1 h at room temperature. After washing three times, Peroxidase substrate was added for development and incubated for 10 mins and 2N H2SO4 was added to stop the development. The data were analyzed using Gen5 (BioTek) and Graph Pad Prism6 (Graph Pad software Inc).

Figure 2:
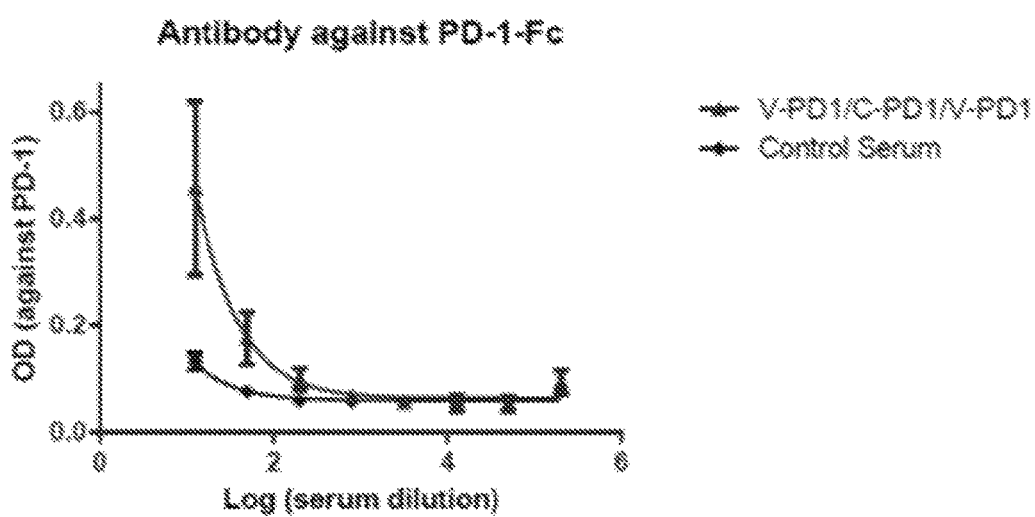
FIG. 2 shows results of ELISA where an antibody which binds to PD-1-Fc was detected.

The immunogenicities are shown in FIGS. 1 and 2. As seen from FIGS. 1 and 2, induction of antibodies against PD-1 was found in the serum of mice immunized with CHIKV-PD-1 and VEEV-PD-1.

Example 5: Preparation of a Pharmaceutical Composition Comprising Chikungunya Virus (CHIKV) Like Particle or Venezuelan Equine Encephalitis Virus (VEEV) Like Particle Comprising a Virus Structural Protein and a Fragment of PD-1 Antigen Chikungunya virus (CHIKV) like particle comprising a virus structural protein and a fragment of PD-1 antigen and Venezuelan equine encephalitis virus (VEEV) like particle a virus structural protein and a fragment of PD-1 antigen were prepared according to Example 4.

To prepare a pharmaceutical composition which is a vaccine composition, 80 μg of each of the prepared particles was mixed with 1 ml of Sucrose Phosphate Solution, pH 7.2, Endotoxin Free (Teknova, SP buffer).

The invention claimed is:

1. A virus-like particle comprising a virus structural protein and an antigen selected from the group consisting of (a)-(c):
   (a) an antigen which comprises a 10-300 amino acid fragment of human Programmed Death-1 (PD-1), or which comprises an amino acid sequence having at least 90% amino acid identity to said fragment of human PD-1;
   (b) an antigen which comprises a 10-300 amino acid fragment of human Programmed Death-Ligand 1 (PD-L1), or which comprises an amino acid sequence having at least 90% amino acid identity to said fragment of human PD-L1; and (c) an antigen which comprises a 10-300 amino acid fragment of human Programmed Death-Ligand 2 (PD-L2), or which comprises an amino acid sequence having at least 90% amino acid identity to said fragment of human PD-L2.

2. The virus-like particle according to claim 1, wherein the virus structural protein is an alphavirus or flavivirus polypeptide.

3. The virus-like particle according to claim 1, wherein the virus structural protein is a Chikungunya virus or Venezuelan equine encephalitis virus polypeptide.

4. The virus-like particle according to claim 1, wherein the virus structural protein comprises at least one protein selected from the group consisting of: a capsid protein, an E1 envelope protein, and an E2 envelope protein.

5. The virus-like particle according to claim 4, wherein said virus-like particle comprises an E2 envelope protein, and wherein said antigen is inserted into said E2 envelope protein.

6. The virus-like particle according to claim 1, wherein the virus-like particle contains capsid protein, envelope protein E1, and envelope protein E2 in which said antigen is inserted, wherein said envelope protein E2 into which the antigen is inserted consists of an amino acid sequence with at least 90% amino acid sequence identity to a sequence selected from the group consisting of SEQ ID NOs: 33-35, wherein said envelope protein E1 consists of an amino acid sequence with at least 90% amino acid sequence identity to SEQ ID NO: 37, and wherein said capsid protein consists of an amino acid sequence with at least 90% amino acid sequence identity to SEQ ID NO: 38.

7. The virus-like particle according to claim 1, wherein the virus-like particle contains capsid protein, envelope protein E1, and envelope protein E2 in which said antigen is inserted, wherein said envelope protein E2 into which the antigen is inserted consists of an amino acid sequence with at least 90% amino acid sequence identity to a sequence selected from the group consisting of SEQ ID NOs: 39-41, wherein said envelope protein E1 consists of an amino acid sequence with at least 90% amino acid sequence identity to SEQ ID NO: 43, and wherein said capsid protein consists of an amino acid sequence with at least 90% amino acid sequence identity to SEQ ID NO: 44.

8. The virus-like particle according to claim 1, wherein the virus-like particle contains capsid protein, envelope protein E1, and envelope protein E2 in which said antigen is inserted, wherein said envelope protein E2 into which the antigen is inserted consists of an amino acid sequence with at least 90% amino acid sequence identity to SEQ ID NO: 36, wherein said envelope protein E1 consists of an amino acid sequence with at least 90% amino acid sequence identity to SEQ ID NO: 37, and wherein said capsid protein consists of an amino acid sequence with at least 90% amino acid sequence identity to SEQ ID NO: 38.

9. The virus-like particle according to claim 1, wherein the virus-like particle contains capsid protein, envelope protein E1, and envelope protein E2 in which said antigen is inserted, wherein said envelope protein E2 into which the antigen is inserted consists of an amino acid sequence with at least 90% amino acid sequence identity to SEQ ID NO: 42, wherein said envelope protein E1 consists of an amino acid sequence with at least 90% amino acid sequence identity to SEQ ID NO: 43, and wherein said capsid protein consists of an amino acid sequence with at least 90% amino acid sequence identity to SEQ ID NO: 44.

10. An isolated nucleic acid molecule comprising a nucleotide sequence that encodes the entire virus-like particle according to claim 1.

11. A vector comprising the nucleic acid molecule according to claim 10, wherein the vector optionally comprises an expression control sequence operably linked to the nucleic acid molecule.

12. A pharmaceutical composition comprising:
(a) the virus-like particle according to claim 1; and
(b) a pharmaceutically acceptable carrier.

13. A vaccine composition comprising:
(a) the virus-like particle according to claim 1, and
(b) a pharmaceutically acceptable carrier.

14. A method for treating or preventing cancer or infectious disease; producing an antibody against PD-1 or a ligand of PD-1 in a mammal; modulating an immune response; immunostimulation; inhibiting an interaction between PD-1 and a ligand of PD-1; or inhibiting a PD-1 activity, comprising administering the virus-like particle according to claim 1 to a subject in need thereof.

15. A kit comprising:
(a) a pharmaceutical composition comprising the virus-like particle according to claim 1; and
(b) another pharmaceutical composition comprising the virus-like particle according to claim 1,
wherein the virus-like particle contained in (a) is a virus-like particle which is different from the virus-like particle contained in (b).

16. The kit according to claim 15, wherein the virus-like particle contained in (a) is a Chikungunya virus-like particle, and the virus-like particle contained in (b) is a Venezuelan equine encephalitis virus-like particle; or wherein the virus-like particle contained in (a) is a Venezuelan equine encephalitis virus-like particle, and the virus-like particle contained in (b) is a Chikungunya virus-like particle.

17. The virus-like particle according to claim 6, wherein said envelope protein E2 into which the antigen is inserted consists of an amino acid sequence selected from the group consisting of SEQ ID NOs: 33-35,
wherein said envelope protein E1 consists of the amino acid sequence of SEQ ID NO: 37,
and wherein said capsid protein consists of the amino acid sequence of SEQ ID NO: 38.

\* \* \* \* \*